(12) United States Patent
LaVallee et al.

(10) Patent No.: US 10,774,146 B2
(45) Date of Patent: *Sep. 15, 2020

(54) TREATMENT OF EOSINOPHIL OR MAST CELL RELATED DISORDERS

(71) Applicant: Celldex Therapeutics, Inc., Hampton, NJ (US)

(72) Inventors: Theresa Marie LaVallee, Rockville, MD (US); Gerald McMahon, Westport, CT (US)

(73) Assignee: Celldex Therapeutics, Inc., Hampton, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 16/270,116

(22) Filed: Feb. 7, 2019

(65) Prior Publication Data

US 2019/0153094 A1 May 23, 2019

Related U.S. Application Data

(62) Division of application No. 15/311,949, filed as application No. PCT/US2015/032134 on May 22, 2015, now Pat. No. 10,239,943.

(60) Provisional application No. 62/162,538, filed on May 15, 2015, provisional application No. 62/002,395, filed on May 23, 2014.

(51) Int. Cl.
*C07K 16/28* (2006.01)
*C07K 16/24* (2006.01)
*A61K 39/00* (2006.01)

(52) U.S. Cl.
CPC .......... *C07K 16/2803* (2013.01); *C07K 16/24* (2013.01); *A61K 2039/505* (2013.01); *C07K 2317/24* (2013.01); *C07K 2317/33* (2013.01); *C07K 2317/35* (2013.01); *C07K 2317/56* (2013.01); *C07K 2317/565* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| | | |
|---|---|---|
| 5,268,358 A | 12/1993 | Fretto |
| 5,489,516 A | 2/1996 | Broudy et al. |
| 5,545,533 A | 8/1996 | Bartke et al. |
| 5,686,572 A | 11/1997 | Wolf et al. |
| 5,808,002 A | 9/1998 | Bühring |
| 5,817,310 A | 10/1998 | Ramakrishnan et al. |
| 5,882,644 A | 3/1999 | Chang et al. |
| 5,891,652 A | 4/1999 | Wolf et al. |
| 5,906,938 A | 5/1999 | Broudy et al. |
| 5,911,988 A | 6/1999 | Brownell et al. |
| 5,919,911 A | 7/1999 | Broudy et al. |
| 5,922,847 A | 7/1999 | Broudy et al. |
| 6,001,803 A | 12/1999 | Besmer et al. |
| 6,403,559 B1 | 6/2002 | Besmer et al. |
| 6,495,331 B1 | 12/2002 | Gelfand et al. |
| 6,555,367 B1 | 4/2003 | Spence et al. |
| 6,576,812 B1 | 6/2003 | Longley et al. |
| 6,977,159 B1 | 12/2005 | Longley et al. |
| 6,989,248 B2 | 1/2006 | Longley |
| 6,998,391 B2 | 2/2006 | Lyons et al. |
| 7,303,893 B1 | 12/2007 | Chien et al. |
| 7,419,777 B2 | 9/2008 | Bacus |
| 7,449,309 B2 | 11/2008 | Longley |
| 7,906,302 B2 | 3/2011 | Longley |
| 7,915,391 B2 | 3/2011 | Ng et al. |
| 7,959,942 B2 | 6/2011 | Cottone |
| 8,088,060 B2 | 1/2012 | Cottone et al. |
| 8,133,485 B2 | 3/2012 | Levi-Schaffer et al. |
| 8,133,733 B2 | 3/2012 | Khan |
| 8,278,067 B2 | 10/2012 | Longley et al. |
| 8,436,150 B2 | 5/2013 | Ng et al. |
| 8,552,157 B2 | 10/2013 | Amatulli et al. |
| 8,791,249 B2 | 7/2014 | Ng et al. |
| 9,067,986 B2 | 6/2015 | Gurney et al. |
| 9,334,332 B2 | 5/2016 | Hadari et al. |
| 9,540,443 B2 | 1/2017 | Hadari et al. |
| 9,605,081 B2 | 3/2017 | Hadari et al. |
| 10,184,007 B2 | 1/2019 | Hadari et al. |

(Continued)

FOREIGN PATENT DOCUMENTS

| | | |
|---|---|---|
| EP | 0548867 A2 | 6/1993 |
| EP | 0787743 A2 | 8/1997 |

(Continued)

OTHER PUBLICATIONS

Vermersch et al., Masitinib Treatment in Patients with Progressive Multiple Sclerosis: a Randomized Pilot Studt, 2012, BMC Neurology 12:36, 9 pages, http://www.biomedcentral.com/1471-2377/12/36, 2012 (Year: 2012).*

Adams et al., 2006, "Humanization of a recombinant monoclonal antibody to produce a therapeutic HER dimerization inhibitor, Pertuzumab", Cander Immunol Immunother, 55:717-727 (published online Sep. 3, 2005).

Amir-Zaltsman et al., 2000, "Inhibitors of protein tyrosine phosphorylation: preliminary assessment of activity by time-resolved fluorescence", Luminescence, 15:377-380.

Ashman and Griffith, Jan. 2013, "Therapeutic targeting of c-KIT in cancer," Expert Opin Investig Drugs, 22(1):103-115.

Ashman et al., 1994, "Epitope mapping and functional studies with three monoclonal antibodies to the C-kit receptor tyrosine kinase", J Cell Physiol, 158(3):545-554.

(Continued)

*Primary Examiner* — John D Ulm
(74) *Attorney, Agent, or Firm* — Jones Day

(57) ABSTRACT

Provided herein are methods and uses involving antibodies that specifically bind to a KIT receptor tyrosine kinase for managing, treating, or preventing an eosinophil or mast cell related disorder and/or one or more symptoms thereof, for example a mast cell related disorder of the nervous system, e.g., central nervous system, for example neuromyelitis optica (NMO), neuromyelitis optica spectrum disorder (NMOSD), multiple sclerosis (MS), and neurofibromatosis (NF).

7 Claims, 10 Drawing Sheets

Figure 2A:
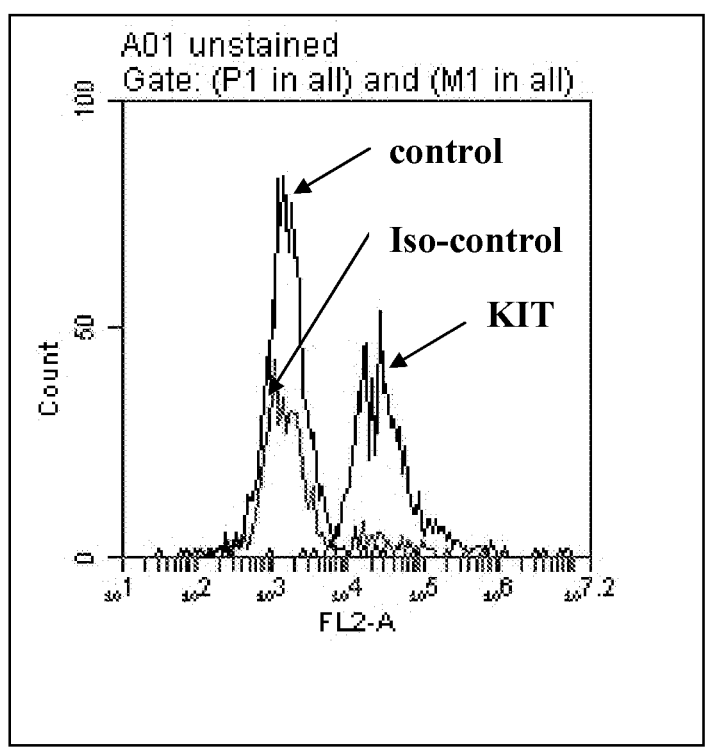

Specification includes a Sequence Listing.

(56) References Cited

U.S. PATENT DOCUMENTS

| | | |
|---|---|---|
| 10,189,907 B2 | 1/2019 | Hadari et al. |
| 10,239,943 B2 | 3/2019 | LaVallee et al. |
| 2002/0118775 A1 | 8/2002 | Persson et al. |
| 2004/0018593 A1 | 1/2004 | Jill et al. |
| 2004/0110226 A1 | 6/2004 | Lazar et al. |
| 2004/0248215 A1 | 12/2004 | Keler et al. |
| 2005/0004066 A1 | 1/2005 | Rockwell |
| 2005/0232917 A1 | 10/2005 | Pullen et al. |
| 2005/0244409 A1 | 11/2005 | Erickson-Miller et al. |
| 2005/0261175 A1 | 11/2005 | Zsebo et al. |
| 2005/0276784 A1 | 12/2005 | Besmer et al. |
| 2005/0281828 A1 | 12/2005 | Bowdish et al. |
| 2006/0019280 A1 | 1/2006 | Chen et al. |
| 2007/0004910 A1 | 1/2007 | Sexton et al. |
| 2007/0225202 A1 | 9/2007 | Andreev et al. |
| 2007/0253951 A1 | 11/2007 | Ng et al. |
| 2008/0032989 A1 | 2/2008 | Robinson et al. |
| 2008/0095775 A1 | 4/2008 | Lewis et al. |
| 2008/0213774 A1 | 9/2008 | Chen et al. |
| 2008/0260729 A1 | 10/2008 | Nash et al. |
| 2008/0274469 A1 | 11/2008 | Bastian et al. |
| 2008/0287309 A1 | 11/2008 | Bowdish et al. |
| 2009/0022740 A1 | 1/2009 | Bergstein |
| 2009/0022741 A1 | 1/2009 | Bergstein |
| 2009/0028879 A1 | 1/2009 | Bergstein |
| 2009/0075381 A1 | 3/2009 | Clarke et al. |
| 2009/0136450 A1 | 5/2009 | Chumakov et al. |
| 2009/0136497 A1 | 5/2009 | Longley et al. |
| 2009/0136517 A1 | 5/2009 | Garton et al. |
| 2009/0149389 A1 | 6/2009 | Panitch et al. |
| 2009/0169547 A1 | 7/2009 | Sahin et al. |
| 2009/0181017 A1 | 7/2009 | Hass et al. |
| 2009/0181022 A1 | 7/2009 | Nielson et al. |
| 2009/0186031 A1 | 7/2009 | Woods et al. |
| 2009/0191201 A1 | 7/2009 | Heiss et al. |
| 2009/0192133 A1 | 7/2009 | Horton |
| 2009/0233905 A1 | 9/2009 | Burke et al. |
| 2009/0246206 A1 | 10/2009 | Nielson et al. |
| 2009/0304625 A1 | 12/2009 | Husain et al. |
| 2010/0029674 A1 | 2/2010 | Tiollier et al. |
| 2010/0124569 A1 | 5/2010 | Abbot et al. |
| 2010/0129440 A1 | 5/2010 | Zhao et al. |
| 2010/0143935 A1 | 6/2010 | Davis |
| 2010/0173324 A1 | 7/2010 | Mori et al. |
| 2010/0196923 A1 | 8/2010 | Atala |
| 2010/0204058 A1 | 8/2010 | Chang et al. |
| 2010/0226927 A1 | 9/2010 | Weissman et al. |
| 2010/0298331 A1 | 11/2010 | Lee et al. |
| 2010/0316640 A1 | 12/2010 | Sundaram et al. |
| 2011/0059091 A1 | 3/2011 | Chang et al. |
| 2011/0091428 A1 | 4/2011 | Anversa |
| 2011/0123532 A1 | 5/2011 | Gurney et al. |
| 2011/0182866 A1 | 7/2011 | McNiece et al. |
| 2011/0195975 A1* | 8/2011 | Clapp ............... A61K 31/505 514/252.18 |
| 2011/0223165 A1 | 9/2011 | Ng et al. |
| 2011/0262465 A1 | 10/2011 | Gao et al. |
| 2011/0268776 A1 | 11/2011 | Schapira et al. |
| 2011/0281813 A1 | 11/2011 | Advani et al. |
| 2011/0293574 A1 | 12/2011 | Chute et al. |
| 2011/0311538 A1 | 12/2011 | Schlessinger et al. |
| 2011/0318351 A1 | 12/2011 | Bergstein |
| 2012/0065380 A1 | 3/2012 | Yoo et al. |
| 2012/0189633 A1 | 7/2012 | Hadari et al. |
| 2012/0328599 A1 | 12/2012 | Bae et al. |
| 2013/0011406 A1 | 1/2013 | Hadari et al. |
| 2013/0071397 A1 | 3/2013 | Schlessinger et al. |
| 2013/0184221 A9 | 7/2013 | Panitch et al. |
| 2013/0266595 A1 | 10/2013 | Flygare et al. |
| 2014/0056905 A1 | 2/2014 | Hadari et al. |
| 2014/0065168 A1 | 3/2014 | Hadari et al. |
| 2017/0073422 A1 | 3/2017 | Hadari et al. |
| 2017/0121408 A1 | 5/2017 | LaVallee et al. |
| 2017/0158778 A1 | 6/2017 | Hadari et al. |
| 2019/0100598 A1 | 4/2019 | Hadari et al. |
| 2019/0106510 A1 | 4/2019 | Hadari et al. |

FOREIGN PATENT DOCUMENTS

| | | |
|---|---|---|
| EP | 1378752 A1 | 1/2004 |
| EP | 0586445 B1 | 9/2004 |
| EP | 0889125 B1 | 8/2008 |
| JP | 2009534052 A | 9/2009 |
| JP | 2013510166 A | 3/2013 |
| WO | WO 1992/17505 A1 | 10/1992 |
| WO | WO 1992/021766 A1 | 12/1992 |
| WO | WO 1993/010805 A1 | 6/1993 |
| WO | WO 1998/41090 A1 | 9/1998 |
| WO | WO 2000/067794 A1 | 11/2000 |
| WO | WO 2001/034201 A2 | 5/2001 |
| WO | WO 2003/065995 A2 | 8/2003 |
| WO | WO 2003/091437 A1 | 11/2003 |
| WO | WO 2004/002425 A2 | 1/2004 |
| WO | WO 2005/095640 A1 | 10/2005 |
| WO | WO 2006/017173 A1 | 2/2006 |
| WO | WO 2007/004060 A2 | 1/2007 |
| WO | WO 2007/127317 A2 | 11/2007 |
| WO | WO 2008/112290 A2 | 9/2008 |
| WO | WO 2008/153926 A2 | 12/2008 |
| WO | WO 2009/082624 A2 | 7/2009 |
| WO | WO 2009/135001 A2 | 11/2009 |
| WO | WO 2009/152288 A1 | 12/2009 |
| WO | WO 2010/136508 A2 | 12/2010 |
| WO | WO 2011/057022 A1 | 5/2011 |
| WO | WO 2011/119948 A1 | 9/2011 |
| WO | WO 2012/093172 A1 | 7/2012 |
| WO | WO 2012/103165 A2 | 8/2012 |
| WO | WO 2012/154480 A1 | 11/2012 |
| WO | WO 2013/177481 A1 | 11/2013 |
| WO | WO 2014/018625 A1 | 1/2014 |
| WO | WO 2015/050959 A1 | 4/2015 |
| WO | WO 2015/112822 A1 | 7/2015 |

OTHER PUBLICATIONS

Ashman, Oct. 1999, "The biology of stem cell factor and its receptor C-kit," Int J Biochem Cell Biol, 31(10):1037-1051.

Atienza et al., 2006, "Label-free and real-time cell-based kinase assay for screening selective and potent receptor tyrosine kinase inhibitors using microelectronic sensor array", J Biomolec Screening, 11(6):634-643.

Bae et al., 2000, "Arginine-rich anti-vascular endothelial growth factor peptides inhibit tumor growth and metastasis by blocking angiogenesis", J Biol Chem, 275(18):13588-13596.

Bae et al., 2010, "Asymmetric recepor contact is required for tyrosine autophosphorylation of fibroblast growth factor receptor in living cells", Proc Natl Acad Sci USA, 107(7):2866-2867.

Balachandran et al., Mar. 2012, "Imatinib potentiates anti-tumor T cell responses in gastrointestinal stromal tumor through the inhibition of Ido," Nat Med, 17(9):1094-1100.

Baselga et al., 2005, "Critical update and emerging trends in epidermal growth factor receptor targeting in cancer", J Clin Oncol, 23(11):2445-2459.

Berezov et al., 2002, "Disabling receptor ensembles with rationally designed interface peptidomimetics", J Biol Chem, 277(31):28330-28339.

Besmer et al., 1986, "A new acute transforming feline retrovirus and relationship of its oncogene v-kit with the protein kinase gene family", Nature, 320:415-421.

Binetruy-Tournaire et al., 2000, "Identification of a peptide blocking vascular endothelial growth factor (VEGF)-mediated angiogenesis", EMBO J, 19(7):1525-1533.

Blechman et al., 1993a, "Soluble c-kit proteins and antireceptor monoclonal antibodies confine the binding site of stem cell factor", J Biol Chem, 268(6):4399-4406.

Blechman et al., 1993b, "Structure-function analyses of the kit receptor for the steel factor", Stem Cells, 11:12-21.

(56) References Cited

OTHER PUBLICATIONS

Blechman et al., 1995a, "The fourth immunolglobulin domain of the stem cell factor receptor couples ligand binding to signal transduction", Cell, 80:103-113.
Blechman and Yarden, 1995b, "Structural aspects of receptor dimerization. C-KIT as an example", Ann N Y Acad Sci 766:344-362.
Bradding, Jun. 2008, "Asthma eosinophil disease, mast cell disease, or both?" Allergy Asthma. Clin Immunol, 4(2):84-90.
Briddell et al., 1992, "Further phenotypic characterization and isolation of human hematopoietic progenitor cells using a monoclonal antibody to the c-kit receptor", Blood 79(12):3159-3167.
Broudy et al., Jan. 1992, "Isolation and characterization of a monoclonal antibody that recognizes the human c-kit receptor", Blood 79(2):338-346.
Broudy et al., 2001, "The fifth immunoglobulin-like domain of the Kit receptor is required for proteolytic cleavage from the cell surface", Cytokine 15(4):188-195.
Carlberg and Rohrschneider, 1994, "The effect of activating mutations on dimerization, tyrosine phosphorylation and internalization of the macrophage colony stimulating factor receptor", Molec Biol Cell, 5(1):81-95.
Chen et al., Jun. 1995, "Enhancement and destruction of antibody function by somatic mutation: unequal occurrence is controlled by V gene combinatorial associations," EMBO J, 14(12):2784-2794.
Chen et al., 2008, "A crystallographic snapshot of tyrosine trans-phosphorylation in action", Proc Natl Acad Sci USA, 105(50):19660-19665.
Cheon et al., Mar. 2011, "Mast cell 5-lipoxygenase activity promotes intestinal polyposis in APCDelta468 mice," Cancer Res, 71(5):1627-1636.
Christiansson et al., May 2015, "The tyrosine kinase inhibitors imatinib and dasatinib reduce myeloid suppressor cells and release effector lymphocyte responses," Mol Cancer Ther, 14(5):1181-1191.
Colman et al., Jan. 1994, "Effects of amino acid sequence changes on antibody-antigen interactions," Res Immunol, 145(1):33-36.
Coussens et al., Jun. 1999, "Inflammatory mast cells up-regulate angiogenesis during squamous epithelial carcinogenesis," Genes Dev, 13(11):1382-1397.
Edris et al., 2013, "Anti-KIT Monoclonal Antibody Inhibits Imatinib-resistant Gastrointestinal Stromal Tumor Growth", Proc. Natl. Acad. Sci. U S A., 110(9):3501-3506, (Epub Feb. 4, 2013).
Finke et al., Jul. 2011, "MDSC as a mechanism of tumor escape from sunitinib mediated anti-angiogenic therapy," Int Immunopharmacol, 11(7):856-861.
Galli et al., 1999, "The regulation of mast cell and basophil development by the Kit ligand, SCF, and IL-3," in: Razin E, Rivera J ed. Signal Transduction in Mast Cells and Basophils, pp. 11-30.
Garton et al., "Inhibition of KIT in vivo modifies immune cell populations to improve the efficacy of checkpoint inhibitors in syngeneic mouse tumor models," American Association for Cancer Research (AACR) Annual Meeting, Apr. 16-20, 2016, New Orleans, LA, Meeting Abstract published online Mar. 16, 2016.
Garton et al., "Inhibition of KIT in vivo modifies immune cell populations to improve the efficacy of checkpoint inhibitors in syngeneic mouse tumor models," American Association for Cancer Research (AACR) Annual Meeting, Apr. 16-20, 2016, New Orleans, LA, poster presented on Apr. 19, 2016.
Gedrich et al., "Regulation of Mast Cell Activity by KTN0158, a Humanized anti-KIT Monoclonal Antibody", Children's Tumor Foundation 2014 NF Conference, Jun. 7-10, 2014, Washington, D.C., Meeting Abstract.
Gedrich et al., "Regulation of Mast Cell Activity by KTN0158, a Humanized anti-KIT Monoclonal Antibody", Children's Tumor Foundation 2014 NF Conference, Jun. 7-10, 2014, Washington, D.C., Meeting Poster.
Gedrich et al., "Targeting KIT on innate immune cells enhances the antitumor activity of checkpoint inhibitors in vivo," Society for Immunotherapy of Cancer (SITC) 30th Annual Meeting, Nov. 6-8, 2015, National Harbor, MD, slide presentation on Nov. 7, 2015.
Gedrich et al., Nov. 4, 2015, "Targeting KIT on innate immune cells enhances the antitumor activity of checkpoint inhibitors in vivo," J Immunother Cancer 3(Suppl 2): O12, Meeting Abstract for Society for Immunotherapy of Cancer (SITC) 30th Annual Meeting, Nov. 6-8, 2015, National Harbor, MD.
GenBan Accession No. AAC50968.1 (KIT_MOUSE), dated Feb. 6, 1997. Retrieved from the Internet: URL<http://www.ncbi.nlm.nih.gov/entrez/viewer.fcgi?db=protein&id=1817733>.
GenBan Accession No. P05532, dated May 1, 2007. Retrieved from the Internet: URL<http://www.ncbi.nlm.nih.gov/entrez/viewer.fcgi?1254373:PROT:4572902>.
Granier et al., 2007, "Structure and conformational changes in the c-terminal domain of the beta2-adrenoceptoe", J Biol Chem, 282(18):13895-13905.
Grimbaldeston et al., Sep. 2005, "Mast cell-deficient W-sash c-kit mutant Kit W-sh/W-sh mice as a model for investigating mast cell biology in vivo," Am J Pathol, 167(3):835-848.
Harding et al., May-Jun. 2010, "The immunogenicity of humanized and fully human antibodies: residual immunogenicity resides in the CDR regions," Mabs, 2(3):256-265.
Hubbard et al., 2005, "EGF receptor inhibition: attacks on multiple fronts", Cancer Cell, 7(4):287-288.
Jacoby, et al., Dec. 1997, "Molecular analysis of the NF2 tumor-suppressor gene In schwannomatosis," Am J Hum Genet, 61(6):1293-1302.
Japanese Society for Bioinformatics (ed.), Encyclopedia of Bioinformatics, Jul. 1, 2006, pp. 462-463. (English abstract).
Jeffrey et al., Jul. 2013, A potent anti-CD70 antibody-drug conjugate combining a dimeric pyrrolobenzodiazepine drug with site-specific conjugation technology:, Bioconjugate Chem 24:1256-1263.
Jiang et al., 2000, "Structure of the active core of human stem cell factor and analysis of binding to its receptor kit", EMBO J, 19(13):3192-3203.
Joensuu, 2006, "Gastrointestinal stromal tumor (GIST)," Ann Oncol, 17 Suppl 10:x280-6.
Kao et al., Jan. 2011, "Targeting immune suppressing myeloid-derived suppressor cells in oncology," Crit Rev Oncol Hematol, 77(1):12-19.
Kussie et al., Jan. 1994, "A single engineered amino acid substitution changes antibody fine specificity," J Immunol, 152(1):146-152.
Lammie et al., Nov. 1994, "Expression of c-kit and kit ligand proteins in normal human tissues," J Histochem Cytochem, 42(11):1417-1425.
Larmonier et al., Nov. 2008, "Imatinib mesylate inhibits CD4+CD25+ regulatory T cell activity and enhances active immunotherapy against BCR-ABL-tumors," J Immunol, 181(10):6955-6963.
Lebron et al., 2014, "A human monoclonal antibody targeting the stem cell factor receptor (c-Kit) blocks tumor cell signaling and inhibits tumor growth", Cancer Biol Ther 1(9):1208-1218.
Lemmon et al., 1997, "Kit receptor dimerization is driven by bivalent binding of stem cell factor", J Biol Chem, 272(10):6311-6317.
Lemmon et al., 2007, "A new twist in the transmembrane signaling tool-kit", Cell, 130(2):213-215.
Lennartsson et al., 2004, "Synergistic growth of stem cell factor and granulocyte macrophage colony-stimulating factor involves kinase-dependent and -independent contributions from c-kit", J. Biol Chem, 279(43):44544-44553.
Lerner et al., May 1991, "Monoclonal Antibody YB5.B8 Identifies the Human c-kit Protein Product", 77:1876-1883.
Lev et al., 1992, "A recombinant ectodomain of the receptor for the stem cell factor (SCF) retains ligand-induced receptor dimerization and antagonizes SCF-stimulated cellular responses", J Biol Chem, 267(15):10866-10873.
Lev et al., 1993, "Interspecies molecular chimeras of Kit help define the binding site of the stem cell factor", Mol Cell Biol., 13(4):2224-2234.
Liang et al., 2013, "The c-kit receptor-mediated signal transduction and tumor-related diseases", Int. J. Biol. Sci., 9(5):435-443.
Liu et al., 2007, "Structural basis for stem cell factor: KIT signaling and activation of class III receptor tyrosine kinases", The EMBO Journal, 26(3):891-901.

(56) References Cited

OTHER PUBLICATIONS

Lokker et al., 1997, "Functional importance of platelet-derived growth factor (PDGF) receptor extracellular immunoglobulin-like domains", J Biol Chem, 272(52):33037-33044.
London et al., "KTN0158, a humanized anti-KIT monoclonal antibody, demonstrates antitumor activity in dogs with mast cell tumors," AACR-NCI-EORTC International Conference on Molecular Targets and Cancer Therapeutics, Nov. 5-9, 2015, Boston, MA, Meeting Abstract published online Oct. 26, 2015.
London et al., "KTN0158, a humanized anti-KIT monoclonal antibody, demonstrates antitumor activity in dogs with mast cell tumors," AACR-NCI-EORTC International Conference on Molecular Targets and Cancer Therapeutics, Nov. 5-9, 2015, Boston, MA, poster presented Nov. 8, 2015.
London et al., "KTN0158, a humanized anti-KIT monoclonal antibody, demonstrates antitumor activity in dogs with mast cell tumors," The European Cancer Congress (ECC 2015), Sep. 25-29, 2015, Vienna, Austria, Meeting Abstract published online Sep. 11, 2015.
London et al., "KTN0158, a humanized anti-KIT monoclonal antibody, demonstrates antitumor activity in dogs with mast cell tumors," The European Cancer Congress (ECC 2015), Sep. 25-29, 2015, Vienna, Austria, poster presented Sep. 28, 2015.
Lubeski et al., "KTN0182A, an anti-KIT, pyrrolobenzodiazepine (PBD)-containing antibody-drug conjugate (ADC) demonstrates potent antitumor activity in vitro and in vivo against a broad range of tumor types", 11th Annual PEGS, May 4-8, 2015, Boston, MA, Meeting Poster.
Lubeski et al., "KTN0182A, an anti-KIT, pyrrolobenzodiazepine (PBD)-containing antibody-drug conjugate (ADC) demonstrates potent antitumor activity in vitro and in vivo against a broad range of tumor types", 11th Annual PEGS, May 4-8, 2015, Boston, MA, Meeting Abstract.
Mandel et al., "KTN0158, a Humanized Anti-KIT Monoclonal Antibody, Reduces Airway Eosinophilia in a Feline Model of Allergic Asthma", American College of Allergy, Asthma & Immunology (ACAAI) 2014 Annual Scientific Meeting, Nov. 6-10, 2014, Atlanta, GA, Meeting Poster.
Mandel et al., "Regulation of Airway Eosinophilia in a Model of Feline Allergic Asthma by KTN0158, a Humanized anti-KIT Monoclonal Antibody", American College of Allergy, Asthma & Immunology (ACAAI) 2014 Annual Scientific Meeting, Nov. 6-10, 2014, Atlanta, GA, Meeting Abstract.
Matthews et al., 1991, "A receptor tyrosine kinase cDNA isolated from a population of enriched primitive hematopoietic cells and exhibiting close genetic linkage to c-kit", Proc Natl Acad Sci USA, 88:9026-9030.
Metcalfe et al., 1997, "Mast cells," Physiol Rev, 77:1033-1079.
Micke et al., 2003, "Characterization of c-kit expression in small cell lung cancer: prognostic therapeutic implications", Clin Cancer Res, 9:188-194.
Miettinen and Lasota, Sep. 2005, "KIT (CD117): a review on expression in normal and neoplastic tissues, and mutations and their clinicopathologic correlation," Appl Immunohistochem Mol Morphol, 13(3):205-220.
Mukherjee et al., Jun. 2009, "Human schwannomas express activated platelet-derived growth factor receptors and c-kit and are growth inhibited by Gleevec (Imatinib Mesylate)," Cancer Res, 69(12):5099-5107.
Nakayama and Parandoosh, 1999, "An immunoassay for assessment of receptor tyrosine kinase autophosphorylation", J Immunol Methods, 225:67-74.
Omura et al., 1997, "Immunoglobulin-like domain 4-mediated receptor-receptor interactions contribute to platelet-derived growth factor-induced receptor dimerization.", J Biol Chem, 272(19):12676-12682.
Ozao-Choy et al., Mar. 2009, "The novel role of tyrosine kinase inhibitor in the reversal of immune suppression and modulation of tumor microenvironment for immune-based cancer therapies," Cancer Res, 69(6):2514-2522.
Pan et al., Jan. 2008, "Reversion of immune tolerance in advanced malignancy: modulation of myeloid-derived suppressor cell development by blockade of stem-cell factor function," Blood, 111(1):219-228.
Philo et al., 1996, "Human stem cell factor dimer forms a complex with two molecules of the extracellular domain of its receptor, kit", J Biol Chem, 271(12):6895-6902.
Plotkin, et al., Apr. 2012, "Quantitative assessment of whole-body tumor burden in adult patients with 13/1, 13/2 neurofibromatosis," PLoS One, 7(4):e35711.
Protein Knowledgebase (UniProtKB), P10721 (KIT_HUMAN) [online] [retrieved on May 19, 2014]. Retrieved from the Internet http://www.uniport.org/uniprot/P10721#ref1, pp. 1-25.
Rådinger et al., Aug. 2010, "Generation, isolation, and maintenance of human mast cells and mast cell lines," Curr Protoc Immunol, Chapter 7:Unit 7.37.
Reith et al., Mar. 1990, "W mutant mice with mild or severe developmental defects contain distinct point mutations in the kinase domain of the c-kit receptor," Genes Dev, 4(3):390-400.
Reshetnyak et al., 2013, "Structural basis for KIT receptor tyrosine kinase inhibition by antibodies targeting the D4 membrane-proximal region", Proc Natl Acad Sci USA, 110(44):17832-17837.
Roskoski et al., 2004, "The ErbB/HER receptor protein-tyrosine kinases and cancer", Biochem Biophys Res Com, 319(1):1-11.
Ruch et al., 2007, "Structure of a VEGF-VEGF receptor complex determined by electron microscopy", Nat Struct Mol Biol, 14(3):249-250.
Rudikoff et al., Mar. 1982, "Single amino acid substitution altering antigen-binding specificity," Proc Natl Acad Sci U S A, 79(6):1979-1983.
Ryan et al., 1994, "Role for the stem cell factor/KIT complex in Schwann cell neoplasia and mast cell proliferation associated with neurofibromatosis", J Neurosci Res 37(3):415-432.
Sakai et al., 2007, "Pertuzumab, a novel HER dimerization inhibitor, inhibits the growth of human lung cancer cells mediated by the HER3 signaling pathway", Cancer Sci, 98(9):1498-1503.
Saleem et al., Jul. 15, 2012, "Cutting edge: mast cells critically augment myeloid-derived suppressor cell activity," J Immunol, 189(2):511-515.
Schittek et al., 1992, "Natural occurrence and origin of somatically mutated memory B cells in mice", J Exp Med, 176:427-428.
Schlessinger, Oct. 2000, "Cell signaling by receptor tyrosine kinases," Cell, 103(2):211-225.
Sequence Alignment, GenBan Accession No. AAC50968.1 (KIT_MOUSE), dated May 1, 2007. Retrieved from the Internet: URL<http://blast.ncbi.nlm.nih.gov/Blast.cgi>.
Shen et al., 2005, "Protein kinase inhibitors for treatment of cancer", Trends in Biopharmaceutical Industry, 1(3):15-19.
Shulman et al., 1997, "An antibody reactive with domain 4 of the platelet-derived growth beta receptor allows BB binding while inhibiting proliferation by impairing receptor dimerization", J Biol Chem, 272(28):17400-17404.
Soucek et al., Oct. 2007, "Mast cells are required for angiogenesis and macroscopic expansion of Myc-induced pancreatic islet tumors," Nat Med, 13(10):1211-1208.
Stahl et al., Jun. 2016, "Targeting KIT on innate immune cells to enhance the antitumor activity of checkpoint inhibitors," Immunotherapy, 8(7):767-774.
Starkey et al., Jul. 1988, "Mast-cell-deficient W/Wv mice exhibit A decreased rate of tumor angiogenesis," Int J Cancer, 42(1):48-52.
Staser et al., Nov. 2012, "Pathogenesis of plexiform neurofibroma: tumor-stromal/hematopoietic interactions in tumor progression," Annu Rev Pathol, 7:469-495.
Sugimura et al., 2002, "Human-Antibody Engineering (Review)", Bioventure, 2(4): 30-33. (English Abstract).
Tabone-Eglinger et al., 2008, "KIT mutations induce intracellular retention and activation of an immature form of the KIT protein in gastrointestinal stromal tumors", Clin Cancer Res 14(8):2285-2294.
Tamura et al., 2007, "Tyrosine kinases as targets for anti-inflammatory therapy", Anti-Inflammatory & Anti-Allergy Agents in Medicinal Chemistry, 6(1):47-60.

(56) References Cited

OTHER PUBLICATIONS

Tan et al., 2007, "Monitering interactions between receptor tyrosine kinases and their downstream effector proteins in living cells using bioluminescence resonance energy transfer", Molec Pharmacol, 72:1440-1446.
Tao et al., 2001, "Kinase insert domain receptor (KDR) extracellular immunoglobulin-like domains 4—contain structural features that block receptor dimerization and vascular endothelial g(rowth factor-induced signaling", J Biol Chem,): 276(24):21916-21923.
Theoharides and Conti, May 2004, "Mast cells: the Jekyll and Hyde of tumor growth," Trends Immunol, 25(5):235-241.
Ullrich and Schlessinger, Apr. 1990, "Signal transduction by receptors with tyrosine kinase activity," Cell, 61(2):203-212.
Uniprot Submission D2VI02_NAEGR, dated Mar. 2, 2010. Retrieved from the internet: <URL:http://www.uniprot.org/uniprot?D2VI02.txt?version=1>; aa 155-161.
Uniprot Submission QOUL05_PHANO, dated Mar. 2, 2010. [Retrieved from the Internet: <URL:http://www.uniprot.org/uniprot?QOUL05.txt?version=1>]; aa 598-608.
Wiesmann et al., 2000, "Ligand-binding sites in lg-like domains of receptor tyrosine kinases", J Molec Med, 78(5):247-260.
Wikipedia, The Free Encyclopedia, "Humanized_antibody," [online], Retrieved from the Internet:< URL: http://en.wikipedia.org/wiki/Humanized_antibody>, dated Mar. 28, 2012 (4 pages).
Yang et al., Oct. 2008, "Nf1-dependent tumors require a microenvironment containing Nfl+/−− and c-kit-dependent bone marrow", Cell 135(3):437-448.
Yang et al., Jan. 2010, "Mast cells mobilize myeloid-derived suppressor cells and Treg cells in tumor microenvironment via IL-17 pathway in murine hepatocarcinoma model," PLoS One, 5(1):e8922.
Yang et al., 2010, "Direct contacts between extracellular membrane-proximal domains are required for VEGF receptor activation and cell signaling", Proc Natl Acad Sci USA, 107(5):1906-1911.
Yarden et al., 1987, "Human proto-oncogene c-kit: a new cell surface receptor tyrosine kinase for an unidentified ligand", EMBO J, 6(11):3341-3351.
Yoo et al., 2005, "Arginine-rich anti-vascular endothelial growth factor (anti_VEGF) hexapeptide inhibits collagen-induced arthritis and VEGF-stimulated productions of TNF-alpha and IL-6 by human monocytes", J Immunol, 174(9):5846-5855.
Yuzawa et al., 2007, "Structural basis for activation of the receptor tyrosine KIT by stem cell factor", Cell, 13(2):323-334.
Zhang et al., 2000, "Crystal structure of human stem cell factot: implication for stem cell factor receptor dimerization and activation", Proc Natl Acad Sci USA, 97(14):7732-7737.
Zhang et al., 2006, "An allosteric mechanism for activation of kinase domain of epidermal growth factor receptor", Cell, 125:1137-1149.
Zhang et al., 2009, "Targeting cancer with small molecule kinase inhibitors", Nature Reviews Cancer, 9:28-39.
Zoog et al., Mar. 2009, "Antagonists of CD117 (cKit) signaling inhibit mast cell accumulation in healing skin wounds," Cytometry A, 75(3):189-198.
Secor et al., Mar. 2000, "Mast cells are essential for early onset and severe disease in a murine model of multiple sclerosis," J Exp Med 191(5):813-822.
Vajdos et al., Jul. 2002, "Comprehensive functional maps of the antigen-binding site of an anti-ErbB2 antibody obtained with shot-gun scanning mutagenesis," J Mol Biol 320(2):415-428.
Kodukula et al., Mar. 1991, "Biosynthesis of phosphatidylinositol glycan-anchored membrane proteins. Design of a simple protein substrate to characterize the enzyme that cleaves the cooh-terminal signal peptide," J Biol Chem 266(7): 4464-4470.
Lebron et al., Sep. 2014, "A human monoclonal antibody targeting the stem cell factor receptor (c-Kit) blocks tumor cell signaling and inhibits tumor growth," Cancer Biology & Therapy 15(9): 1208-1218 (published online in Jun. 2014).
Dodd et al., Sep.-Oct. 2010, "Animal models of soft-tissue sarcoma," Disease Models & Mechanisms 3(9-10): 557-566 (published online in Aug. 2010).
Imai and Takaoka, Sep. 2006, "Comparing antibody and small-molecule therapies for cancer," Nat Rev Cancer 6(9):714-727.
Staser et al., Jul. 2010, "Mast cells and the neurofibroma microenvironment," Blood 116(2):157-164.
Kati et al., Jan. 2006, "Tight junction proteins and perineurial cells in neurofibromas, " J Histochem Cytochem 54(1):53-61.
Robertson et al "Imatinib mesylate for plexiform neurofibromas in patients with neurofibromatosis type 1: A Phase 2 Trial", Lancet Oncol. 13:1218-1224; Oct. 23, 2012.
Brown et al., 2001, "Mechanisms underlying mast cell influence on EAE disease course," Molecular Immunology 38 (16-18): 1373-1378.
Notice of Allowance and Fee(s) Due dated May 19, 2020 in U.S. Appl. No. 16/214,980 (8 pages).
Notice of Allowance and Fee(s) Due dated May 5, 2020 in U.S. Appl. No. 16/221,002 (7 pages).

\* cited by examiner

```
  1   MRGARGAWDF LCVLLLLLRV QTGSSQPSVS PGEPSPPSIH PGKSDLIVRV GDEIRLLCTD PGFVKWTFEI LDETNENKQN
                                      {D1
                                                        }{D2
 81   EWITEKAEAT NTGKYTCTNK HGLSNSIYVF VRDPAKLFLV DRSLYGKEDN DTLVRCPLTD PEVTNYSLKG CQGKPLPKDL
161   RFIPDPKAGI MIKSVKRAYH RLCLHCSVDQ EGKSVLSEKF ILKVRPAFKA VPVVSVSKAS YLLREGEEFT VTCTIKDVSS
                                                   }{D3
241   SVYSTWKREN SQTKLQEKYN SWHHGDFNYE RQATLTISSA RVNDSGVFMC YANNTFGSAN VTTTLEVVDK GFINIFPMIN
                                                                                 }{D4
321   TTVFVNDGEN VDLIVEYEAF PKPEHQQWIY MNRTFTDKWE DYPKSENESN IRYVSELHLT RLKGTEGGTY TFLVSNSDVN
                 }{D5
401   AAIAFNVYVN TKPEILTYDR LVNGMLQCVA AGFPEPTIDW YFCPGTEQRC SASVLPVDVQ TLNSSGPPFG KLVVQSSIDS
481   SAFKHNGTVE CKAYNDVGKT SAYFNFAFKE QIHPHTLFTP LLIGFVIVAG MMCIIVMILT YKYLQKPMYE VQWKVVEEIN
                                                }
561   GNNYVYIDPT QLPYDHKWEF PRNRLSFGKT LGAGAFGKVV EATAYGLIKS DAAMTVAVKM LKPSAHLTER EALMSELKVL
641   SYLGNHMNIV NLLGACTIGG PTLVITEYCC YGDLLNFLRR KRDSFICSKQ EDHAEAALYK NLLHSKESSC SDSTNEYMDM
721   KPGVSYVVPT KADKRRSVRI GSYIERDVTP AIMEDDELAL DLEDLLSFSY QVAKGMAFLA SKNCIHRDLA ARNILLTHGR
801   ITKICDFGLA RDIKNDSNYV VKGNARLPVK WMAPESIFNC VYTFESDVWS YGIFLWELFS LGSSPYPGMP VDSKFYKMIK
881   EGFRMLSPEH APAEMYDIMK TCWDADPLKR PTFKQIVQLI EKQISESTNH IYSNLANCSP NRQKPVVDHS VRINSVGSTA
961   SSSQPLLVHD DV     (SEQ ID NO: 1)
```

Fig. 1

A

B

```
                       SEQUENCE LISTING

<160> NUMBER OF SEQ ID NOS: 18

<210> SEQ ID NO 1
<211> LENGTH: 972
<212> TYPE: PRT
<213> ORGANISM: Homo sapiens
<220> FEATURE:
<223> OTHER INFORMATION: human KIT receptor

<400> SEQUENCE: 1

Met Arg Gly Ala Arg Gly Ala Trp Asp Phe Leu Cys Val Leu Leu Leu
1               5                   10                  15

Leu Leu Arg Val Gln Thr Gly Ser Ser Gln Pro Ser Val Ser Pro Gly
                20                  25                  30

Glu Pro Ser Pro Pro Ser Ile His Pro Gly Lys Ser Asp Leu Ile Val
            35                  40                  45

Arg Val Gly Asp Glu Ile Arg Leu Leu Cys Thr Asp Pro Gly Phe Val
        50                  55                  60

Lys Trp Thr Phe Glu Ile Leu Asp Glu Thr Asn Glu Asn Lys Gln Asn
65                  70                  75                  80

Glu Trp Ile Thr Glu Lys Ala Glu Ala Thr Asn Thr Gly Lys Tyr Thr
                85                  90                  95

Cys Thr Asn Lys His Gly Leu Ser Asn Ser Ile Tyr Val Phe Val Arg
            100                 105                 110

Asp Pro Ala Lys Leu Phe Leu Val Asp Arg Ser Leu Tyr Gly Lys Glu
        115                 120                 125

Asp Asn Asp Thr Leu Val Arg Cys Pro Leu Thr Asp Pro Glu Val Thr
    130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
                165                 170                 175

Arg Ala Tyr His Arg Leu Cys Leu His Cys Ser Val Asp Gln Glu Gly
            180                 185                 190

Lys Ser Val Leu Ser Glu Lys Phe Ile Leu Lys Val Arg Pro Ala Phe
        195                 200                 205

Lys Ala Val Pro Val Val Ser Val Ser Lys Ala Ser Tyr Leu Leu Arg
    210                 215                 220

Glu Gly Glu Glu Phe Thr Val Thr Cys Thr Ile Lys Asp Val Ser Ser
225                 230                 235                 240

Ser Val Tyr Ser Thr Trp Lys Arg Glu Asn Ser Gln Thr Lys Leu Gln
                245                 250                 255
```

```
Glu Lys Tyr Asn Ser Trp His His Gly Asp Phe Asn Tyr Glu Arg Gln
            260                 265                 270

Ala Thr Leu Thr Ile Ser Ser Ala Arg Val Asn Asp Ser Gly Val Phe
            275                 280                 285

Met Cys Tyr Ala Asn Asn Thr Phe Gly Ser Ala Asn Val Thr Thr Thr
290                 295                 300

Leu Glu Val Val Asp Lys Gly Phe Ile Asn Ile Phe Pro Met Ile Asn
305                 310                 315                 320

Thr Thr Val Phe Val Asn Asp Gly Glu Asn Val Asp Leu Ile Val Glu
                325                 330                 335

Tyr Glu Ala Phe Pro Lys Pro Glu His Gln Gln Trp Ile Tyr Met Asn
            340                 345                 350

Arg Thr Phe Thr Asp Lys Trp Glu Asp Tyr Pro Lys Ser Glu Asn Glu
            355                 360                 365

Ser Asn Ile Arg Tyr Val Ser Glu Leu His Leu Thr Arg Leu Lys Gly
    370                 375                 380

Thr Glu Gly Gly Thr Tyr Thr Phe Leu Val Ser Asn Ser Asp Val Asn
385                 390                 395                 400

Ala Ala Ile Ala Phe Asn Val Tyr Val Asn Thr Lys Pro Glu Ile Leu
                405                 410                 415

Thr Tyr Asp Arg Leu Val Asn Gly Met Leu Gln Cys Val Ala Ala Gly
            420                 425                 430

Phe Pro Glu Pro Thr Ile Asp Trp Tyr Phe Cys Pro Gly Thr Glu Gln
            435                 440                 445

Arg Cys Ser Ala Ser Val Leu Pro Val Asp Val Gln Thr Leu Asn Ser
    450                 455                 460

Ser Gly Pro Pro Phe Gly Lys Leu Val Val Gln Ser Ser Ile Asp Ser
465                 470                 475                 480

Ser Ala Phe Lys His Asn Gly Thr Val Glu Cys Lys Ala Tyr Asn Asp
                485                 490                 495

Val Gly Lys Thr Ser Ala Tyr Phe Asn Phe Ala Phe Lys Glu Gln Ile
            500                 505                 510

His Pro His Thr Leu Phe Thr Pro Leu Leu Ile Gly Phe Val Ile Val
            515                 520                 525

Ala Gly Met Met Cys Ile Ile Val Met Ile Leu Thr Tyr Lys Tyr Leu
530                 535                 540

Gln Lys Pro Met Tyr Glu Val Gln Trp Lys Val Val Glu Glu Ile Asn
545                 550                 555                 560

Gly Asn Asn Tyr Val Tyr Ile Asp Pro Thr Gln Leu Pro Tyr Asp His
                565                 570                 575

Lys Trp Glu Phe Pro Arg Asn Arg Leu Ser Phe Gly Lys Thr Leu Gly
            580                 585                 590

Ala Gly Ala Phe Gly Lys Val Val Glu Ala Thr Ala Tyr Gly Leu Ile
            595                 600                 605

Lys Ser Asp Ala Ala Met Thr Val Ala Val Lys Met Leu Lys Pro Ser
    610                 615                 620

Ala His Leu Thr Glu Arg Glu Ala Leu Met Ser Glu Leu Lys Val Leu
625                 630                 635                 640

Ser Tyr Leu Gly Asn His Met Asn Ile Val Asn Leu Leu Gly Ala Cys
                645                 650                 655

Thr Ile Gly Gly Pro Thr Leu Val Ile Thr Glu Tyr Cys Cys Tyr Gly
            660                 665                 670
```

-continued

```
Asp Leu Leu Asn Phe Leu Arg Arg Lys Arg Asp Ser Phe Ile Cys Ser
            675                 680                 685
Lys Gln Glu Asp His Ala Glu Ala Leu Tyr Lys Asn Leu Leu His
    690                 695                 700
Ser Lys Glu Ser Ser Cys Ser Asp Ser Thr Asn Glu Tyr Met Asp Met
705                 710                 715                 720
Lys Pro Gly Val Ser Tyr Val Val Pro Thr Lys Ala Asp Lys Arg Arg
                725                 730                 735
Ser Val Arg Ile Gly Ser Tyr Ile Glu Arg Asp Val Thr Pro Ala Ile
            740                 745                 750
Met Glu Asp Asp Glu Leu Ala Leu Asp Leu Glu Asp Leu Leu Ser Phe
        755                 760                 765
Ser Tyr Gln Val Ala Lys Gly Met Ala Phe Leu Ala Ser Lys Asn Cys
    770                 775                 780
Ile His Arg Asp Leu Ala Ala Arg Asn Ile Leu Leu Thr His Gly Arg
785                 790                 795                 800
Ile Thr Lys Ile Cys Asp Phe Gly Leu Ala Arg Asp Ile Lys Asn Asp
                805                 810                 815
Ser Asn Tyr Val Val Lys Gly Asn Ala Arg Leu Pro Val Lys Trp Met
            820                 825                 830
Ala Pro Glu Ser Ile Phe Asn Cys Val Tyr Thr Phe Glu Ser Asp Val
        835                 840                 845
Trp Ser Tyr Gly Ile Phe Leu Trp Glu Leu Phe Ser Leu Gly Ser Ser
    850                 855                 860
Pro Tyr Pro Gly Met Pro Val Asp Ser Lys Phe Tyr Lys Met Ile Lys
865                 870                 875                 880
Glu Gly Phe Arg Met Leu Ser Pro Glu His Ala Pro Ala Glu Met Tyr
                885                 890                 895
Asp Ile Met Lys Thr Cys Trp Asp Ala Asp Pro Leu Lys Arg Pro Thr
            900                 905                 910
Phe Lys Gln Ile Val Gln Leu Ile Glu Lys Gln Ile Ser Glu Ser Thr
        915                 920                 925
Asn His Ile Tyr Ser Asn Leu Ala Asn Cys Ser Pro Asn Arg Gln Lys
    930                 935                 940
Pro Val Val Asp His Ser Val Arg Ile Asn Ser Val Gly Ser Thr Ala
945                 950                 955                 960
Ser Ser Ser Gln Pro Leu Leu Val His Asp Val
                965                 970

<210> SEQ ID NO 2
<211> LENGTH: 11
<212> TYPE: PRT
<213> ORGANISM: Artificial Sequence
<220> FEATURE:
<223> OTHER INFORMATION: CDR1 of light chain of anti-KIT antibody

<400> SEQUENCE: 2

Lys Ala Ser Gln Asn Val Arg Thr Asn Val Ala
1               5                   10

<210> SEQ ID NO 3
<211> LENGTH: 7
<212> TYPE: PRT
<213> ORGANISM: Artificial Sequence
<220> FEATURE:
<223> OTHER INFORMATION: CDR2 of light chain of anti-KIT antibody

<400> SEQUENCE: 3
```

```
Ser Ala Ser Tyr Arg Tyr Ser
1               5

<210> SEQ ID NO 4
<211> LENGTH: 9
<212> TYPE: PRT
<213> ORGANISM: Artificial Sequence
<220> FEATURE:
<223> OTHER INFORMATION: CDR3 of light chain of anti-KIT antibody

<400> SEQUENCE: 4

Gln Gln Tyr Asn Ser Tyr Pro Arg Thr
1               5

<210> SEQ ID NO 5
<211> LENGTH: 5
<212> TYPE: PRT
<213> ORGANISM: Artificial Sequence
<220> FEATURE:
<223> OTHER INFORMATION: CDR1 of heavy chain of anti-KIT antibody

<400> SEQUENCE: 5

Asp Tyr Tyr Ile Asn
1               5

<210> SEQ ID NO 6
<211> LENGTH: 17
<212> TYPE: PRT
<213> ORGANISM: Artificial Sequence
<220> FEATURE:
<223> OTHER INFORMATION: CDR2 of heavy chain of anti-KIT antibody

<400> SEQUENCE: 6

Arg Ile Tyr Pro Gly Ser Gly Asn Thr Tyr Tyr Asn Glu Lys Phe Lys
1               5                   10                  15

Gly

<210> SEQ ID NO 7
<211> LENGTH: 7
<212> TYPE: PRT
<213> ORGANISM: Artificial Sequence
<220> FEATURE:
<223> OTHER INFORMATION: CDR3 of heavy chain of anti-KIT antibody

<400> SEQUENCE: 7

Gly Val Tyr Tyr Phe Asp Tyr
1               5

<210> SEQ ID NO 8
<211> LENGTH: 116
<212> TYPE: PRT
<213> ORGANISM: Artificial Sequence
<220> FEATURE:
<223> OTHER INFORMATION: heavy chain variable region of anti-KIT
      antibody

<400> SEQUENCE: 8

Gln Val Gln Leu Val Gln Ser Gly Ala Glu Leu Lys Lys Pro Gly Ala
1               5                   10                  15

Ser Val Lys Leu Ser Cys Lys Ala Ser Gly Tyr Thr Phe Thr Asp Tyr
                20                  25                  30

Tyr Ile Asn Trp Val Lys Gln Ala Pro Gly Lys Gly Leu Glu Trp Ile
            35                  40                  45

Ala Arg Ile Tyr Pro Gly Ser Gly Asn Thr Tyr Tyr Asn Glu Lys Phe
```

```
                50                  55                  60
Lys Gly Arg Ala Thr Leu Thr Ala Glu Lys Ser Thr Ser Thr Ala Tyr
 65                  70                  75                  80

Met Gln Leu Ser Ser Leu Arg Ser Glu Asp Ser Ala Val Tyr Phe Cys
                 85                  90                  95

Ala Arg Gly Val Tyr Tyr Phe Asp Tyr Trp Gly Gln Gly Thr Thr Val
                100                 105                 110

Thr Val Ser Ser
        115

<210> SEQ ID NO 9
<211> LENGTH: 116
<212> TYPE: PRT
<213> ORGANISM: Artificial Sequence
<220> FEATURE:
<223> OTHER INFORMATION: heavy chain variable region of anti-KIT
      antibody

<400> SEQUENCE: 9

Gln Val Gln Leu Val Gln Ser Gly Ala Glu Val Lys Lys Pro Gly Ala
 1               5                  10                  15

Ser Val Lys Leu Ser Cys Lys Ala Ser Gly Tyr Thr Phe Thr Asp Tyr
                 20                  25                  30

Tyr Ile Asn Trp Val Lys Gln Ala Pro Gly Lys Gly Leu Glu Trp Ile
             35                  40                  45

Ala Arg Ile Tyr Pro Gly Ser Gly Asn Thr Tyr Tyr Asn Glu Lys Phe
 50                  55                  60

Lys Gly Arg Ala Thr Leu Thr Ala Glu Lys Ser Thr Ser Thr Ala Tyr
 65                  70                  75                  80

Met Gln Leu Ser Ser Leu Arg Ser Glu Asp Thr Ala Val Tyr Phe Cys
                 85                  90                  95

Ala Arg Gly Val Tyr Tyr Phe Asp Tyr Trp Gly Gln Gly Thr Thr Val
                100                 105                 110

Thr Val Ser Ser
        115

<210> SEQ ID NO 10
<211> LENGTH: 116
<212> TYPE: PRT
<213> ORGANISM: Artificial Sequence
<220> FEATURE:
<223> OTHER INFORMATION: heavy chain variable region of anti-KIT
      antibody

<400> SEQUENCE: 10

Gln Val Gln Leu Val Gln Ser Gly Ala Glu Val Lys Lys Pro Gly Ala
 1               5                  10                  15

Ser Val Lys Leu Ser Cys Lys Ala Ser Gly Tyr Thr Phe Thr Asp Tyr
                 20                  25                  30

Tyr Ile Asn Trp Val Arg Gln Ala Pro Gly Lys Gly Leu Glu Trp Ile
             35                  40                  45

Ala Arg Ile Tyr Pro Gly Ser Gly Asn Thr Tyr Tyr Asn Glu Lys Phe
 50                  55                  60

Lys Gly Arg Ala Thr Leu Thr Ala Asp Lys Ser Thr Ser Thr Ala Tyr
 65                  70                  75                  80

Met Gln Leu Ser Ser Leu Arg Ser Glu Asp Thr Ala Val Tyr Phe Cys
                 85                  90                  95

Ala Arg Gly Val Tyr Tyr Phe Asp Tyr Trp Gly Gln Gly Thr Thr Val
```

Thr Val Ser Ser
        115

<210> SEQ ID NO 11
<211> LENGTH: 116
<212> TYPE: PRT
<213> ORGANISM: Artificial Sequence
<220> FEATURE:
<223> OTHER INFORMATION: heavy chain variable region of anti-KIT
      antibody

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Asn Trp Val Arg Gln Ala Pro Gly Lys Gly Leu Glu Trp Ile
        35                  40                  45

Ala Arg Ile Tyr Pro Gly Ser Gly Asn Thr Tyr Tyr Asn Glu Lys Phe
    50                  55                  60

Lys Gly Arg Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Val Tyr Tyr Phe Asp Tyr Trp Gly Gln Gly Thr Thr Val
            100                 105                 110

Thr Val Ser Ser
        115

<210> SEQ ID NO 12
<211> LENGTH: 116
<212> TYPE: PRT
<213> ORGANISM: Artificial Sequence
<220> FEATURE:
<223> OTHER INFORMATION: heavy chain variable region of anti-KIT
      antibody

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Asn Trp Val Arg Gln Ala Pro Gly Lys Gly Leu Glu Trp Ile
        35                  40                  45

Ala Arg Ile Tyr Pro Gly Ser Gly Asn Thr Tyr Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Val Tyr Tyr Phe Asp Tyr Trp Gly Gln Gly Thr Thr Val
            100                 105                 110

Thr Val Ser Ser
        115

<210> SEQ ID NO 13
<211> LENGTH: 107
<212> TYPE: PRT

```
<213> ORGANISM: Artificial Sequence
<220> FEATURE:
<223> OTHER INFORMATION: light chain variable region of anti-KIT
      antibody

<400> SEQUENCE: 13

Asp Ile Val Met Thr Gln Ser Pro Ser Phe Leu Ser Ala Ser Val Gly
1               5                   10                  15

Asp Arg Val Thr Ile Thr Cys Lys Ala Ser Gln Asn Val Arg Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Ser Leu Gln Ser
65                  70                  75                  80

Glu Asp Phe Ala Asp Tyr Phe Cys Gln Gln Tyr Asn Ser Tyr Pro Arg
                85                  90                  95

Thr Phe Gly Gly Gly Thr Lys Val Glu Ile Lys
            100                 105

<210> SEQ ID NO 14
<211> LENGTH: 107
<212> TYPE: PRT
<213> ORGANISM: Artificial Sequence
<220> FEATURE:
<223> OTHER INFORMATION: light chain variable region of anti-KIT
      antibody

<400> SEQUENCE: 14

Asp Ile Val Met Thr Gln Ser Pro Ser Leu Ser Ala Ser Val Gly
1               5                   10                  15

Asp Arg Val Thr Ile Thr Cys Lys Ala Ser Gln Asn Val Arg Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Ser Leu Gln Pro
65                  70                  75                  80

Glu Asp Phe Ala Asp Tyr Phe Cys Gln Gln Tyr Asn Ser Tyr Pro Arg
                85                  90                  95

Thr Phe Gly Gly Gly Thr Lys Val Glu Ile Lys
            100                 105

<210> SEQ ID NO 15
<211> LENGTH: 107
<212> TYPE: PRT
<213> ORGANISM: Artificial Sequence
<220> FEATURE:
<223> OTHER INFORMATION: light chain variable region of anti-KIT
      antibody

<400> SEQUENCE: 15

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asn Val Arg Thr Asn
            20                  25                  30

Val Ala Trp Tyr Gln Gln Lys Pro Gly Lys Ala Pro Lys Ala Leu Ile
        35                  40                  45
```

```
Tyr Ser Ala Ser Tyr Arg Tyr Ser Gly Val Pro Asp Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Asp Tyr Phe Cys Gln Gln Tyr Asn Ser Tyr Pro Arg
                85                  90                  95

Thr Phe Gly Gly Gly Thr Lys Val Glu Ile Lys
            100                 105

<210> SEQ ID NO 16
<211> LENGTH: 107
<212> TYPE: PRT
<213> ORGANISM: Artificial Sequence
<220> FEATURE:
<223> OTHER INFORMATION: light chain variable region of anti-KIT
      antibody

<400> SEQUENCE: 16

Asp Ile Val Met Thr Gln Ser Pro Ser Ser Leu Ser Ala Ser Val Gly
  1               5                  10                  15

Asp Arg Val Thr Ile Thr Cys Lys Ala Ser Gln Asn Val Arg Thr Asn
             20                  25                  30

Val Ala Trp Tyr Gln Gln Lys Pro Gly Lys Ala Pro Lys Ser Leu Ile
         35                  40                  45

Tyr Ser Ala Ser Tyr Arg Tyr Ser Gly Val Pro Asp Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Arg
                85                  90                  95

Thr Phe Gly Gly Gly Thr Lys Val Glu Ile Lys
            100                 105

<210> SEQ ID NO 17
<211> LENGTH: 107
<212> TYPE: PRT
<213> ORGANISM: Artificial Sequence
<220> FEATURE:
<223> OTHER INFORMATION: light chain variable region consensus sequence
<220> FEATURE:
<221> NAME/KEY: VARIANT
<222> LOCATION: 10, 46, 63, 80, 85, 87
<223> OTHER INFORMATION: Xaa = Any Amino Acid

<400> SEQUENCE: 17

Asp Ile Val Met Thr Gln Ser Pro Ser Xaa Leu Ser Ala Ser Val Gly
  1               5                  10                  15

Asp Arg Val Thr Ile Thr Cys Lys Ala Ser Gln Asn Val Arg Thr Asn
             20                  25                  30

Val Ala Trp Tyr Gln Gln Lys Pro Gly Lys Ala Pro Lys Xaa Leu Ile
         35                  40                  45

Tyr Ser Ala Ser Tyr Arg Tyr Ser Gly Val Pro Asp Arg Phe Xaa Gly
    50                  55                  60

Ser Gly Ser Gly Thr Asp Phe Thr Leu Thr Ile Ser Ser Leu Gln Xaa
 65                  70                  75                  80

Glu Asp Phe Ala Xaa Tyr Xaa Cys Gln Gln Tyr Asn Ser Tyr Pro Arg
                85                  90                  95

Thr Phe Gly Gly Gly Thr Lys Val Glu Ile Lys
            100                 105
```

```
<210> SEQ ID NO 18
<211> LENGTH: 116
<212> TYPE: PRT
<213> ORGANISM: Artificial Sequence
<220> FEATURE:
<223> OTHER INFORMATION: heavy chain variable region consensus sequence
<220> FEATURE:
<221> NAME/KEY: VARIANT
<222> LOCATION: 11, 20, 38, 68, 70, 73, 82, 91
<223> OTHER INFORMATION: Xaa = Any Amino Acid

<400> SEQUENCE: 18

Gln Val Gln Leu Val Gln Ser Gly Ala Glu Xaa Lys Lys Pro Gly Ala
1               5                   10                  15

Ser Val Lys Xaa Ser Cys Lys Ala Ser Gly Tyr Thr Phe Thr Asp Tyr
            20                  25                  30

Tyr Ile Asn Trp Val Xaa Gln Ala Pro Gly Lys Gly Leu Glu Trp Ile
        35                  40                  45

Ala Arg Ile Tyr Pro Gly Ser Gly Asn Thr Tyr Tyr Asn Glu Lys Phe
    50                  55                  60

Lys Gly Arg Xaa Thr Xaa Thr Ala Xaa Lys Ser Thr Ser Thr Ala Tyr
65                  70                  75                  80

Met Xaa Leu Ser Ser Leu Arg Ser Glu Asp Xaa Ala Val Tyr Phe Cys
            85                  90                  95

Ala Arg Gly Val Tyr Tyr Phe Asp Tyr Trp Gly Gln Gly Thr Thr Val
                100                 105                 110

Thr Val Ser Ser
            115
```

TREATMENT OF EOSINOPHIL OR MAST CELL RELATED DISORDERS

This application is a divisional application of U.S. patent application Ser. No. 15/311,949, which is a U.S. national stage of International Patent Application No. PCT/US2015/032134, filed May 22, 2015, which claims the benefit of U.S. Provisional Application No. 62/002,395, filed on May 23, 2014, and 62/162,538, filed on May 15, 2015; the foregoing applications are incorporated by reference herein in their entireties.

This application incorporates by reference a Sequence Listing submitted with this application as text file entitled "Sequence_Listing_12638-123-228.TXT" created on May 21, 2015 and having a size of 21,490 bytes.

1. FIELD

Provided herein are methods and uses involving antibodies that specifically bind to KIT, a receptor tyrosine kinase, for managing, treating, or preventing an eosinophil or mast cell related disorder, such as mast cell related disorders of the nervous system, e.g., central nervous system, for example neuromyelitis optica (NMO), neuromyelitis optica spectrum disorder (NMOSD), multiple sclerosis (MS), and neurofibromatosis (NF).

2. BACKGROUND

Eosinophils are bone marrow-derived granulocytes implicated beneficially in host defense against infection, in anti-tumor cytotoxicity, and in wound healing. The abundance of eosinophils can contribute to inflammation, such as in the respiratory mucosal tissue from patients with asthma or rhinitis (see, e.g., Yuan et al., J. Exp. Med., 1997, 186:313-333).

Mast cells reside within the connective tissue of a variety of tissues and vascularized organs. They are also found at interfaces between the internal and external environments, such as the dermis, gut mucosa and submucosa, conjunctiva, pulmonary alveoli and airways, and the atrial appendage of the heart, where they can respond to foreign organisms and antigens. Inflammatory and allergic reactions involve mast-cell degranulation and mast-cell activation producing release of inflammatory factors and local or systemic immediate hypersensitivity reactions. Imbalance or improper regulation of mast cell activity is associated with detrimental exaggerated reactions to antigen observed in disorders such as anaphylaxis, atopy, and rhinitis.

There is a need for therapies to manage or treat eosinophil or mast cell related disorders effectively.

3. SUMMARY

In one aspect, provided herein is a method of protecting against, treating, or managing an eosinophil or mast cell related disorder of the nervous system, e.g., central nervous system in a subject, comprising administering to a subject in need thereof a therapeutically effective amount of an antibody which specifically binds to a human KIT receptor (SEQ ID NO: 1), or an antigen binding fragment thereof.

In another aspect, provided herein is a method of protecting against, treating, or managing NMO in a subject, comprising administering to a subject in need thereof a therapeutically effective amount of an antibody which specifically binds to a human KIT receptor (SEQ ID NO: 1), or an antigen binding fragment thereof.

In a particular aspect, provided herein is a method of protecting against, treating, or managing an NMOSD a subject, comprising administering to a subject in need thereof a therapeutically effective amount of an antibody which specifically binds to a human KIT receptor (SEQ ID NO: 1), or an antigen binding fragment thereof.

In another aspect, provided herein is a method of protecting against, treating, or managing MS in a subject, comprising administering to a subject in need thereof a therapeutically effective amount of an antibody which specifically binds to a human KIT receptor (SEQ ID NO: 1), or an antigen binding fragment thereof.

In a specific aspect, provided herein is a method of protecting against, treating, or managing NF in a subject, comprising administering to a subject in need thereof a therapeutically effective amount of an antibody which specifically binds to a human KIT receptor (SEQ ID NO: 1), or an antigen binding fragment thereof.

In one aspect, provided herein is a method of inhibiting growth of neurofibromas in a subject, comprising administering to a subject diagnosed with NF a therapeutically effective amount of an antibody which specifically binds to a human KIT receptor (SEQ ID NO: 1), or an antigen binding fragment thereof.

In another aspect, provided herein is a method of reducing inflammation, for example, inflammation of the nervous system, e.g., central nervous system, in a subject, comprising administering to a subject diagnosed with a mast cell related disorder of the central nervous system or nervous system a therapeutically effective amount of an antibody which specifically binds to a human KIT receptor (SEQ ID NO: 1), or an antigen binding fragment thereof.

In a particular aspect, provided herein is a method of inhibiting mast cell activation in a subject, comprising administering to a subject diagnosed with a mast cell related disorder of the nervous system, e.g., central nervous system, a therapeutically effective amount of an antibody which specifically binds to a human KIT receptor (SEQ ID NO: 1), or an antigen binding fragment thereof.

In a specific aspect, the mast cell related disorder of the nervous system, e.g., central nervous system, is NMO, NMOSD, MS, or NF. In a particular aspect, the type of NF is NF1, NF2, or Schwannomatosis.

In one aspect, the anti-KIT antibody for use in the methods provided herein is a bivalent monospecific antibody. In certain aspects, the anti-KIT antibody for use in the methods provided herein is a humanized antibody. In particular aspects, the anti-KIT antibody for use in the methods provided herein is a naked antibody. In one aspect, the anti-KIT antibody for use in the methods provided herein is not a bispecific antibody.

In particular aspects, the anti-KIT antibody for use in the methods provided herein comprises a light chain variable region ("VL") comprising VL CDRs 1-3 comprising SEQ ID NOs: 2-4, respectively, and a heavy chain variable region ("VH") comprising VH CDRs 1-3 comprising SEQ ID NOs: 5-7, respectively.

In one aspect, the subject to whom an anti-KIT antibody described herein is administered is a human adult. In a certain aspect, the subject to whom an anti-KIT antibody described herein is administered is a child.

Presented, below, are non-limiting embodiments of the methods described herein:

1. A method of treating a mast cell related disorder of the nervous system in a subject, comprising administering to a subject in need thereof a therapeutically effective amount of an antibody which specifically binds to a human KIT receptor (SEQ ID NO: 1), or an antigen binding fragment thereof.

2. A method of treating an eosinophil related disorder of the nervous system in a subject, comprising administering to a subject in need thereof a therapeutically effective amount of an antibody which specifically binds to a human KIT receptor (SEQ ID NO: 1), or an antigen binding fragment thereof.

3. The method of embodiment 1 or 2, wherein the antibody is a bivalent monospecific antibody.

4. The method of embodiment 3, wherein the antibody is a humanized antibody.

5. The method of embodiment 4, wherein the antibody is a naked antibody.

6. The method of embodiment 3, wherein the antibody is a naked antibody.

7. The method of embodiment 1 or 2, wherein the antibody is a humanized antibody.

8. The method of embodiment 7, wherein the antibody is a naked antibody.

9. The method of embodiment 1 or 2, wherein the antibody is a naked antibody.

10. The method of any one of embodiments 1-9, comprising administering a therapeutically effective amount of an antibody which specifically binds to a human KIT receptor (SEQ ID NO:1).

11. The method of embodiment 1 or 2, wherein the antibody comprises a light chain variable region ("VL") comprising VL CDRs 1-3 comprising SEQ ID NOs: 2-4, respectively, and a heavy chain variable region ("VH") comprising VH CDRs 1-3 comprising SEQ ID NOs: 5-7, respectively.

12. The method of embodiment 11, wherein the antibody is a bivalent monospecific antibody.

13. The method of embodiment 12, wherein the antibody is a humanized antibody.

14. The method of embodiment 13, wherein the antibody is a naked antibody.

15. The method of embodiment 12, wherein the antibody is a naked antibody.

16. The method of embodiment 11, wherein the antibody is a humanized antibody.

17. The method of embodiment 16, wherein the antibody is a naked antibody.

18. The method of embodiment 11, wherein the antibody is a naked antibody.

19. The method of any one of embodiments 11-19, comprising administering a therapeutically effective amount of an antibody which specifically binds to a human KIT receptor (SEQ ID NO:1).

20. The method of embodiment 11, wherein the antibody comprises a VH comprising SEQ ID NO: 8.

21. The method of embodiment 11, wherein the antibody comprises a VH comprising SEQ ID NO: 9.

22. The method of embodiment 11, wherein the antibody comprises a VH comprising SEQ ID NO: 10.

23. The method of embodiment 11, wherein the antibody comprises a VH comprising SEQ ID NO: 11.

24. The method of embodiment 11, wherein the antibody comprises a VH comprising SEQ ID NO: 12.

25. The method of embodiment 11, wherein the antibody comprises a VL comprising SEQ ID NO: 13.

26. The method of embodiment 11, wherein the antibody comprises a VL comprising SEQ ID NO: 14.

27. The method of embodiment 11, wherein the antibody comprises a VL comprising SEQ ID NO: 15.

28. The method of embodiment 11, wherein the antibody comprises a VL comprising SEQ ID NO: 16.

29. The method of embodiment 11, wherein the antibody comprises a VH comprising SEQ ID NO: 8 and a VL comprising SEQ ID NO:13.

30. The method of embodiment 11, wherein the antibody comprises a VH comprising SEQ ID NO: 8 and a VL comprising SEQ ID NO:14.

31. The method of embodiment 11, wherein the antibody comprises a VH comprising SEQ ID NO: 8 and a VL comprising SEQ ID NO:15.

32. The method of embodiment 11, wherein the antibody comprises a VH comprising SEQ ID NO: 8 and a VL comprising SEQ ID NO:16.

33. The method of embodiment 11, wherein the antibody comprises a VH comprising SEQ ID NO: 9 and a VL comprising SEQ ID NO:13.

34. The method of embodiment 11, wherein the antibody comprises a VH comprising SEQ ID NO: 9 and a VL comprising SEQ ID NO:14.

35. The method of embodiment 11, wherein the antibody comprises a VH comprising SEQ ID NO: 9 and a VL comprising SEQ ID NO:15.

36. The method of embodiment 11, wherein the antibody comprises a VH comprising SEQ ID NO: 9 and a VL comprising SEQ ID NO:16.

37. The method of embodiment 11, wherein the antibody comprises a VH comprising SEQ ID NO: 10 and a VL comprising SEQ ID NO:13.

38. The method of embodiment 11, wherein the antibody comprises a VH comprising SEQ ID NO: 10 and a VL comprising SEQ ID NO:14.

39. The method of embodiment 11, wherein the antibody comprises a VH comprising SEQ ID NO: 10 and a VL comprising SEQ ID NO:15.

40. The method of embodiment 11, wherein the antibody comprises a VH comprising SEQ ID NO: 10 and a VL comprising SEQ ID NO:16.

41. The method of embodiment 11, wherein the antibody comprises a VH comprising SEQ ID NO: 11 and a VL comprising SEQ ID NO:13.

42. The method of embodiment 11, wherein the antibody comprises a VH comprising SEQ ID NO: 11 and a VL comprising SEQ ID NO:14.

43. The method of embodiment 11, wherein the antibody comprises a VH comprising SEQ ID NO: 11 and a VL comprising SEQ ID NO:15.

44. The method of embodiment 11, wherein the antibody comprises a VH comprising SEQ ID NO: 11 and a VL comprising SEQ ID NO:16.

45. The method of embodiment 11, wherein the antibody comprises a VH comprising SEQ ID NO: 11.

46. The method of embodiment 11, wherein the antibody comprises a VH comprising SEQ ID NO: 12 and a VL comprising SEQ ID NO:13.

47. The method of embodiment 11, wherein the antibody comprises a VH comprising SEQ ID NO: 12 and a VL comprising SEQ ID NO:14.

48. The method of embodiment 11, wherein the antibody comprises a VH comprising SEQ ID NO: 12 and a VL comprising SEQ ID NO:15.

49. The method of embodiment 11, wherein the antibody comprises a VH comprising SEQ ID NO: 12 and a VL comprising SEQ ID NO:16.

50. The method of any one of embodiments 20-49, comprising administering a therapeutically effective amount of an antibody which specifically binds to a human KIT receptor (SEQ ID NO:1).

51. A method of managing a mast cell related disorder of the nervous system in a subject, comprising administering to a subject in need thereof a therapeutically effective amount of an antibody which specifically binds to a human KIT receptor (SEQ ID NO: 1), or an antigen binding fragment thereof.

52. A method of managing an eosinophil related disorder of the nervous system in a subject, comprising administering to a subject in need thereof a therapeutically effective amount of an antibody which specifically binds to a human KIT receptor (SEQ ID NO: 1), or an antigen binding fragment thereof.

53. The method of embodiment 51 or 52, wherein the antibody is a bivalent monospecific antibody.

54. The method of embodiment 53, wherein the antibody is a humanized antibody.

55. The method of embodiment 54, wherein the antibody is a naked antibody.

56. The method of embodiment 53, wherein the antibody is a naked antibody.

57. The method of embodiment 51 or 52, wherein the antibody is a humanized antibody.

58. The method of embodiment 57, wherein the antibody is a naked antibody.

59. The method of embodiment 51 or 52, wherein the antibody is a naked antibody.

60. The method of any one of embodiments 51-59, comprising administering a therapeutically effective amount of an antibody which specifically binds to a human KIT receptor (SEQ ID NO:1).

61. The method of embodiment 51 or 52, wherein the antibody comprises a light chain variable region ("VL") comprising VL CDRs 1-3 comprising SEQ ID NOs: 2-4, respectively, and a heavy chain variable region ("VH") comprising VH CDRs 1-3 comprising SEQ ID NOs: 5-7, respectively.

62. The method of embodiment 61, wherein the antibody is a bivalent monospecific antibody.

63. The method of embodiment 62, wherein the antibody is a humanized antibody.

64. The method of embodiment 61, wherein the antibody is a naked antibody.

65. The method of embodiment 62, wherein the antibody is a naked antibody.

66. The method of embodiment 61, wherein the antibody is a humanized antibody.

67. The method of embodiment 66, wherein the antibody is a naked antibody.

68. The method of embodiment 61, wherein the antibody is a naked antibody.

69. The method of any one of embodiments 61-68, comprising administering a therapeutically effective amount of an antibody which specifically binds to a human KIT receptor (SEQ ID NO:1).

70. The method of embodiment 61, wherein the antibody comprises a VH comprising SEQ ID NO: 8.

71. The method of embodiment 61, wherein the antibody comprises a VH comprising SEQ ID NO: 9.

72. The method of embodiment 61, wherein the antibody comprises a VH comprising SEQ ID NO: 10.

73. The method of embodiment 61, wherein the antibody comprises a VH comprising SEQ ID NO: 11.

74. The method of embodiment 61, wherein the antibody comprises a VH comprising SEQ ID NO: 12.

75. The method of embodiment 61, wherein the antibody comprises a VL comprising SEQ ID NO: 13.

76. The method of embodiment 61, wherein the antibody comprises a VL comprising SEQ ID NO: 14.

77. The method of embodiment 61, wherein the antibody comprises a VL comprising SEQ ID NO: 15.

78. The method of embodiment 61, wherein the antibody comprises a VL comprising SEQ ID NO: 16.

79. The method of embodiment 61, wherein the antibody comprises a VH comprising SEQ ID NO: 8 and a VL comprising SEQ ID NO:13.

80. The method of embodiment 61, wherein the antibody comprises a VH comprising SEQ ID NO: 8 and a VL comprising SEQ ID NO:14.

81. The method of embodiment 61, wherein the antibody comprises a VH comprising SEQ ID NO: 8 and a VL comprising SEQ ID NO:15.

82. The method of embodiment 61, wherein the antibody comprises a VH comprising SEQ ID NO: 8 and a VL comprising SEQ ID NO:16.

83. The method of embodiment 61, wherein the antibody comprises a VH comprising SEQ ID NO: 9 and a VL comprising SEQ ID NO:13.

84. The method of embodiment 61, wherein the antibody comprises a VH comprising SEQ ID NO: 9 and a VL comprising SEQ ID NO:14.

85. The method of embodiment 61, wherein the antibody comprises a VH comprising SEQ ID NO: 9 and a VL comprising SEQ ID NO:15.

86. The method of embodiment 61, wherein the antibody comprises a VH comprising SEQ ID NO: 9 and a VL comprising SEQ ID NO:16.

87. The method of embodiment 61, wherein the antibody comprises a VH comprising SEQ ID NO: 10 and a VL comprising SEQ ID NO:13.

88. The method of embodiment 61, wherein the antibody comprises a VH comprising SEQ ID NO: 10 and a VL comprising SEQ ID NO:14.

89. The method of embodiment 61, wherein the antibody comprises a VH comprising SEQ ID NO: 10 and a VL comprising SEQ ID NO:15.

90. The method of embodiment 61, wherein the antibody comprises a VH comprising SEQ ID NO: 10 and a VL comprising SEQ ID NO:16.

91. The method of embodiment 61, wherein the antibody comprises a VH comprising SEQ ID NO: 11 and a VL comprising SEQ ID NO:13.

92. The method of embodiment 61, wherein the antibody comprises a VH comprising SEQ ID NO: 11 and a VL comprising SEQ ID NO:14.

93. The method of embodiment 61, wherein the antibody comprises a VH comprising SEQ ID NO: 11 and a VL comprising SEQ ID NO:15.

94. The method of embodiment 61, wherein the antibody comprises a VH comprising SEQ ID NO: 11 and a VL comprising SEQ ID NO:16.

95. The method of embodiment 61, wherein the antibody comprises a VH comprising SEQ ID NO: 11.

96. The method of embodiment 61, wherein the antibody comprises a VH comprising SEQ ID NO: 12 and a VL comprising SEQ ID NO:13.

97. The method of embodiment 61, wherein the antibody comprises a VH comprising SEQ ID NO: 12 and a VL comprising SEQ ID NO:14.

98. The method of embodiment 61, wherein the antibody comprises a VH comprising SEQ ID NO: 12 and a VL comprising SEQ ID NO:15.

99. The method of embodiment 61, wherein the antibody comprises a VH comprising SEQ ID NO: 12 and a VL comprising SEQ ID NO:16.

100. The method of any one of embodiments 70-99, comprising administering a therapeutically effective amount of an antibody which specifically binds to a human KIT receptor (SEQ ID NO:1).

101. A method of protecting against a mast cell related disorder of the nervous system in a subject, comprising administering to a subject in need thereof a therapeutically effective amount of an antibody which specifically binds to a human KIT receptor (SEQ ID NO: 1), or an antigen binding fragment thereof.

102. A method of protecting against an eosinophil related disorder of the nervous system in a subject, comprising administering to a subject in need thereof a therapeutically effective amount of an antibody which specifically binds to a human KIT receptor (SEQ ID NO: 1), or an antigen binding fragment thereof. 103. The method of embodiment 101 or 102, wherein the antibody is a bivalent monospecific antibody.

104. The method of embodiment 103, wherein the antibody is a humanized antibody.

105. The method of embodiment 104, wherein the antibody is a naked antibody.

106. The method of embodiment 103, wherein the antibody is a naked antibody.

107. The method of embodiment 101 or 102, wherein the antibody is a humanized antibody.

108. The method of embodiment 107, wherein the antibody is a naked antibody.

109. The method of embodiment 101 or 102, wherein the antibody is a naked antibody.

110. The method of any one of embodiments 101-109, comprising administering a therapeutically effective amount of an antibody which specifically binds to a human KIT receptor (SEQ ID NO:1).

111. The method of embodiment 101 or 102, wherein the antibody comprises a light chain variable region ("VL") comprising VL CDRs 1-3 comprising SEQ ID NOs: 2-4, respectively, and a heavy chain variable region ("VH") comprising VH CDRs 1-3 comprising SEQ ID NOs: 5-7, respectively.

112. The method of embodiment 111, wherein the antibody is a bivalent monospecific antibody.

113. The method of embodiment 112, wherein the antibody is a humanized antibody.

114. The method of embodiment 113, wherein the antibody is a naked antibody.

115. The method of embodiment 112, wherein the antibody is a naked antibody.

116. The method of embodiment 111, wherein the antibody is a humanized antibody.

117. The method of embodiment 116, wherein the antibody is a naked antibody.

118. The method of embodiment 111, wherein the antibody is a naked antibody.

119. The method of any one of embodiments 111-118, comprising administering a therapeutically effective amount of an antibody which specifically binds to a human KIT receptor (SEQ ID NO:1).

120. The method of embodiment 111, wherein the antibody comprises a VH comprising SEQ ID NO: 8.

121. The method of embodiment 111, wherein the antibody comprises a VH comprising SEQ ID NO: 9.

122. The method of embodiment 111, wherein the antibody comprises a VH comprising SEQ ID NO: 10.

123. The method of embodiment 111, wherein the antibody comprises a VH comprising SEQ ID NO: 11.

124. The method of embodiment 111, wherein the antibody comprises a VH comprising SEQ ID NO: 12.

125. The method of embodiment 111, wherein the antibody comprises a VL comprising SEQ ID NO: 13.

126. The method of embodiment 111, wherein the antibody comprises a VL comprising SEQ ID NO: 14.

127. The method of embodiment 111, wherein the antibody comprises a VL comprising SEQ ID NO: 15.

128. The method of embodiment 111, wherein the antibody comprises a VL comprising SEQ ID NO: 16.

129. The method of embodiment 111, wherein the antibody comprises a VH comprising SEQ ID NO: 8 and a VL comprising SEQ ID NO:13.

130. The method of embodiment 111, wherein the antibody comprises a VH comprising SEQ ID NO: 8 and a VL comprising SEQ ID NO:14.

131. The method of embodiment 111, wherein the antibody comprises a VH comprising SEQ ID NO: 8 and a VL comprising SEQ ID NO:15.

132. The method of embodiment 111, wherein the antibody comprises a VH comprising SEQ ID NO: 8 and a VL comprising SEQ ID NO:16.

133. The method of embodiment 111, wherein the antibody comprises a VH comprising SEQ ID NO: 9 and a VL comprising SEQ ID NO:13.

134. The method of embodiment 111, wherein the antibody comprises a VH comprising SEQ ID NO: 9 and a VL comprising SEQ ID NO:14.

135. The method of embodiment 111, wherein the antibody comprises a VH comprising SEQ ID NO: 9 and a VL comprising SEQ ID NO:15.

136. The method of embodiment 111, wherein the antibody comprises a VH comprising SEQ ID NO: 9 and a VL comprising SEQ ID NO:16.

137. The method of embodiment 111, wherein the antibody comprises a VH comprising SEQ ID NO: 10 and a VL comprising SEQ ID NO:13.

138. The method of embodiment 111, wherein the antibody comprises a VH comprising SEQ ID NO: 10 and a VL comprising SEQ ID NO:14.

139. The method of embodiment 111, wherein the antibody comprises a VH comprising SEQ ID NO: 10 and a VL comprising SEQ ID NO:15.

140. The method of embodiment 111, wherein the antibody comprises a VH comprising SEQ ID NO: 10 and a VL comprising SEQ ID NO:16.

141. The method of embodiment 111, wherein the antibody comprises a VH comprising SEQ ID NO: 11 and a VL comprising SEQ ID NO:13.

142. The method of embodiment 111, wherein the antibody comprises a VH comprising SEQ ID NO: 11 and a VL comprising SEQ ID NO:14.

143. The method of embodiment 111, wherein the antibody comprises a VH comprising SEQ ID NO: 11 and a VL comprising SEQ ID NO:15.

144. The method of embodiment 111, wherein the antibody comprises a VH comprising SEQ ID NO: 11 and a VL comprising SEQ ID NO:16.

145. The method of embodiment 111, wherein the antibody comprises a VH comprising SEQ ID NO: 11.

146. The method of embodiment 111, wherein the antibody comprises a VH comprising SEQ ID NO: 12 and a VL comprising SEQ ID NO:13.

147. The method of embodiment 111, wherein the antibody comprises a VH comprising SEQ ID NO: 12 and a VL comprising SEQ ID NO:14.

148. The method of embodiment 111, wherein the antibody comprises a VH comprising SEQ ID NO: 12 and a VL comprising SEQ ID NO:15.

149. The method of embodiment 111, wherein the antibody comprises a VH comprising SEQ ID NO: 12 and a VL comprising SEQ ID NO:16.

150. The method of any one of embodiments 120-149, comprising administering a therapeutically effective amount of an antibody which specifically binds to a human KIT receptor (SEQ ID NO:1).

151. A method of treating neurofibromatosis (NF) in a subject, comprising administering to a subject in need thereof a therapeutically effective amount of an antibody which specifically binds to a human KIT receptor (SEQ ID NO: 1), or an antigen binding fragment thereof.

152. The method of embodiment 151, wherein the antibody is a bivalent monospecific antibody.

153. The method of embodiment 152, wherein the antibody is a humanized antibody.

154. The method of embodiment 153, wherein the antibody is a naked antibody.

155. The method of embodiment 152, wherein the antibody is a naked antibody.

156. The method of embodiment 151, wherein the antibody is a humanized antibody.

157. The method of embodiment 157, wherein the antibody is a naked antibody.

158. The method of embodiment 151, wherein the antibody is a naked antibody

159. The method of any one of embodiments 151-158, comprising administering a therapeutically effective amount of an antibody which specifically binds to a human KIT receptor (SEQ ID NO:1).

160. The method of embodiment 151, wherein the antibody comprises a light chain variable region ("VL") comprising VL CDRs 1-3 comprising SEQ ID NOs: 2-4, respectively, and a heavy chain variable region ("VH") comprising VH CDRs 1-3 comprising SEQ ID NOs: 5-7, respectively.

161. The method of embodiment 160, wherein the antibody is a bivalent monospecific antibody.

162. The method of embodiment 161, wherein the antibody is a humanized antibody.

163. The method of embodiment 162, wherein the antibody is a naked antibody.

164. The method of embodiment 161, wherein the antibody is a naked antibody.

165. The method of embodiment 160, wherein the antibody is a humanized antibody.

166. The method of embodiment 165, wherein the antibody is a naked antibody.

167. The method of embodiment 160, wherein the antibody is a naked antibody

168. The method of any one of embodiments 160-167, comprising administering a therapeutically effective amount of an antibody which specifically binds to a human KIT receptor (SEQ ID NO:1).

169. The method of embodiment 160, wherein the antibody comprises a VH comprising SEQ ID NO: 8.

170. The method of embodiment 160, wherein the antibody comprises a VH comprising SEQ ID NO: 9.

171. The method of embodiment 160, wherein the antibody comprises a VH comprising SEQ ID NO: 10.

172. The method of embodiment 160, wherein the antibody comprises a VH comprising SEQ ID NO: 11.

173. The method of embodiment 160, wherein the antibody comprises a VH comprising SEQ ID NO: 12.

174. The method of embodiment 160, wherein the antibody comprises a VL comprising SEQ ID NO: 13.

175. The method of embodiment 160, wherein the antibody comprises a VL comprising SEQ ID NO: 14.

176. The method of embodiment 160, wherein the antibody comprises a VL comprising SEQ ID NO: 15.

177. The method of embodiment 160, wherein the antibody comprises a VL comprising SEQ ID NO: 16.

178. The method of embodiment 160, wherein the antibody comprises a VH comprising SEQ ID NO: 8 and a VL comprising SEQ ID NO:13.

179. The method of embodiment 160, wherein the antibody comprises a VH comprising SEQ ID NO: 8 and a VL comprising SEQ ID NO:14.

180. The method of embodiment 160, wherein the antibody comprises a VH comprising SEQ ID NO: 8 and a VL comprising SEQ ID NO:15.

181. The method of embodiment 160, wherein the antibody comprises a VH comprising SEQ ID NO: 8 and a VL comprising SEQ ID NO:16.

182. The method of embodiment 160, wherein the antibody comprises a VH comprising SEQ ID NO: 9 and a VL comprising SEQ ID NO:13.

183. The method of embodiment 160, wherein the antibody comprises a VH comprising SEQ ID NO: 9 and a VL comprising SEQ ID NO:14.

184. The method of embodiment 160, wherein the antibody comprises a VH comprising SEQ ID NO: 9 and a VL comprising SEQ ID NO:15.

185. The method of embodiment 160, wherein the antibody comprises a VH comprising SEQ ID NO: 9 and a VL comprising SEQ ID NO:16.

186. The method of embodiment 160, wherein the antibody comprises a VH comprising SEQ ID NO: 10 and a VL comprising SEQ ID NO:13.

187. The method of embodiment 160, wherein the antibody comprises a VH comprising SEQ ID NO: 10 and a VL comprising SEQ ID NO:14.

188. The method of embodiment 160, wherein the antibody comprises a VH comprising SEQ ID NO: 10 and a VL comprising SEQ ID NO:15.

189. The method of embodiment 160, wherein the antibody comprises a VH comprising SEQ ID NO: 10 and a VL comprising SEQ ID NO:16.

190. The method of embodiment 160, wherein the antibody comprises a VH comprising SEQ ID NO: 11 and a VL comprising SEQ ID NO:13.

191. The method of embodiment 160, wherein the antibody comprises a VH comprising SEQ ID NO: 11 and a VL comprising SEQ ID NO:14.

192. The method of embodiment 160, wherein the antibody comprises a VH comprising SEQ ID NO: 11 and a VL comprising SEQ ID NO:15.

193. The method of embodiment 160, wherein the antibody comprises a VH comprising SEQ ID NO: 11 and a VL comprising SEQ ID NO:16.

194. The method of embodiment 160, wherein the antibody comprises a VH comprising SEQ ID NO: 11.

195. The method of embodiment 160, wherein the antibody comprises a VH comprising SEQ ID NO: 12 and a VL comprising SEQ ID NO:13.

196. The method of embodiment 160, wherein the antibody comprises a VH comprising SEQ ID NO: 12 and a VL comprising SEQ ID NO:14.

197. The method of embodiment 160, wherein the antibody comprises a VH comprising SEQ ID NO: 12 and a VL comprising SEQ ID NO:15.

198. The method of embodiment 160, wherein the antibody comprises a VH comprising SEQ ID NO: 12 and a VL comprising SEQ ID NO:16.

199. The method of any one of embodiments 169-198, comprising administering a therapeutically effective amount of an antibody which specifically binds to a human KIT receptor (SEQ ID NO:1).

200. The method of any one of embodiment 151-199, wherein the NF is NF1.

201. The method of any one of embodiment 151-199, wherein the NF is NF2.

202. The method of any one of embodiments 151-199, wherein the NF is Schwannomatosis.

203. A method of managing NF in a subject, comprising administering to a subject in need thereof a therapeutically effective amount of an antibody which specifically binds to a human KIT receptor (SEQ ID NO: 1), or an antigen binding fragment thereof.

204. The method of embodiment 203, wherein the antibody is a bivalent monospecific antibody.

205. The method of embodiment 204, wherein the antibody is a humanized antibody.

206. The method of embodiment 203, wherein the antibody is a naked antibody.

207. The method of embodiment 204, wherein the antibody is a naked antibody.

208. The method of embodiment 203, wherein the antibody is a humanized antibody.

209. The method of embodiment 208, wherein the antibody is a naked antibody.

210. The method of embodiment 203, wherein the antibody is a naked antibody

211. The method of any one of embodiments 203-210, comprising administering a therapeutically effective amount of an antibody which specifically binds to a human KIT receptor (SEQ ID NO:1).

212. The method of embodiment 203, wherein the antibody comprises a light chain variable region ("VL") comprising VL CDRs 1-3 comprising SEQ ID NOs: 2-4, respectively, and a heavy chain variable region ("VH") comprising VH CDRs 1-3 comprising SEQ ID NOs: 5-7, respectively.

213. The method of embodiment 212, wherein the antibody is a bivalent monospecific antibody.

214. The method of embodiment 213, wherein the antibody is a humanized antibody.

215. The method of embodiment 212, wherein the antibody is a naked antibody.

216. The method of embodiment 213, wherein the antibody is a naked antibody.

217. The method of embodiment 212, wherein the antibody is a humanized antibody.

218. The method of embodiment 217, wherein the antibody is a naked antibody.

219. The method of embodiment 212, wherein the antibody is a naked antibody.

220. The method of any one of embodiments 212-219, comprising administering a therapeutically effective amount of an antibody which specifically binds to a human KIT receptor (SEQ ID NO:1).

221. The method of embodiment 212, wherein the antibody comprises a VH comprising SEQ ID NO: 8.

222. The method of embodiment 212, wherein the antibody comprises a VH comprising SEQ ID NO: 9.

223. The method of embodiment 212, wherein the antibody comprises a VH comprising SEQ ID NO: 10.

224. The method of embodiment 212, wherein the antibody comprises a VH comprising SEQ ID NO: 11.

225. The method of embodiment 212, wherein the antibody comprises a VH comprising SEQ ID NO: 12.

226. The method of embodiment 212, wherein the antibody comprises a VL comprising SEQ ID NO: 13.

227. The method of embodiment 212, wherein the antibody comprises a VL comprising SEQ ID NO: 14.

228. The method of embodiment 212, wherein the antibody comprises a VL comprising SEQ ID NO: 15.

229. The method of embodiment 212, wherein the antibody comprises a VL comprising SEQ ID NO: 16.

230. The method of embodiment 212, wherein the antibody comprises a VH comprising SEQ ID NO: 8 and a VL comprising SEQ ID NO:13.

231. The method of embodiment 212, wherein the antibody comprises a VH comprising SEQ ID NO: 8 and a VL comprising SEQ ID NO:14.

232. The method of embodiment 212, wherein the antibody comprises a VH comprising SEQ ID NO: 8 and a VL comprising SEQ ID NO:15.

233. The method of embodiment 212, wherein the antibody comprises a VH comprising SEQ ID NO: 8 and a VL comprising SEQ ID NO:16.

234. The method of embodiment 212, wherein the antibody comprises a VH comprising SEQ ID NO: 9 and a VL comprising SEQ ID NO:13.

235. The method of embodiment 212, wherein the antibody comprises a VH comprising SEQ ID NO: 9 and a VL comprising SEQ ID NO:14.

236. The method of embodiment 212, wherein the antibody comprises a VH comprising SEQ ID NO: 9 and a VL comprising SEQ ID NO:15.

237. The method of embodiment 212, wherein the antibody comprises a VH comprising SEQ ID NO: 9 and a VL comprising SEQ ID NO:16.

238. The method of embodiment 212, wherein the antibody comprises a VH comprising SEQ ID NO: 10 and a VL comprising SEQ ID NO:13.

239. The method of embodiment 212, wherein the antibody comprises a VH comprising SEQ ID NO: 10 and a VL comprising SEQ ID NO:14.

240. The method of embodiment 212, wherein the antibody comprises a VH comprising SEQ ID NO: 10 and a VL comprising SEQ ID NO:15.

241. The method of embodiment 212, wherein the antibody comprises a VH comprising SEQ ID NO: 10 and a VL comprising SEQ ID NO:16.

242. The method of embodiment 212, wherein the antibody comprises a VH comprising SEQ ID NO: 11 and a VL comprising SEQ ID NO:13.

243. The method of embodiment 212, wherein the antibody comprises a VH comprising SEQ ID NO: 11 and a VL comprising SEQ ID NO:14.

244. The method of embodiment 212, wherein the antibody comprises a VH comprising SEQ ID NO: 11 and a VL comprising SEQ ID NO:15.

245. The method of embodiment 212, wherein the antibody comprises a VH comprising SEQ ID NO: 11 and a VL comprising SEQ ID NO:16.

246. The method of embodiment 212, wherein the antibody comprises a VH comprising SEQ ID NO: 11.

247. The method of embodiment 212, wherein the antibody comprises a VH comprising SEQ ID NO: 12 and a VL comprising SEQ ID NO:13.

248. The method of embodiment 212, wherein the antibody comprises a VH comprising SEQ ID NO: 12 and a VL comprising SEQ ID NO:14.

249. The method of embodiment 212, wherein the antibody comprises a VH comprising SEQ ID NO: 12 and a VL comprising SEQ ID NO:15.

250. The method of embodiment 212, wherein the antibody comprises a VH comprising SEQ ID NO: 12 and a VL comprising SEQ ID NO:16.

251. The method of any one of embodiments 221-250, comprising administering a therapeutically effective amount of an antibody which specifically binds to a human KIT receptor (SEQ ID NO:1).

252. The method of any one of embodiments 203-251, wherein the NF is NF1.

253. The method of any one of embodiments 203-251, wherein the NF is NF2.

254. The method of any one of embodiments 203-251, wherein the NF is Schwannomatosis.

255. A method of protecting against NF in a subject, comprising administering to a subject in need thereof a therapeutically effective amount of an antibody which specifically binds to a human KIT receptor (SEQ ID NO: 1), or an antigen binding fragment thereof.

256. The method of embodiment 255, wherein the antibody is a bivalent monospecific antibody.

257. The method of embodiment 256, wherein the antibody is a humanized antibody.

258. The method of embodiment 257, wherein the antibody is a naked antibody.

259. The method of embodiment 256, wherein the antibody is a naked antibody.

260. The method of embodiment 255, wherein the antibody is a humanized antibody.

261. The method of embodiment 260, wherein the antibody is a naked antibody.

262. The method of embodiment 255, wherein the antibody is a naked antibody.

263. The method of any one of embodiments 255-262, comprising administering a therapeutically effective amount of an antibody which specifically binds to a human KIT receptor (SEQ ID NO:1).

264. The method of embodiment 255, wherein the antibody comprises a light chain variable region ("VL") comprising VL CDRs 1-3 comprising SEQ ID NOs: 2-4, respectively, and a heavy chain variable region ("VH") comprising VH CDRs 1-3 comprising SEQ ID NOs: 5-7, respectively.

265. The method of embodiment 264, wherein the antibody is a bivalent monospecific antibody.

266. The method of embodiment 265, wherein the antibody is a humanized antibody.

267. The method of embodiment 266, wherein the antibody is a naked antibody.

268. The method of embodiment 265, wherein the antibody is a naked antibody.

269. The method of embodiment 264, wherein the antibody is a humanized antibody.

270. The method of embodiment 269, wherein the antibody is a naked antibody.

271. The method of embodiment 264, wherein the antibody is a naked antibody.

272. The method of any one of embodiments 264-271, comprising administering a therapeutically effective amount of an antibody which specifically binds to a human KIT receptor (SEQ ID NO:1).

273. The method of embodiment 264, wherein the antibody comprises a VH comprising SEQ ID NO: 8.

274. The method of embodiment 264, wherein the antibody comprises a VH comprising SEQ ID NO: 9.

275. The method of embodiment 264, wherein the antibody comprises a VH comprising SEQ ID NO: 10.

276. The method of embodiment 264, wherein the antibody comprises a VH comprising SEQ ID NO: 11.

277. The method of embodiment 264, wherein the antibody comprises a VH comprising SEQ ID NO: 12.

278. The method of embodiment 264, wherein the antibody comprises a VL comprising SEQ ID NO: 13.

279. The method of embodiment 264, wherein the antibody comprises a VL comprising SEQ ID NO: 14.

280. The method of embodiment 264, wherein the antibody comprises a VL comprising SEQ ID NO: 15.

281. The method of embodiment 264, wherein the antibody comprises a VL comprising SEQ ID NO: 16.

282. The method of embodiment 264, wherein the antibody comprises a VH comprising SEQ ID NO: 8 and a VL comprising SEQ ID NO:13.

283. The method of embodiment 264, wherein the antibody comprises a VH comprising SEQ ID NO: 8 and a VL comprising SEQ ID NO:14.

284. The method of embodiment 264, wherein the antibody comprises a VH comprising SEQ ID NO: 8 and a VL comprising SEQ ID NO:15.

285. The method of embodiment 264, wherein the antibody comprises a VH comprising SEQ ID NO: 8 and a VL comprising SEQ ID NO:16.

286. The method of embodiment 264, wherein the antibody comprises a VH comprising SEQ ID NO: 9 and a VL comprising SEQ ID NO:13.

287. The method of embodiment 264, wherein the antibody comprises a VH comprising SEQ ID NO: 9 and a VL comprising SEQ ID NO:14.

288. The method of embodiment 264, wherein the antibody comprises a VH comprising SEQ ID NO: 9 and a VL comprising SEQ ID NO:15.

289. The method of embodiment 264, wherein the antibody comprises a VH comprising SEQ ID NO: 9 and a VL comprising SEQ ID NO:16.

290. The method of embodiment 264, wherein the antibody comprises a VH comprising SEQ ID NO: 10 and a VL comprising SEQ ID NO:13.

291. The method of embodiment 264, wherein the antibody comprises a VH comprising SEQ ID NO: 10 and a VL comprising SEQ ID NO:14.

292. The method of embodiment 264, wherein the antibody comprises a VH comprising SEQ ID NO: 10 and a VL comprising SEQ ID NO:15.

293. The method of embodiment 264, wherein the antibody comprises a VH comprising SEQ ID NO: 10 and a VL comprising SEQ ID NO:16.

294. The method of embodiment 264, wherein the antibody comprises a VH comprising SEQ ID NO: 11 and a VL comprising SEQ ID NO:13.

295. The method of embodiment 264, wherein the antibody comprises a VH comprising SEQ ID NO: 11 and a VL comprising SEQ ID NO:14.

296. The method of embodiment 264, wherein the antibody comprises a VH comprising SEQ ID NO: 11 and a VL comprising SEQ ID NO:15.

297. The method of embodiment 264, wherein the antibody comprises a VH comprising SEQ ID NO: 11 and a VL comprising SEQ ID NO:16.

298. The method of embodiment 264, wherein the antibody comprises a VH comprising SEQ ID NO: 11.

299. The method of embodiment 264, wherein the antibody comprises a VH comprising SEQ ID NO: 12 and a VL comprising SEQ ID NO:13.

300. The method of embodiment 264, wherein the antibody comprises a VH comprising SEQ ID NO: 12 and a VL comprising SEQ ID NO:14.

301. The method of embodiment 264, wherein the antibody comprises a VH comprising SEQ ID NO: 12 and a VL comprising SEQ ID NO:15.

302. The method of embodiment 264, wherein the antibody comprises a VH comprising SEQ ID NO: 12 and a VL comprising SEQ ID NO:16.

303. The method of any one of embodiments 273-302, comprising administering a therapeutically effective amount of an antibody which specifically binds to a human KIT receptor (SEQ ID NO:1).

304. The method of any one of embodiments 255-303, wherein the NF is NF1.

305. The method any one of embodiments 255-303, wherein the NF is NF2.

306. The method any one of embodiments 255-303, wherein the NF is Schwannomatosis.

307. A method of inhibiting growth of neurofibromas in a subject, comprising administering to a subject diagnosed with NF a therapeutically effective amount of an antibody which specifically binds to a human KIT receptor (SEQ ID NO: 1), or an antigen binding fragment thereof.

308. The method of embodiment 307, wherein the antibody is a bivalent monospecific antibody.

309. The method of embodiment 308, wherein the antibody is a humanized antibody.

310. The method of embodiment 309, wherein the antibody is a naked antibody.

311. The method of embodiment 308, wherein the antibody is a naked antibody.

312. The method of embodiment 307, wherein the antibody is a humanized antibody.

313. The method of embodiment 312, wherein the antibody is a naked antibody.

314. The method of embodiment 307, wherein the antibody is a naked antibody.

315. The method of any one of embodiments 307-314, comprising administering a therapeutically effective amount of an antibody which specifically binds to a human KIT receptor (SEQ ID NO:1).

316. The method of embodiment 307, wherein the antibody comprises a light chain variable region ("VL") comprising VL CDRs 1-3 comprising SEQ ID NOs: 2-4, respectively, and a heavy chain variable region ("VH") comprising VH CDRs 1-3 comprising SEQ ID NOs: 5-7, respectively.

317. The method of embodiment 316, wherein the antibody is a bivalent monospecific antibody.

318. The method of embodiment 317, wherein the antibody is a humanized antibody.

319. The method of embodiment 318, wherein the antibody is a naked antibody.

320. The method of embodiment 317, wherein the antibody is a naked antibody.

321. The method of embodiment 316, wherein the antibody is a humanized antibody.

322. The method of embodiment 321, wherein the antibody is a naked antibody.

323. The method of embodiment 316, wherein the antibody is a naked antibody.

324. The method of any one of embodiments 316-323, comprising administering a therapeutically effective amount of an antibody which specifically binds to a human KIT receptor (SEQ ID NO:1).

325. The method of embodiment 316, wherein the antibody comprises a VH comprising SEQ ID NO: 8.

326. The method of embodiment 316, wherein the antibody comprises a VH comprising SEQ ID NO: 9.

327. The method of embodiment 316, wherein the antibody comprises a VH comprising SEQ ID NO: 10.

328. The method of embodiment 316, wherein the antibody comprises a VH comprising SEQ ID NO: 11.

329. The method of embodiment 316, wherein the antibody comprises a VH comprising SEQ ID NO: 12.

330. The method of embodiment 316, wherein the antibody comprises a VL comprising SEQ ID NO: 13.

331. The method of embodiment 316, wherein the antibody comprises a VL comprising SEQ ID NO: 14.

332. The method of embodiment 316, wherein the antibody comprises a VL comprising SEQ ID NO: 15.

333. The method of embodiment 316, wherein the antibody comprises a VL comprising SEQ ID NO: 16.

334. The method of embodiment 316, wherein the antibody comprises a VH comprising SEQ ID NO: 8 and a VL comprising SEQ ID NO:13.

335. The method of embodiment 316, wherein the antibody comprises a VH comprising SEQ ID NO: 8 and a VL comprising SEQ ID NO:14.

336. The method of embodiment 316, wherein the antibody comprises a VH comprising SEQ ID NO: 8 and a VL comprising SEQ ID NO:15.

337. The method of embodiment 316, wherein the antibody comprises a VH comprising SEQ ID NO: 8 and a VL comprising SEQ ID NO:16.

338. The method of embodiment 316, wherein the antibody comprises a VH comprising SEQ ID NO: 9 and a VL comprising SEQ ID NO:13.

339. The method of embodiment 316, wherein the antibody comprises a VH comprising SEQ ID NO: 9 and a VL comprising SEQ ID NO:14.

340. The method of embodiment 316, wherein the antibody comprises a VH comprising SEQ ID NO: 9 and a VL comprising SEQ ID NO:15.

341. The method of embodiment 316, wherein the antibody comprises a VH comprising SEQ ID NO: 9 and a VL comprising SEQ ID NO:16.

342. The method of embodiment 316, wherein the antibody comprises a VH comprising SEQ ID NO: 10 and a VL comprising SEQ ID NO:13.

343. The method of embodiment 316, wherein the antibody comprises a VH comprising SEQ ID NO: 10 and a VL comprising SEQ ID NO:14.

344. The method of embodiment 316, wherein the antibody comprises a VH comprising SEQ ID NO: 10 and a VL comprising SEQ ID NO:15.

345. The method of embodiment 316, wherein the antibody comprises a VH comprising SEQ ID NO: 10 and a VL comprising SEQ ID NO:16.

346. The method of embodiment 316, wherein the antibody comprises a VH comprising SEQ ID NO: 11 and a VL comprising SEQ ID NO:13.

347. The method of embodiment 316, wherein the antibody comprises a VH comprising SEQ ID NO: 11 and a VL comprising SEQ ID NO:14.

348. The method of embodiment 316, wherein the antibody comprises a VH comprising SEQ ID NO: 11 and a VL comprising SEQ ID NO:15.
349. The method of embodiment 316, wherein the antibody comprises a VH comprising SEQ ID NO: 11 and a VL comprising SEQ ID NO:16.
350. The method of embodiment 316, wherein the antibody comprises a VH comprising SEQ ID NO: 11.
351. The method of embodiment 316, wherein the antibody comprises a VH comprising SEQ ID NO: 12 and a VL comprising SEQ ID NO:13.
352. The method of embodiment 316, wherein the antibody comprises a VH comprising SEQ ID NO: 12 and a VL comprising SEQ ID NO:14.
353. The method of embodiment 316, wherein the antibody comprises a VH comprising SEQ ID NO: 12 and a VL comprising SEQ ID NO:15.
354. The method of embodiment 316, wherein the antibody comprises a VH comprising SEQ ID NO: 12 and a VL comprising SEQ ID NO:16.
355. The method of any one of embodiments 325-354, comprising administering a therapeutically effective amount of an antibody which specifically binds to a human KIT receptor (SEQ ID NO:1).
356. The method of any one of embodiments 307-355, wherein the neurofibromas comprise external neurofibromas.
357. The method of any one of embodiments 307-355, wherein the neurofibromas comprise internal neurofibromas.
358. The method of any one of embodiments 307-355, wherein the neurofibromas comprise dermal neurofibromas.
359. The method of any one of embodiments 307-355, wherein the neurofibromas comprise cutaneous neurofibromas.
360. The method of any one of embodiments 307-355, wherein the neurofibromas comprise plexiform neurofibromas.
361. A method of treating neuromyelitis optica (NMO) in a subject, comprising administering to a subject in need thereof a therapeutically effective amount of an antibody which specifically binds to a human KIT receptor (SEQ ID NO: 1), or an antigen binding fragment thereof.
362. The method of embodiment 361, wherein the antibody is a bivalent monospecific antibody.
363. The method of embodiment 362, wherein the antibody is a humanized antibody.
364. The method of embodiment 363, wherein the antibody is a naked antibody.
365. The method of embodiment 362, wherein the antibody is a naked antibody.
366. The method of embodiment 361, wherein the antibody is a humanized antibody.
367. The method of embodiment 366, wherein the antibody is a naked antibody.
368. The method of embodiment 361, wherein the antibody is a naked antibody.
369. The method of any one of embodiments 361-368, comprising administering a therapeutically effective amount of an antibody which specifically binds to a human KIT receptor (SEQ ID NO:1).
370. The method of embodiment 361, wherein the antibody comprises a light chain variable region ("VL") comprising VL CDRs 1-3 comprising SEQ ID NOs: 2-4, respectively, and a heavy chain variable region ("VH") comprising VH CDRs 1-3 comprising SEQ ID NOs: 5-7, respectively.
371. The method of embodiment 370, wherein the antibody is a bivalent monospecific antibody.
372. The method of embodiment 371, wherein the antibody is a humanized antibody.
373. The method of embodiment 372, wherein the antibody is a naked antibody.
374. The method of embodiment 371, wherein the antibody is a naked antibody.
375. The method of embodiment 370, wherein the antibody is a humanized antibody.
376. The method of embodiment 375, wherein the antibody is a naked antibody.
377. The method of embodiment 370, wherein the antibody is a naked antibody.
378. The method of any one of embodiments 370-377, comprising administering a therapeutically effective amount of an antibody which specifically binds to a human KIT receptor (SEQ ID NO:1).
379. The method of embodiment 370, wherein the antibody comprises a VH comprising SEQ ID NO: 8.
380. The method of embodiment 370, wherein the antibody comprises a VH comprising SEQ ID NO: 9.
381. The method of embodiment 370, wherein the antibody comprises a VH comprising SEQ ID NO: 10.
382. The method of embodiment 370, wherein the antibody comprises a VH comprising SEQ ID NO: 11.
383. The method of embodiment 370, wherein the antibody comprises a VH comprising SEQ ID NO: 12.
384. The method of embodiment 370, wherein the antibody comprises a VL comprising SEQ ID NO: 13.
385. The method of embodiment 370, wherein the antibody comprises a VL comprising SEQ ID NO: 14.
386. The method of embodiment 370, wherein the antibody comprises a VL comprising SEQ ID NO: 15.
387. The method of embodiment 370, wherein the antibody comprises a VL comprising SEQ ID NO: 16.
388. The method of embodiment 370, wherein the antibody comprises a VH comprising SEQ ID NO: 8 and a VL comprising SEQ ID NO:13.
389. The method of embodiment 370, wherein the antibody comprises a VH comprising SEQ ID NO: 8 and a VL comprising SEQ ID NO:14.
390. The method of embodiment 370, wherein the antibody comprises a VH comprising SEQ ID NO: 8 and a VL comprising SEQ ID NO:15.
391. The method of embodiment 370, wherein the antibody comprises a VH comprising SEQ ID NO: 8 and a VL comprising SEQ ID NO:16.
392. The method of embodiment 370, wherein the antibody comprises a VH comprising SEQ ID NO: 9 and a VL comprising SEQ ID NO:13.
393. The method of embodiment 370, wherein the antibody comprises a VH comprising SEQ ID NO: 9 and a VL comprising SEQ ID NO:14.
394. The method of embodiment 370, wherein the antibody comprises a VH comprising SEQ ID NO: 9 and a VL comprising SEQ ID NO:15.
395. The method of embodiment 370, wherein the antibody comprises a VH comprising SEQ ID NO: 9 and a VL comprising SEQ ID NO:16.
396. The method of embodiment 370, wherein the antibody comprises a VH comprising SEQ ID NO: 10 and a VL comprising SEQ ID NO:13.
397. The method of embodiment 370, wherein the antibody comprises a VH comprising SEQ ID NO: 10 and a VL comprising SEQ ID NO:14.
398. The method of embodiment 370, wherein the antibody comprises a VH comprising SEQ ID NO: 10 and a VL comprising SEQ ID NO:15.

399. The method of embodiment 370, wherein the antibody comprises a VH comprising SEQ ID NO: 10 and a VL comprising SEQ ID NO:16.

400. The method of embodiment 370, wherein the antibody comprises a VH comprising SEQ ID NO: 11 and a VL comprising SEQ ID NO:13.

401. The method of embodiment 370, wherein the antibody comprises a VH comprising SEQ ID NO: 11 and a VL comprising SEQ ID NO:14.

402. The method of embodiment 370, wherein the antibody comprises a VH comprising SEQ ID NO: 11 and a VL comprising SEQ ID NO:15.

403. The method of embodiment 370, wherein the antibody comprises a VH comprising SEQ ID NO: 11 and a VL comprising SEQ ID NO:16.

404. The method of embodiment 370, wherein the antibody comprises a VH comprising SEQ ID NO: 11.

405. The method of embodiment 370, wherein the antibody comprises a VH comprising SEQ ID NO: 12 and a VL comprising SEQ ID NO:13.

406. The method of embodiment 370, wherein the antibody comprises a VH comprising SEQ ID NO: 12 and a VL comprising SEQ ID NO:14.

407. The method of embodiment 370, wherein the antibody comprises a VH comprising SEQ ID NO: 12 and a VL comprising SEQ ID NO:15.

408. The method of embodiment 370, wherein the antibody comprises a VH comprising SEQ ID NO: 12 and a VL comprising SEQ ID NO:16.

409. The method of any one of embodiments 379-408, comprising administering a therapeutically effective amount of an antibody which specifically binds to a human KIT receptor (SEQ ID NO:1).

410. A method of managing NMO in a subject, comprising administering to a subject in need thereof a therapeutically effective amount of an antibody which specifically binds to a human KIT receptor (SEQ ID NO: 1), or an antigen binding fragment thereof.

411. The method of embodiment 410, wherein the antibody is a bivalent monospecific antibody.

412. The method of embodiment 411, wherein the antibody is a humanized antibody.

413. The method of embodiment 412, wherein the antibody is a naked antibody.

414. The method of embodiment 411, wherein the antibody is a naked antibody.

415. The method of embodiment 410, wherein the antibody is a humanized antibody.

416. The method of embodiment 415, wherein the antibody is a naked antibody.

417. The method of embodiment 410, wherein the antibody is a naked antibody.

418. The method of any one of embodiments 410-417, comprising administering a therapeutically effective amount of an antibody which specifically binds to a human KIT receptor (SEQ ID NO:1).

419. The method of embodiment 410, wherein the antibody comprises a light chain variable region ("VL") comprising VL CDRs 1-3 comprising SEQ ID NOs: 2-4, respectively, and a heavy chain variable region ("VH") comprising VH CDRs 1-3 comprising SEQ ID NOs: 5-7, respectively.

420. The method of embodiment 419, wherein the antibody is a bivalent monospecific antibody.

421. The method of embodiment 420, wherein the antibody is a humanized antibody.

422. The method of embodiment 421, wherein the antibody is a naked antibody.

423. The method of embodiment 420, wherein the antibody is a naked antibody.

424. The method of embodiment 419, wherein the antibody is a humanized antibody.

425. The method of embodiment 424, wherein the antibody is a naked antibody.

426. The method of embodiment 419, wherein the antibody is a naked antibody.

427. The method of any one of embodiments 419-426, comprising administering a therapeutically effective amount of an antibody which specifically binds to a human KIT receptor (SEQ ID NO:1).

428. The method of embodiment 419, wherein the antibody comprises a VH comprising SEQ ID NO: 8.

429. The method of embodiment 419, wherein the antibody comprises a VH comprising SEQ ID NO: 9.

430. The method of embodiment 419, wherein the antibody comprises a VH comprising SEQ ID NO: 10.

431. The method of embodiment 419, wherein the antibody comprises a VH comprising SEQ ID NO: 11.

432. The method of embodiment 419, wherein the antibody comprises a VH comprising SEQ ID NO: 12.

433. The method of embodiment 419, wherein the antibody comprises a VL comprising SEQ ID NO: 13.

434. The method of embodiment 419, wherein the antibody comprises a VL comprising SEQ ID NO: 14.

435. The method of embodiment 419, wherein the antibody comprises a VL comprising SEQ ID NO: 15.

436. The method of embodiment 419, wherein the antibody comprises a VL comprising SEQ ID NO: 16.

437. The method of embodiment 419, wherein the antibody comprises a VH comprising SEQ ID NO: 8 and a VL comprising SEQ ID NO:13.

438. The method of embodiment 419, wherein the antibody comprises a VH comprising SEQ ID NO: 8 and a VL comprising SEQ ID NO:14.

439. The method of embodiment 419, wherein the antibody comprises a VH comprising SEQ ID NO: 8 and a VL comprising SEQ ID NO:15.

440. The method of embodiment 419, wherein the antibody comprises a VH comprising SEQ ID NO: 8 and a VL comprising SEQ ID NO:16.

441. The method of embodiment 419, wherein the antibody comprises a VH comprising SEQ ID NO: 9 and a VL comprising SEQ ID NO:13.

442. The method of embodiment 419, wherein the antibody comprises a VH comprising SEQ ID NO: 9 and a VL comprising SEQ ID NO:14.

443. The method of embodiment 419, wherein the antibody comprises a VH comprising SEQ ID NO: 9 and a VL comprising SEQ ID NO:15.

444. The method of embodiment 419, wherein the antibody comprises a VH comprising SEQ ID NO: 9 and a VL comprising SEQ ID NO:16.

445. The method of embodiment 419, wherein the antibody comprises a VH comprising SEQ ID NO: 10 and a VL comprising SEQ ID NO:13.

446. The method of embodiment 419, wherein the antibody comprises a VH comprising SEQ ID NO: 10 and a VL comprising SEQ ID NO:14.

447. The method of embodiment 419, wherein the antibody comprises a VH comprising SEQ ID NO: 10 and a VL comprising SEQ ID NO:15.

448. The method of embodiment 419, wherein the antibody comprises a VH comprising SEQ ID NO: 10 and a VL comprising SEQ ID NO:16.

449. The method of embodiment 419, wherein the antibody comprises a VH comprising SEQ ID NO: 11 and a VL comprising SEQ ID NO:13.

450. The method of embodiment 419, wherein the antibody comprises a VH comprising SEQ ID NO: 11 and a VL comprising SEQ ID NO:14.

451. The method of embodiment 419, wherein the antibody comprises a VH comprising SEQ ID NO: 11 and a VL comprising SEQ ID NO:15.

452. The method of embodiment 419, wherein the antibody comprises a VH comprising SEQ ID NO: 11 and a VL comprising SEQ ID NO:16.

453. The method of embodiment 419, wherein the antibody comprises a VH comprising SEQ ID NO: 11.

454. The method of embodiment 419, wherein the antibody comprises a VH comprising SEQ ID NO: 12 and a VL comprising SEQ ID NO:13.

455. The method of embodiment 419, wherein the antibody comprises a VH comprising SEQ ID NO: 12 and a VL comprising SEQ ID NO:14.

456. The method of embodiment 419, wherein the antibody comprises a VH comprising SEQ ID NO: 12 and a VL comprising SEQ ID NO:15.

457. The method of embodiment 419, wherein the antibody comprises a VH comprising SEQ ID NO: 12 and a VL comprising SEQ ID NO:16.

458. The method of any one of embodiments 428-457, comprising administering a therapeutically effective amount of an antibody which specifically binds to a human KIT receptor (SEQ ID NO:1).

459. A method of protecting against NMO in a subject, comprising administering to a subject in need thereof a therapeutically effective amount of an antibody which specifically binds to a human KIT receptor (SEQ ID NO: 1), or an antigen binding fragment thereof.

460. The method of embodiment 459, wherein the antibody is a bivalent monospecific antibody.

461. The method of embodiment 460, wherein the antibody is a humanized antibody.

462. The method of embodiment 461, wherein the antibody is a naked antibody.

463. The method of embodiment 460, wherein the antibody is a naked antibody.

464. The method of embodiment 459, wherein the antibody is a humanized antibody.

465. The method of embodiment 464, wherein the antibody is a naked antibody.

466. The method of embodiment 459, wherein the antibody is a naked antibody.

467. The method of any one of embodiments 459-466, comprising administering a therapeutically effective amount of an antibody which specifically binds to a human KIT receptor (SEQ ID NO:1).

468. The method of embodiment 459, wherein the antibody comprises a light chain variable region ("VL") comprising VL CDRs 1-3 comprising SEQ ID NOs: 2-4, respectively, and a heavy chain variable region ("VH") comprising VH CDRs 1-3 comprising SEQ ID NOs: 5-7, respectively.

469. The method of embodiment 468, wherein the antibody is a bivalent monospecific antibody.

470. The method of embodiment 469, wherein the antibody is a humanized antibody.

471. The method of embodiment 470, wherein the antibody is a naked antibody.

472. The method of embodiment 469, wherein the antibody is a naked antibody.

473. The method of embodiment 468, wherein the antibody is a humanized antibody.

474. The method of embodiment 473, wherein the antibody is a naked antibody.

475. The method of embodiment 468, wherein the antibody is a naked antibody.

476. The method of any one of embodiments 468-475, comprising administering a therapeutically effective amount of an antibody which specifically binds to a human KIT receptor (SEQ ID NO:1).

477. The method of embodiment 468, wherein the antibody comprises a VH comprising SEQ ID NO: 8.

478. The method of embodiment 468, wherein the antibody comprises a VH comprising SEQ ID NO: 9.

479. The method of embodiment 468, wherein the antibody comprises a VH comprising SEQ ID NO: 10.

480. The method of embodiment 468, wherein the antibody comprises a VH comprising SEQ ID NO: 11.

481. The method of embodiment 468, wherein the antibody comprises a VH comprising SEQ ID NO: 12.

482. The method of embodiment 468, wherein the antibody comprises a VL comprising SEQ ID NO: 13.

483. The method of embodiment 468, wherein the antibody comprises a VL comprising SEQ ID NO: 14.

484. The method of embodiment 468, wherein the antibody comprises a VL comprising SEQ ID NO: 15.

485. The method of embodiment 468, wherein the antibody comprises a VL comprising SEQ ID NO: 16.

486. The method of embodiment 468, wherein the antibody comprises a VH comprising SEQ ID NO: 8 and a VL comprising SEQ ID NO:13.

487. The method of embodiment 468, wherein the antibody comprises a VH comprising SEQ ID NO: 8 and a VL comprising SEQ ID NO:14.

488. The method of embodiment 468, wherein the antibody comprises a VH comprising SEQ ID NO: 8 and a VL comprising SEQ ID NO:15.

489. The method of embodiment 468, wherein the antibody comprises a VH comprising SEQ ID NO: 8 and a VL comprising SEQ ID NO:16.

490. The method of embodiment 468, wherein the antibody comprises a VH comprising SEQ ID NO: 9 and a VL comprising SEQ ID NO:13.

491. The method of embodiment 468, wherein the antibody comprises a VH comprising SEQ ID NO: 9 and a VL comprising SEQ ID NO:14.

492. The method of embodiment 468, wherein the antibody comprises a VH comprising SEQ ID NO: 9 and a VL comprising SEQ ID NO:15.

493. The method of embodiment 468, wherein the antibody comprises a VH comprising SEQ ID NO: 9 and a VL comprising SEQ ID NO:16.

494. The method of embodiment 468, wherein the antibody comprises a VH comprising SEQ ID NO: 10 and a VL comprising SEQ ID NO:13.

495. The method of embodiment 468, wherein the antibody comprises a VH comprising SEQ ID NO: 10 and a VL comprising SEQ ID NO:14.

496. The method of embodiment 468, wherein the antibody comprises a VH comprising SEQ ID NO: 10 and a VL comprising SEQ ID NO:15.

497. The method of embodiment 468, wherein the antibody comprises a VH comprising SEQ ID NO: 10 and a VL comprising SEQ ID NO:16.

498. The method of embodiment 468, wherein the antibody comprises a VH comprising SEQ ID NO: 11 and a VL comprising SEQ ID NO:13.

499. The method of embodiment 468, wherein the antibody comprises a VH comprising SEQ ID NO: 11 and a VL comprising SEQ ID NO:14.

500. The method of embodiment 468, wherein the antibody comprises a VH comprising SEQ ID NO: 11 and a VL comprising SEQ ID NO:15.

501. The method of embodiment 468, wherein the antibody comprises a VH comprising SEQ ID NO: 11 and a VL comprising SEQ ID NO:16.

502. The method of embodiment 468, wherein the antibody comprises a VH comprising SEQ ID NO: 11.

503. The method of embodiment 468, wherein the antibody comprises a VH comprising SEQ ID NO: 12 and a VL comprising SEQ ID NO:13.

504. The method of embodiment 468, wherein the antibody comprises a VH comprising SEQ ID NO: 12 and a VL comprising SEQ ID NO:14.

505. The method of embodiment 468, wherein the antibody comprises a VH comprising SEQ ID NO: 12 and a VL comprising SEQ ID NO:15.

506. The method of embodiment 468, wherein the antibody comprises a VH comprising SEQ ID NO: 12 and a VL comprising SEQ ID NO:16.

507. The method of any one of embodiments 477-506, comprising administering a therapeutically effective amount of an antibody which specifically binds to a human KIT receptor (SEQ ID NO:1).

508. A method of treating a NMO spectrum disorder in a subject, comprising administering to a subject in need thereof a therapeutically effective amount of an antibody which specifically binds to a human KIT receptor (SEQ ID NO: 1), or an antigen binding fragment thereof.

509. The method of embodiment 508, wherein the antibody is a bivalent monospecific antibody.

510. The method of embodiment 509, wherein the antibody is a humanized antibody.

511. The method of embodiment 510, wherein the antibody is a naked antibody.

512. The method of embodiment 509, wherein the antibody is a naked antibody.

513. The method of embodiment 508, wherein the antibody is a humanized antibody.

514. The method of embodiment 513, wherein the antibody is a naked antibody.

515. The method of embodiment 508, wherein the antibody is a naked antibody.

516. The method of any one of embodiments 508-515, comprising administering a therapeutically effective amount of an antibody which specifically binds to a human KIT receptor (SEQ ID NO:1).

517. The method of embodiment 508, wherein the antibody comprises a light chain variable region ("VL") comprising VL CDRs 1-3 comprising SEQ ID NOs: 2-4, respectively, and a heavy chain variable region ("VH") comprising VH CDRs 1-3 comprising SEQ ID NOs: 5-7, respectively.

518. The method of embodiment 517, wherein the antibody is a bivalent monospecific antibody.

519. The method of embodiment 518, wherein the antibody is a humanized antibody.

520. The method of embodiment 519, wherein the antibody is a naked antibody.

521. The method of embodiment 518, wherein the antibody is a naked antibody.

522. The method of embodiment 517, wherein the antibody is a humanized antibody.

523. The method of embodiment 522, wherein the antibody is a naked antibody.

524. The method of embodiment 517, wherein the antibody is a naked antibody.

525. The method of any one of embodiments 517-524, comprising administering a therapeutically effective amount of an antibody which specifically binds to a human KIT receptor (SEQ ID NO:1).

526. The method of embodiment 517, wherein the antibody comprises a VH comprising SEQ ID NO: 8.

527. The method of embodiment 517, wherein the antibody comprises a VH comprising SEQ ID NO: 9.

528. The method of embodiment 517, wherein the antibody comprises a VH comprising SEQ ID NO: 10.

529. The method of embodiment 517, wherein the antibody comprises a VH comprising SEQ ID NO: 11.

530. The method of embodiment 517, wherein the antibody comprises a VH comprising SEQ ID NO: 12.

531. The method of embodiment 517, wherein the antibody comprises a VL comprising SEQ ID NO: 13.

532. The method of embodiment 517, wherein the antibody comprises a VL comprising SEQ ID NO: 14.

533. The method of embodiment 517, wherein the antibody comprises a VL comprising SEQ ID NO: 15.

534. The method of embodiment 517, wherein the antibody comprises a VL comprising SEQ ID NO: 16.

535. The method of embodiment 517, wherein the antibody comprises a VH comprising SEQ ID NO: 8 and a VL comprising SEQ ID NO:13.

536. The method of embodiment 517, wherein the antibody comprises a VH comprising SEQ ID NO: 8 and a VL comprising SEQ ID NO:14.

537. The method of embodiment 517, wherein the antibody comprises a VH comprising SEQ ID NO: 8 and a VL comprising SEQ ID NO:15.

538. The method of embodiment 517, wherein the antibody comprises a VH comprising SEQ ID NO: 8 and a VL comprising SEQ ID NO:16.

539. The method of embodiment 517, wherein the antibody comprises a VH comprising SEQ ID NO: 9 and a VL comprising SEQ ID NO:13.

540. The method of embodiment 517, wherein the antibody comprises a VH comprising SEQ ID NO: 9 and a VL comprising SEQ ID NO:14.

541. The method of embodiment 517, wherein the antibody comprises a VH comprising SEQ ID NO: 9 and a VL comprising SEQ ID NO:15.

542. The method of embodiment 517, wherein the antibody comprises a VH comprising SEQ ID NO: 9 and a VL comprising SEQ ID NO:16.

543. The method of embodiment 517, wherein the antibody comprises a VH comprising SEQ ID NO: 10 and a VL comprising SEQ ID NO:13.

544. The method of embodiment 517, wherein the antibody comprises a VH comprising SEQ ID NO: 10 and a VL comprising SEQ ID NO:14.

545. The method of embodiment 517, wherein the antibody comprises a VH comprising SEQ ID NO: 10 and a VL comprising SEQ ID NO:15.

546. The method of embodiment 517, wherein the antibody comprises a VH comprising SEQ ID NO: 10 and a VL comprising SEQ ID NO:16.

547. The method of embodiment 517, wherein the antibody comprises a VH comprising SEQ ID NO: 11 and a VL comprising SEQ ID NO:13.

548. The method of embodiment 517, wherein the antibody comprises a VH comprising SEQ ID NO: 11 and a VL comprising SEQ ID NO:14.

549. The method of embodiment 517, wherein the antibody comprises a VH comprising SEQ ID NO: 11 and a VL comprising SEQ ID NO:15.

550. The method of embodiment 517, wherein the antibody comprises a VH comprising SEQ ID NO: 11 and a VL comprising SEQ ID NO:16.

551. The method of embodiment 517, wherein the antibody comprises a VH comprising SEQ ID NO: 11.

552. The method of embodiment 517, wherein the antibody comprises a VH comprising SEQ ID NO: 12 and a VL comprising SEQ ID NO:13.

553. The method of embodiment 517, wherein the antibody comprises a VH comprising SEQ ID NO: 12 and a VL comprising SEQ ID NO:14.

554. The method of embodiment 517, wherein the antibody comprises a VH comprising SEQ ID NO: 12 and a VL comprising SEQ ID NO:15.

555. The method of embodiment 517, wherein the antibody comprises a VH comprising SEQ ID NO: 12 and a VL comprising SEQ ID NO:16.

556. The method of any one of embodiments 526-555, comprising administering a therapeutically effective amount of an antibody which specifically binds to a human KIT receptor (SEQ ID NO:1).

557. A method of managing a NMO spectrum disorder in a subject, comprising administering to a subject in need thereof a therapeutically effective amount of an antibody which specifically binds to a human KIT receptor (SEQ ID NO: 1), or an antigen binding fragment thereof.

558. The method of embodiment 557, wherein the antibody is a bivalent monospecific antibody.

559. The method of embodiment 558, wherein the antibody is a humanized antibody.

560. The method of embodiment 559, wherein the antibody is a naked antibody.

561. The method of embodiment 558, wherein the antibody is a naked antibody.

562. The method of embodiment 557, wherein the antibody is a humanized antibody.

563. The method of embodiment 562, wherein the antibody is a naked antibody.

564. The method of embodiment 557, wherein the antibody is a naked antibody.

565. The method of any one of embodiments 557-564, comprising administering a therapeutically effective amount of an antibody which specifically binds to a human KIT receptor (SEQ ID NO:1).

566. The method of embodiment 557, wherein the antibody comprises a light chain variable region ("VL") comprising VL CDRs 1-3 comprising SEQ ID NOs: 2-4, respectively, and a heavy chain variable region ("VH") comprising VH CDRs 1-3 comprising SEQ ID NOs: 5-7, respectively.

567. The method of embodiment 566, wherein the antibody is a bivalent monospecific antibody.

568. The method of embodiment 567, wherein the antibody is a humanized antibody.

569. The method of embodiment 568, wherein the antibody is a naked antibody.

570. The method of embodiment 567, wherein the antibody is a naked antibody.

571. The method of embodiment 566, wherein the antibody is a humanized antibody.

572. The method of embodiment 571, wherein the antibody is a naked antibody.

573. The method of embodiment 566, wherein the antibody is a naked antibody.

574. The method of any one of embodiments 566-573, comprising administering a therapeutically effective amount of an antibody which specifically binds to a human KIT receptor (SEQ ID NO:1).

575. The method of embodiment 566, wherein the antibody comprises a VH comprising SEQ ID NO: 8.

576. The method of embodiment 566, wherein the antibody comprises a VH comprising SEQ ID NO: 9.

577. The method of embodiment 566, wherein the antibody comprises a VH comprising SEQ ID NO: 10.

578. The method of embodiment 566, wherein the antibody comprises a VH comprising SEQ ID NO: 11.

579. The method of embodiment 566, wherein the antibody comprises a VH comprising SEQ ID NO: 12.

580. The method of embodiment 566, wherein the antibody comprises a VL comprising SEQ ID NO: 13.

581. The method of embodiment 566, wherein the antibody comprises a VL comprising SEQ ID NO: 14.

582. The method of embodiment 566, wherein the antibody comprises a VL comprising SEQ ID NO: 15.

583. The method of embodiment 566, wherein the antibody comprises a VL comprising SEQ ID NO: 16.

584. The method of embodiment 566, wherein the antibody comprises a VH comprising SEQ ID NO: 8 and a VL comprising SEQ ID NO:13.

585. The method of embodiment 566, wherein the antibody comprises a VH comprising SEQ ID NO: 8 and a VL comprising SEQ ID NO:14.

586. The method of embodiment 566, wherein the antibody comprises a VH comprising SEQ ID NO: 8 and a VL comprising SEQ ID NO:15.

587. The method of embodiment 566, wherein the antibody comprises a VH comprising SEQ ID NO: 8 and a VL comprising SEQ ID NO:16.

588. The method of embodiment 566, wherein the antibody comprises a VH comprising SEQ ID NO: 9 and a VL comprising SEQ ID NO:13.

589. The method of embodiment 566, wherein the antibody comprises a VH comprising SEQ ID NO: 9 and a VL comprising SEQ ID NO:14.

590. The method of embodiment 566, wherein the antibody comprises a VH comprising SEQ ID NO: 9 and a VL comprising SEQ ID NO:15.

591. The method of embodiment 566, wherein the antibody comprises a VH comprising SEQ ID NO: 9 and a VL comprising SEQ ID NO:16.

592. The method of embodiment 566, wherein the antibody comprises a VH comprising SEQ ID NO: 10 and a VL comprising SEQ ID NO:13.

593. The method of embodiment 566, wherein the antibody comprises a VH comprising SEQ ID NO: 10 and a VL comprising SEQ ID NO:14.

594. The method of embodiment 566, wherein the antibody comprises a VH comprising SEQ ID NO: 10 and a VL comprising SEQ ID NO:15.

595. The method of embodiment 566, wherein the antibody comprises a VH comprising SEQ ID NO: 10 and a VL comprising SEQ ID NO:16.

596. The method of embodiment 566, wherein the antibody comprises a VH comprising SEQ ID NO: 11 and a VL comprising SEQ ID NO:13.

597. The method of embodiment 566, wherein the antibody comprises a VH comprising SEQ ID NO: 11 and a VL comprising SEQ ID NO:14.

598. The method of embodiment 566, wherein the antibody comprises a VH comprising SEQ ID NO: 11 and a VL comprising SEQ ID NO:15.

599. The method of embodiment 566, wherein the antibody comprises a VH comprising SEQ ID NO: 11 and a VL comprising SEQ ID NO:16.

600. The method of embodiment 566, wherein the antibody comprises a VH comprising SEQ ID NO: 11.

601. The method of embodiment 566, wherein the antibody comprises a VH comprising SEQ ID NO: 12 and a VL comprising SEQ ID NO:13.

602. The method of embodiment 566, wherein the antibody comprises a VH comprising SEQ ID NO: 12 and a VL comprising SEQ ID NO:14.

603. The method of embodiment 566, wherein the antibody comprises a VH comprising SEQ ID NO: 12 and a VL comprising SEQ ID NO:15.

604. The method of embodiment 566, wherein the antibody comprises a VH comprising SEQ ID NO: 12 and a VL comprising SEQ ID NO:16.

605. The method of any one of embodiments 575-604, comprising administering a therapeutically effective amount of an antibody which specifically binds to a human KIT receptor (SEQ ID NO:1).

606. A method of protecting against a NMO spectrum disorder in a subject, comprising administering to a subject in need thereof a therapeutically effective amount of an antibody which specifically binds to a human KIT receptor (SEQ ID NO: 1), or an antigen binding fragment thereof.

607. The method of embodiment 606, wherein the antibody is a bivalent monospecific antibody.

608. The method of embodiment 607, wherein the antibody is a humanized antibody.

609. The method of embodiment 608, wherein the antibody is a naked antibody.

610. The method of embodiment 607, wherein the antibody is a naked antibody.

611. The method of embodiment 606, wherein the antibody is a humanized antibody.

612. The method of embodiment 611, wherein the antibody is a naked antibody.

613. The method of embodiment 606, wherein the antibody is a naked antibody.

614. The method of any one of embodiments 606-613, comprising administering a therapeutically effective amount of an antibody which specifically binds to a human KIT receptor (SEQ ID NO:1).

615. The method of embodiment 606, wherein the antibody comprises a light chain variable region ("VL") comprising VL CDRs 1-3 comprising SEQ ID NOs: 2-4, respectively, and a heavy chain variable region ("VH") comprising VH CDRs 1-3 comprising SEQ ID NOs: 5-7, respectively.

616. The method of embodiment 615, wherein the antibody is a bivalent monospecific antibody.

617. The method of embodiment 616, wherein the antibody is a humanized antibody.

618. The method of embodiment 617, wherein the antibody is a naked antibody.

619. The method of embodiment 616, wherein the antibody is a naked antibody.

620. The method of embodiment 615, wherein the antibody is a humanized antibody.

621. The method of embodiment 620, wherein the antibody is a naked antibody.

622. The method of embodiment 615, wherein the antibody is a naked antibody.

623. The method of embodiment 615, wherein the antibody comprises a VH comprising SEQ ID NO: 8.

624. The method of embodiment 615, wherein the antibody comprises a VH comprising SEQ ID NO: 9.

625. The method of embodiment 615, wherein the antibody comprises a VH comprising SEQ ID NO: 10.

626. The method of embodiment 615, wherein the antibody comprises a VH comprising SEQ ID NO: 11.

627. The method of embodiment 615, wherein the antibody comprises a VH comprising SEQ ID NO: 12.

628. The method of embodiment 615, wherein the antibody comprises a VL comprising SEQ ID NO: 13.

629. The method of embodiment 615, wherein the antibody comprises a VL comprising SEQ ID NO: 14.

630. The method of embodiment 615, wherein the antibody comprises a VL comprising SEQ ID NO: 15.

631. The method of embodiment 615, wherein the antibody comprises a VL comprising SEQ ID NO: 16.

632. The method of embodiment 615, wherein the antibody comprises a VH comprising SEQ ID NO: 8 and a VL comprising SEQ ID NO:13.

633. The method of embodiment 615, wherein the antibody comprises a VH comprising SEQ ID NO: 8 and a VL comprising SEQ ID NO:14.

634. The method of embodiment 615, wherein the antibody comprises a VH comprising SEQ ID NO: 8 and a VL comprising SEQ ID NO:15.

635. The method of embodiment 615, wherein the antibody comprises a VH comprising SEQ ID NO: 8 and a VL comprising SEQ ID NO:16.

636. The method of embodiment 615, wherein the antibody comprises a VH comprising SEQ ID NO: 9 and a VL comprising SEQ ID NO:13.

637. The method of embodiment 615, wherein the antibody comprises a VH comprising SEQ ID NO: 9 and a VL comprising SEQ ID NO:14.

638. The method of embodiment 615, wherein the antibody comprises a VH comprising SEQ ID NO: 9 and a VL comprising SEQ ID NO:15.

639. The method of embodiment 615, wherein the antibody comprises a VH comprising SEQ ID NO: 9 and a VL comprising SEQ ID NO:16.

640. The method of embodiment 615, wherein the antibody comprises a VH comprising SEQ ID NO: 10 and a VL comprising SEQ ID NO:13.

641. The method of embodiment 615, wherein the antibody comprises a VH comprising SEQ ID NO: 10 and a VL comprising SEQ ID NO:14.

642. The method of embodiment 615, wherein the antibody comprises a VH comprising SEQ ID NO: 10 and a VL comprising SEQ ID NO:15.

643. The method of embodiment 615, wherein the antibody comprises a VH comprising SEQ ID NO: 10 and a VL comprising SEQ ID NO:16.

644. The method of embodiment 615, wherein the antibody comprises a VH comprising SEQ ID NO: 11 and a VL comprising SEQ ID NO:13.

645. The method of embodiment 615, wherein the antibody comprises a VH comprising SEQ ID NO: 11 and a VL comprising SEQ ID NO:14.

646. The method of embodiment 615, wherein the antibody comprises a VH comprising SEQ ID NO: 11 and a VL comprising SEQ ID NO:15.

647. The method of embodiment 615, wherein the antibody comprises a VH comprising SEQ ID NO: 11 and a VL comprising SEQ ID NO:16.

648. The method of embodiment 615, wherein the antibody comprises a VH comprising SEQ ID NO: 11.

649. The method of embodiment 615, wherein the antibody comprises a VH comprising SEQ ID NO: 12 and a VL comprising SEQ ID NO:13.

650. The method of embodiment 615, wherein the antibody comprises a VH comprising SEQ ID NO: 12 and a VL comprising SEQ ID NO:14.

651. The method of embodiment 615, wherein the antibody comprises a VH comprising SEQ ID NO: 12 and a VL comprising SEQ ID NO:15.

652. The method of embodiment 615, wherein the antibody comprises a VH comprising SEQ ID NO: 12 and a VL comprising SEQ ID NO:16.

653. The method of any one of embodiments 623-652, comprising administering a therapeutically effective amount of an antibody which specifically binds to a human KIT receptor (SEQ ID NO:1).

654. A method of treating multiple sclerosis (MS) in a subject, comprising administering to a subject in need thereof a therapeutically effective amount of an antibody which specifically binds to a human KIT receptor (SEQ ID NO: 1), or an antigen binding fragment thereof.

655. The method of embodiment 654, wherein the antibody is a bivalent monospecific antibody.

656. The method of embodiment 655, wherein the antibody is a humanized antibody.

657. The method of embodiment 656, wherein the antibody is a naked antibody.

658. The method of embodiment 655, wherein the antibody is a naked antibody.

659. The method of embodiment 654, wherein the antibody is a humanized antibody.

660. The method of embodiment 659, wherein the antibody is a naked antibody.

661. The method of embodiment 654, wherein the antibody is a naked antibody.

662. The method of any one of embodiments 654-661, comprising administering a therapeutically effective amount of an antibody which specifically binds to a human KIT receptor (SEQ ID NO:1).

663. The method of embodiment 654, wherein the antibody comprises a light chain variable region ("VL") comprising VL CDRs 1-3 comprising SEQ ID NOs: 2-4, respectively, and a heavy chain variable region ("VH") comprising VH CDRs 1-3 comprising SEQ ID NOs: 5-7, respectively.

664. The method of embodiment 663, wherein the antibody is a bivalent monospecific antibody.

665. The method of embodiment 664, wherein the antibody is a humanized antibody.

666. The method of embodiment 665, wherein the antibody is a naked antibody.

667. The method of embodiment 664, wherein the antibody is a naked antibody.

668. The method of embodiment 663, wherein the antibody is a humanized antibody.

669. The method of embodiment 668, wherein the antibody is a naked antibody.

670. The method of embodiment 663, wherein the antibody is a naked antibody.

671. The method of any one of embodiments 663-670, comprising administering a therapeutically effective amount of an antibody which specifically binds to a human KIT receptor (SEQ ID NO:1).

672. The method of embodiment 663, wherein the antibody comprises a VH comprising SEQ ID NO: 8.

673. The method of embodiment 663, wherein the antibody comprises a VH comprising SEQ ID NO: 9.

674. The method of embodiment 663, wherein the antibody comprises a VH comprising SEQ ID NO: 10.

675. The method of embodiment 663, wherein the antibody comprises a VH comprising SEQ ID NO: 11.

676. The method of embodiment 663, wherein the antibody comprises a VH comprising SEQ ID NO: 12.

677. The method of embodiment 663, wherein the antibody comprises a VL comprising SEQ ID NO: 13.

678. The method of embodiment 663, wherein the antibody comprises a VL comprising SEQ ID NO: 14.

679. The method of embodiment 663, wherein the antibody comprises a VL comprising SEQ ID NO: 15.

680. The method of embodiment 663, wherein the antibody comprises a VL comprising SEQ ID NO: 16.

681. The method of embodiment 663, wherein the antibody comprises a VH comprising SEQ ID NO: 8 and a VL comprising SEQ ID NO:13.

682. The method of embodiment 663, wherein the antibody comprises a VH comprising SEQ ID NO: 8 and a VL comprising SEQ ID NO:14.

683. The method of embodiment 663, wherein the antibody comprises a VH comprising SEQ ID NO: 8 and a VL comprising SEQ ID NO:15.

684. The method of embodiment 663, wherein the antibody comprises a VH comprising SEQ ID NO: 8 and a VL comprising SEQ ID NO:16.

685. The method of embodiment 663, wherein the antibody comprises a VH comprising SEQ ID NO: 9 and a VL comprising SEQ ID NO:13.

686. The method of embodiment 663, wherein the antibody comprises a VH comprising SEQ ID NO: 9 and a VL comprising SEQ ID NO:14.

687. The method of embodiment 663, wherein the antibody comprises a VH comprising SEQ ID NO: 9 and a VL comprising SEQ ID NO:15.

688. The method of embodiment 663, wherein the antibody comprises a VH comprising SEQ ID NO: 9 and a VL comprising SEQ ID NO:16.

689. The method of embodiment 663, wherein the antibody comprises a VH comprising SEQ ID NO: 10 and a VL comprising SEQ ID NO:13.

690. The method of embodiment 663, wherein the antibody comprises a VH comprising SEQ ID NO: 10 and a VL comprising SEQ ID NO:14.

691. The method of embodiment 663, wherein the antibody comprises a VH comprising SEQ ID NO: 10 and a VL comprising SEQ ID NO:15.

692. The method of embodiment 663, wherein the antibody comprises a VH comprising SEQ ID NO: 10 and a VL comprising SEQ ID NO:16.

693. The method of embodiment 663, wherein the antibody comprises a VH comprising SEQ ID NO: 11 and a VL comprising SEQ ID NO:13.

694. The method of embodiment 663, wherein the antibody comprises a VH comprising SEQ ID NO: 11 and a VL comprising SEQ ID NO:14.

695. The method of embodiment 663, wherein the antibody comprises a VH comprising SEQ ID NO: 11 and a VL comprising SEQ ID NO:15.

696. The method of embodiment 663, wherein the antibody comprises a VH comprising SEQ ID NO: 11 and a VL comprising SEQ ID NO:16.

697. The method of embodiment 663, wherein the antibody comprises a VH comprising SEQ ID NO: 11.

698. The method of embodiment 663, wherein the antibody comprises a VH comprising SEQ ID NO: 12 and a VL comprising SEQ ID NO:13.

699. The method of embodiment 663, wherein the antibody comprises a VH comprising SEQ ID NO: 12 and a VL comprising SEQ ID NO:14.

700. The method of embodiment 663, wherein the antibody comprises a VH comprising SEQ ID NO: 12 and a VL comprising SEQ ID NO:15.

701. The method of embodiment 663, wherein the antibody comprises a VH comprising SEQ ID NO: 12 and a VL comprising SEQ ID NO:16.

702. The method of any one of embodiments 672-701, comprising administering a therapeutically effective amount of an antibody which specifically binds to a human KIT receptor (SEQ ID NO:1).

703. A method of managing MS in a subject, comprising administering to a subject in need thereof a therapeutically effective amount of an antibody which specifically binds to a human KIT receptor (SEQ ID NO: 1), or an antigen binding fragment thereof.

704. The method of embodiment 703, wherein the antibody is a bivalent monospecific antibody.

705. The method of embodiment 704, wherein the antibody is a humanized antibody.

706. The method of embodiment 705, wherein the antibody is a naked antibody.

707. The method of embodiment 704, wherein the antibody is a naked antibody.

708. The method of embodiment 703, wherein the antibody is a humanized antibody.

709. The method of embodiment 708, wherein the antibody is a naked antibody.

710. The method of embodiment 703, wherein the antibody is a naked antibody.

711. The method of any one of embodiments 703-710, comprising administering a therapeutically effective amount of an antibody which specifically binds to a human KIT receptor (SEQ ID NO:1).

712. The method of embodiment 703, wherein the antibody comprises a light chain variable region ("VL") comprising VL CDRs 1-3 comprising SEQ ID NOs: 2-4, respectively, and a heavy chain variable region ("VH") comprising VH CDRs 1-3 comprising SEQ ID NOs: 5-7, respectively.

713. The method of embodiment 712, wherein the antibody is a bivalent monospecific antibody.

714. The method of embodiment 713, wherein the antibody is a humanized antibody.

715. The method of embodiment 714, wherein the antibody is a naked antibody.

716. The method of embodiment 713, wherein the antibody is a naked antibody.

717. The method of embodiment 712, wherein the antibody is a humanized antibody.

718. The method of embodiment 717, wherein the antibody is a naked antibody.

719. The method of embodiment 712, wherein the antibody is a naked antibody.

720. The method of any one of embodiments 712-719, comprising administering a therapeutically effective amount of an antibody which specifically binds to a human KIT receptor (SEQ ID NO:1).

721. The method of embodiment 712, wherein the antibody comprises a VH comprising SEQ ID NO: 8.

722. The method of embodiment 712, wherein the antibody comprises a VH comprising SEQ ID NO: 9.

723. The method of embodiment 712, wherein the antibody comprises a VH comprising SEQ ID NO: 10.

724. The method of embodiment 712, wherein the antibody comprises a VH comprising SEQ ID NO: 11.

725. The method of embodiment 712, wherein the antibody comprises a VH comprising SEQ ID NO: 12.

726. The method of embodiment 712, wherein the antibody comprises a VL comprising SEQ ID NO: 13.

727. The method of embodiment 712, wherein the antibody comprises a VL comprising SEQ ID NO: 14.

728. The method of embodiment 712, wherein the antibody comprises a VL comprising SEQ ID NO: 15.

729. The method of embodiment 712, wherein the antibody comprises a VL comprising SEQ ID NO: 16.

730. The method of embodiment 712, wherein the antibody comprises a VH comprising SEQ ID NO: 8 and a VL comprising SEQ ID NO:13.

731. The method of embodiment 712, wherein the antibody comprises a VH comprising SEQ ID NO: 8 and a VL comprising SEQ ID NO:14.

732. The method of embodiment 712, wherein the antibody comprises a VH comprising SEQ ID NO: 8 and a VL comprising SEQ ID NO:15.

733. The method of embodiment 712, wherein the antibody comprises a VH comprising SEQ ID NO: 8 and a VL comprising SEQ ID NO:16.

734. The method of embodiment 712, wherein the antibody comprises a VH comprising SEQ ID NO: 9 and a VL comprising SEQ ID NO:13.

735. The method of embodiment 712, wherein the antibody comprises a VH comprising SEQ ID NO: 9 and a VL comprising SEQ ID NO:14.

736. The method of embodiment 712, wherein the antibody comprises a VH comprising SEQ ID NO: 9 and a VL comprising SEQ ID NO:15.

737. The method of embodiment 712, wherein the antibody comprises a VH comprising SEQ ID NO: 9 and a VL comprising SEQ ID NO:16.

738. The method of embodiment 712, wherein the antibody comprises a VH comprising SEQ ID NO: 10 and a VL comprising SEQ ID NO:13.

739. The method of embodiment 712, wherein the antibody comprises a VH comprising SEQ ID NO: 10 and a VL comprising SEQ ID NO:14.

740. The method of embodiment 712, wherein the antibody comprises a VH comprising SEQ ID NO: 10 and a VL comprising SEQ ID NO:15.

741. The method of embodiment 712, wherein the antibody comprises a VH comprising SEQ ID NO: 10 and a VL comprising SEQ ID NO:16.

742. The method of embodiment 712, wherein the antibody comprises a VH comprising SEQ ID NO: 11 and a VL comprising SEQ ID NO:13.

743. The method of embodiment 712, wherein the antibody comprises a VH comprising SEQ ID NO: 11 and a VL comprising SEQ ID NO:14.

744. The method of embodiment 712, wherein the antibody comprises a VH comprising SEQ ID NO: 11 and a VL comprising SEQ ID NO:15.

745. The method of embodiment 712, wherein the antibody comprises a VH comprising SEQ ID NO: 11 and a VL comprising SEQ ID NO:16.

746. The method of embodiment 712, wherein the antibody comprises a VH comprising SEQ ID NO: 11.

747. The method of embodiment 712, wherein the antibody comprises a VH comprising SEQ ID NO: 12 and a VL comprising SEQ ID NO:13.

748. The method of embodiment 712, wherein the antibody comprises a VH comprising SEQ ID NO: 12 and a VL comprising SEQ ID NO:14.

749. The method of embodiment 712, wherein the antibody comprises a VH comprising SEQ ID NO: 12 and a VL comprising SEQ ID NO:15.

750. The method of embodiment 712, wherein the antibody comprises a VH comprising SEQ ID NO: 12 and a VL comprising SEQ ID NO:16.

751. The method of any one of embodiments 721-750, comprising administering a therapeutically effective amount of an antibody which specifically binds to a human KIT receptor (SEQ ID NO:1).

752. A method of protecting against MS in a subject, comprising administering to a subject in need thereof a therapeutically effective amount of an antibody which specifically binds to a human KIT receptor (SEQ ID NO: 1), or an antigen binding fragment thereof.

753. The method of embodiment 752, wherein the antibody is a bivalent monospecific antibody.

754. The method of embodiment 753, wherein the antibody is a humanized antibody.

755. The method of embodiment 754, wherein the antibody is a naked antibody.

756. The method of embodiment 753, wherein the antibody is a naked antibody.

757. The method of embodiment 752, wherein the antibody is a humanized antibody.

758. The method of embodiment 757, wherein the antibody is a naked antibody.

759. The method of embodiment 752, wherein the antibody is a naked antibody.

760. The method of any one of embodiments 752-759, comprising administering a therapeutically effective amount of an antibody which specifically binds to a human KIT receptor (SEQ ID NO:1).

761. The method of embodiment 752, wherein the antibody comprises a light chain variable region ("VL") comprising VL CDRs 1-3 comprising SEQ ID NOs: 2-4, respectively, and a heavy chain variable region ("VH") comprising VH CDRs 1-3 comprising SEQ ID NOs: 5-7, respectively.

762. The method of embodiment 761, wherein the antibody is a bivalent monospecific antibody.

763. The method of embodiment 762, wherein the antibody is a humanized antibody.

764. The method of embodiment 763, wherein the antibody is a naked antibody.

765. The method of embodiment 762, wherein the antibody is a naked antibody.

766. The method of embodiment 761, wherein the antibody is a humanized antibody.

767. The method of embodiment 766, wherein the antibody is a naked antibody.

768. The method of embodiment 761, wherein the antibody is a naked antibody.

769. The method of any one of embodiments 761-768, comprising administering a therapeutically effective amount of an antibody which specifically binds to a human KIT receptor (SEQ ID NO:1).

770. The method of embodiment 761, wherein the antibody comprises a VH comprising SEQ ID NO: 8.

771. The method of embodiment 761, wherein the antibody comprises a VH comprising SEQ ID NO: 9.

772. The method of embodiment 761, wherein the antibody comprises a VH comprising SEQ ID NO: 10.

773. The method of embodiment 761, wherein the antibody comprises a VH comprising SEQ ID NO: 11.

774. The method of embodiment 761, wherein the antibody comprises a VH comprising SEQ ID NO: 12.

775. The method of embodiment 761, wherein the antibody comprises a VL comprising SEQ ID NO: 13.

776. The method of embodiment 761, wherein the antibody comprises a VL comprising SEQ ID NO: 14.

777. The method of embodiment 761, wherein the antibody comprises a VL comprising SEQ ID NO: 15.

778. The method of embodiment 761, wherein the antibody comprises a VL comprising SEQ ID NO: 16.

779. The method of embodiment 761, wherein the antibody comprises a VH comprising SEQ ID NO: 8 and a VL comprising SEQ ID NO:13.

780. The method of embodiment 761, wherein the antibody comprises a VH comprising SEQ ID NO: 8 and a VL comprising SEQ ID NO:14.

781. The method of embodiment 761, wherein the antibody comprises a VH comprising SEQ ID NO: 8 and a VL comprising SEQ ID NO:15.

782. The method of embodiment 761, wherein the antibody comprises a VH comprising SEQ ID NO: 8 and a VL comprising SEQ ID NO:16.

783. The method of embodiment 761, wherein the antibody comprises a VH comprising SEQ ID NO: 9 and a VL comprising SEQ ID NO:13.

784. The method of embodiment 761, wherein the antibody comprises a VH comprising SEQ ID NO: 9 and a VL comprising SEQ ID NO:14.

785. The method of embodiment 761, wherein the antibody comprises a VH comprising SEQ ID NO: 9 and a VL comprising SEQ ID NO:15.

786. The method of embodiment 761, wherein the antibody comprises a VH comprising SEQ ID NO: 9 and a VL comprising SEQ ID NO:16.

787. The method of embodiment 761, wherein the antibody comprises a VH comprising SEQ ID NO: 10 and a VL comprising SEQ ID NO:13.

788. The method of embodiment 761, wherein the antibody comprises a VH comprising SEQ ID NO: 10 and a VL comprising SEQ ID NO:14.

789. The method of embodiment 761, wherein the antibody comprises a VH comprising SEQ ID NO: 10 and a VL comprising SEQ ID NO:15.

790. The method of embodiment 761, wherein the antibody comprises a VH comprising SEQ ID NO: 10 and a VL comprising SEQ ID NO:16.

791. The method of embodiment 761, wherein the antibody comprises a VH comprising SEQ ID NO: 11 and a VL comprising SEQ ID NO:13.

792. The method of embodiment 761, wherein the antibody comprises a VH comprising SEQ ID NO: 11 and a VL comprising SEQ ID NO:14.

793. The method of embodiment 761, wherein the antibody comprises a VH comprising SEQ ID NO: 11 and a VL comprising SEQ ID NO:15.

794. The method of embodiment 761, wherein the antibody comprises a VH comprising SEQ ID NO: 11 and a VL comprising SEQ ID NO:16.

795. The method of embodiment 761, wherein the antibody comprises a VH comprising SEQ ID NO: 11.

796. The method of embodiment 761, wherein the antibody comprises a VH comprising SEQ ID NO: 12 and a VL comprising SEQ ID NO:13.

797. The method of embodiment 761, wherein the antibody comprises a VH comprising SEQ ID NO: 12 and a VL comprising SEQ ID NO:14.

798. The method of embodiment 761, wherein the antibody comprises a VH comprising SEQ ID NO: 12 and a VL comprising SEQ ID NO:15.

799. The method of embodiment 761, wherein the antibody comprises a VH comprising SEQ ID NO: 12 and a VL comprising SEQ ID NO:16.

800. The method of any one of embodiments 770-799, comprising administering a therapeutically effective amount of an antibody which specifically binds to a human KIT receptor (SEQ ID NO:1).

801. A method of reducing inflammation in a subject, comprising administering to a subject diagnosed with a mast cell related disorder of the nervous system a therapeutically effective amount of an antibody which specifically binds to a human KIT receptor (SEQ ID NO: 1), or an antigen binding fragment thereof.

802. The method of embodiment 801, wherein the antibody is a bivalent monospecific antibody.

803. The method of embodiment 802, wherein the antibody is a humanized antibody.

804. The method of embodiment 803, wherein the antibody is a naked antibody.

805. The method of embodiment 802, wherein the antibody is a naked antibody.

806. The method of embodiment 801, wherein the antibody is a humanized antibody.

807. The method of embodiment 806, wherein the antibody is a naked antibody.

808. The method of embodiment 801, wherein the antibody is a naked antibody.

809. The method of any one of embodiments 801-808, comprising administering a therapeutically effective amount of an antibody which specifically binds to a human KIT receptor (SEQ ID NO:1).

810. The method of embodiment 801, wherein the antibody comprises a light chain variable region ("VL") comprising VL CDRs 1-3 comprising SEQ ID NOs: 2-4, respectively, and a heavy chain variable region ("VH") comprising VH CDRs 1-3 comprising SEQ ID NOs: 5-7, respectively.

811. The method of embodiment 810, wherein the antibody is a bivalent monospecific antibody.

812. The method of embodiment 811, wherein the antibody is a humanized antibody.

813. The method of embodiment 812, wherein the antibody is a naked antibody.

814. The method of embodiment 811, wherein the antibody is a naked antibody.

815. The method of embodiment 810, wherein the antibody is a humanized antibody.

816. The method of embodiment 815, wherein the antibody is a naked antibody.

817. The method of embodiment 810, wherein the antibody is a naked antibody.

818. The method of any one of embodiments 810-817, comprising administering a therapeutically effective amount of an antibody which specifically binds to a human KIT receptor (SEQ ID NO:1).

819. The method of embodiment 810, wherein the antibody comprises a VH comprising SEQ ID NO: 8.

820. The method of embodiment 810, wherein the antibody comprises a VH comprising SEQ ID NO: 9.

821. The method of embodiment 810, wherein the antibody comprises a VH comprising SEQ ID NO: 10.

822. The method of embodiment 810, wherein the antibody comprises a VH comprising SEQ ID NO: 11.

823. The method of embodiment 810, wherein the antibody comprises a VH comprising SEQ ID NO: 12.

824. The method of embodiment 810, wherein the antibody comprises a VL comprising SEQ ID NO: 13.

825. The method of embodiment 810, wherein the antibody comprises a VL comprising SEQ ID NO: 14.

826. The method of embodiment 810, wherein the antibody comprises a VL comprising SEQ ID NO: 15.

827. The method of embodiment 810, wherein the antibody comprises a VL comprising SEQ ID NO: 16.

828. The method of embodiment 810, wherein the antibody comprises a VH comprising SEQ ID NO: 8 and a VL comprising SEQ ID NO:13.

829. The method of embodiment 810, wherein the antibody comprises a VH comprising SEQ ID NO: 8 and a VL comprising SEQ ID NO:14.

830. The method of embodiment 810, wherein the antibody comprises a VH comprising SEQ ID NO: 8 and a VL comprising SEQ ID NO:15.

831. The method of embodiment 810, wherein the antibody comprises a VH comprising SEQ ID NO: 8 and a VL comprising SEQ ID NO:16.

832. The method of embodiment 810, wherein the antibody comprises a VH comprising SEQ ID NO: 9 and a VL comprising SEQ ID NO:13.

833. The method of embodiment 810, wherein the antibody comprises a VH comprising SEQ ID NO: 9 and a VL comprising SEQ ID NO:14.

834. The method of embodiment 810, wherein the antibody comprises a VH comprising SEQ ID NO: 9 and a VL comprising SEQ ID NO:15.

835. The method of embodiment 810, wherein the antibody comprises a VH comprising SEQ ID NO: 9 and a VL comprising SEQ ID NO:16.

836. The method of embodiment 810, wherein the antibody comprises a VH comprising SEQ ID NO: 10 and a VL comprising SEQ ID NO:13.

837. The method of embodiment 810, wherein the antibody comprises a VH comprising SEQ ID NO: 10 and a VL comprising SEQ ID NO:14.

838. The method of embodiment 810, wherein the antibody comprises a VH comprising SEQ ID NO: 10 and a VL comprising SEQ ID NO:15.

839. The method of embodiment 810, wherein the antibody comprises a VH comprising SEQ ID NO: 10 and a VL comprising SEQ ID NO:16.

840. The method of embodiment 810, wherein the antibody comprises a VH comprising SEQ ID NO: 11 and a VL comprising SEQ ID NO:13.

841. The method of embodiment 810, wherein the antibody comprises a VH comprising SEQ ID NO: 11 and a VL comprising SEQ ID NO:14.

842. The method of embodiment 810, wherein the antibody comprises a VH comprising SEQ ID NO: 11 and a VL comprising SEQ ID NO:15.

843. The method of embodiment 810, wherein the antibody comprises a VH comprising SEQ ID NO: 11 and a VL comprising SEQ ID NO:16.

844. The method of embodiment 810, wherein the antibody comprises a VH comprising SEQ ID NO: 11.

845. The method of embodiment 810, wherein the antibody comprises a VH comprising SEQ ID NO: 12 and a VL comprising SEQ ID NO:13.

846. The method of embodiment 810, wherein the antibody comprises a VH comprising SEQ ID NO: 12 and a VL comprising SEQ ID NO:14.

847. The method of embodiment 810, wherein the antibody comprises a VH comprising SEQ ID NO: 12 and a VL comprising SEQ ID NO:15.

848. The method of embodiment 810, wherein the antibody comprises a VH comprising SEQ ID NO: 12 and a VL comprising SEQ ID NO:16.

849. The method of any one of embodiments 819-848, comprising administering a therapeutically effective amount of an antibody which specifically binds to a human KIT receptor (SEQ ID NO:1).

850. A method of inhibiting mast cell activation in a subject, comprising administering to a subject diagnosed with a mast cell related disorder of the nervous system a therapeutically effective amount of an antibody which specifically binds to a human KIT receptor (SEQ ID NO: 1), or an antigen binding fragment thereof.

851. The method of embodiment 850, wherein the antibody is a bivalent monospecific antibody.

852. The method of embodiment 851, wherein the antibody is a humanized antibody.

853. The method of embodiment 852, wherein the antibody is a naked antibody.

854. The method of embodiment 851, wherein the antibody is a naked antibody.

855. The method of embodiment 850, wherein the antibody is a humanized antibody.

856. The method of embodiment 855, wherein the antibody is a naked antibody.

857. The method of embodiment 850, wherein the antibody is a naked antibody.

858. The method of any one of embodiments 850-857, comprising administering a therapeutically effective amount of an antibody which specifically binds to a human KIT receptor (SEQ ID NO:1).

859. The method of embodiment 850, wherein the antibody comprises a light chain variable region ("VL") comprising VL CDRs 1-3 comprising SEQ ID NOs: 2-4, respectively, and a heavy chain variable region ("VH") comprising VH CDRs 1-3 comprising SEQ ID NOs: 5-7, respectively.

860. The method of embodiment 859, wherein the antibody is a bivalent monospecific antibody.

861. The method of embodiment 860, wherein the antibody is a humanized antibody.

862. The method of embodiment 861, wherein the antibody is a naked antibody.

863. The method of embodiment 860, wherein the antibody is a naked antibody.

864. The method of embodiment 859, wherein the antibody is a humanized antibody.

865. The method of embodiment 864, wherein the antibody is a naked antibody.

866. The method of embodiment 859, wherein the antibody is a naked antibody.

867. The method of any one of embodiments 859-866, comprising administering a therapeutically effective amount of an antibody which specifically binds to a human KIT receptor (SEQ ID NO:1).

868. The method of embodiment 859, wherein the antibody comprises a VH comprising SEQ ID NO: 8.

869. The method of embodiment 859, wherein the antibody comprises a VH comprising SEQ ID NO: 9.

870. The method of embodiment 859, wherein the antibody comprises a VH comprising SEQ ID NO: 10.

871. The method of embodiment 859, wherein the antibody comprises a VH comprising SEQ ID NO: 11.

872. The method of embodiment 859, wherein the antibody comprises a VH comprising SEQ ID NO: 12.

873. The method of embodiment 859, wherein the antibody comprises a VL comprising SEQ ID NO: 13.

874. The method of embodiment 859, wherein the antibody comprises a VL comprising SEQ ID NO: 14.

875. The method of embodiment 859, wherein the antibody comprises a VL comprising SEQ ID NO: 15.

876. The method of embodiment 859, wherein the antibody comprises a VL comprising SEQ ID NO: 16.

877. The method of embodiment 859, wherein the antibody comprises a VH comprising SEQ ID NO: 8 and a VL comprising SEQ ID NO:13.

878. The method of embodiment 859, wherein the antibody comprises a VH comprising SEQ ID NO: 8 and a VL comprising SEQ ID NO:14.

879. The method of embodiment 859, wherein the antibody comprises a VH comprising SEQ ID NO: 8 and a VL comprising SEQ ID NO:15.

880. The method of embodiment 859, wherein the antibody comprises a VH comprising SEQ ID NO: 8 and a VL comprising SEQ ID NO:16.

881. The method of embodiment 859, wherein the antibody comprises a VH comprising SEQ ID NO: 9 and a VL comprising SEQ ID NO:13.

882. The method of embodiment 859, wherein the antibody comprises a VH comprising SEQ ID NO: 9 and a VL comprising SEQ ID NO:14.

883. The method of embodiment 859, wherein the antibody comprises a VH comprising SEQ ID NO: 9 and a VL comprising SEQ ID NO:15.

884. The method of embodiment 859, wherein the antibody comprises a VH comprising SEQ ID NO: 9 and a VL comprising SEQ ID NO:16.

885. The method of embodiment 859, wherein the antibody comprises a VH comprising SEQ ID NO: 10 and a VL comprising SEQ ID NO:13.

886. The method of embodiment 859, wherein the antibody comprises a VH comprising SEQ ID NO: 10 and a VL comprising SEQ ID NO:14.

887. The method of embodiment 859, wherein the antibody comprises a VH comprising SEQ ID NO: 10 and a VL comprising SEQ ID NO:15.

888. The method of embodiment 859, wherein the antibody comprises a VH comprising SEQ ID NO: 10 and a VL comprising SEQ ID NO:16.

889. The method of embodiment 859, wherein the antibody comprises a VH comprising SEQ ID NO: 11 and a VL comprising SEQ ID NO:13.

890. The method of embodiment 859, wherein the antibody comprises a VH comprising SEQ ID NO: 11 and a VL comprising SEQ ID NO:14.

891. The method of embodiment 859, wherein the antibody comprises a VH comprising SEQ ID NO: 11 and a VL comprising SEQ ID NO:15.

892. The method of embodiment 859, wherein the antibody comprises a VH comprising SEQ ID NO: 11 and a VL comprising SEQ ID NO:16.

893. The method of embodiment 859, wherein the antibody comprises a VH comprising SEQ ID NO: 11.

894. The method of embodiment 859, wherein the antibody comprises a VH comprising SEQ ID NO: 12 and a VL comprising SEQ ID NO:13.

895. The method of embodiment 859, wherein the antibody comprises a VH comprising SEQ ID NO: 12 and a VL comprising SEQ ID NO:14.

896. The method of embodiment 859, wherein the antibody comprises a VH comprising SEQ ID NO: 12 and a VL comprising SEQ ID NO:15.

897. The method of embodiment 859, wherein the antibody comprises a VH comprising SEQ ID NO: 12 and a VL comprising SEQ ID NO:16.

898. The method of any one of embodiments 868-897, comprising administering a therapeutically effective amount of an antibody which specifically binds to a human KIT receptor (SEQ ID NO:1).

899. The method of any one of embodiments 1-898, wherein the antibody is a bivalent monospecific antibody.

900. The method of any one of embodiments 1-898, wherein the antibody is not a bispecific antibody.

901. The method of any one of embodiments 1-900, wherein the subject is a human adult.

902. The method of any one of embodiments 1-900, wherein the subject is a child.

4. BRIEF DESCRIPTION OF THE FIGURES

FIG. 1 depicts the amino acid sequence of full length human KIT (SEQ ID NO: 1), GenBank™ accession number AAC50969. The first through fifth extracellular Ig-like domains (i.e., D1, D2, D3, D4, and D5) are indicated; "{" depicts the amino-terminal residue of each domain and "}" depicts the carboxyl-terminal residue of each domain. The D1 domain is depicted at P34 to R112, the D2 domain is depicted at D113 to P206, the D3 domain is depicted at A207 to D309, the D4 domain is depicted at K310 to N410, the hinge region between D4 and D5 is located at V409 to N410, and the D5 domain is depicted at T411 to K509. Also, the D1/D2 hinge region is located at D113 to L117; the D2/D3 hinge region is located at P206 to A210; and the D3/D4 hinge region is located at D309 to G311. The D4/D5 region comprises K310 to K509. The transmembrane domain comprises residues F525 to Q545, and the kinase domain comprises residues K589 to S933.

Figure 2B:
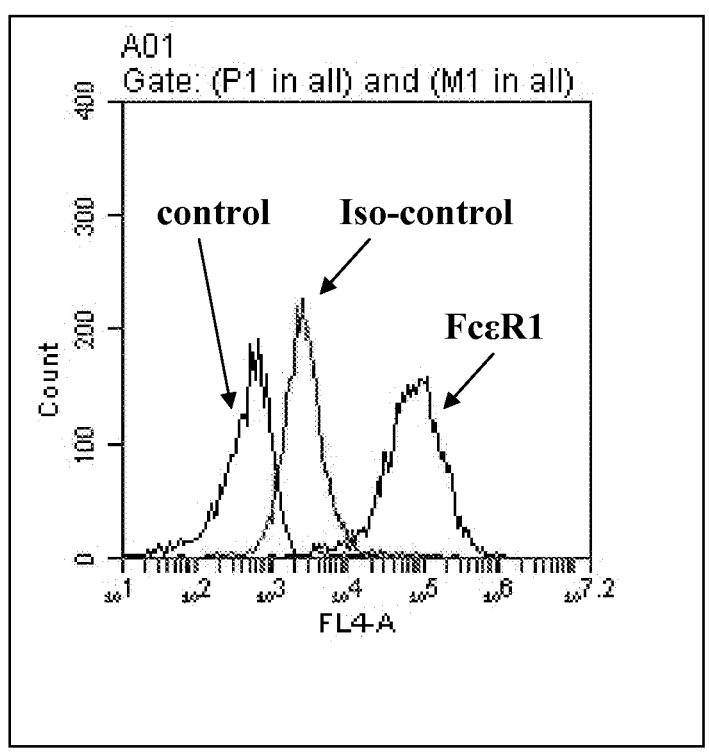
Figure 2C:
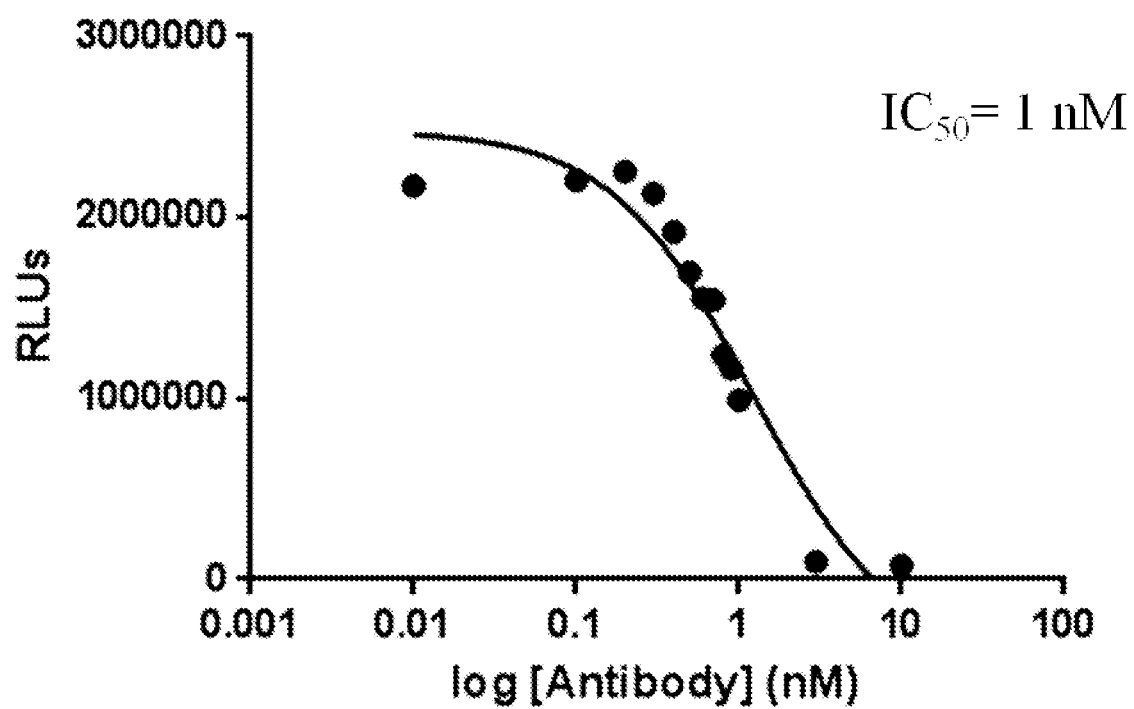

FIG. 2A, FIG. 2B, and FIG. 2C demonstrate that an antibody comprising the CDRs depicted in Table 1, below (herein referred to as "anti-KIT-1"), inhibits ligand-induced phosphorylation of KIT in mast cells. (A) Fluorescence-activated cell sorting ("FACS") analysis demonstrating the expression of KIT on LAD2. (B) FACS analysis demonstrating the expression of FcεR1 on LAD2 cells. (C) ELISA assay with an anti-phosphorylated tyrosine antibody to detect the level of ligand-induced phosphorylation of KIT in the presence of anti-KIT-1 antibody.

Figure 3A:
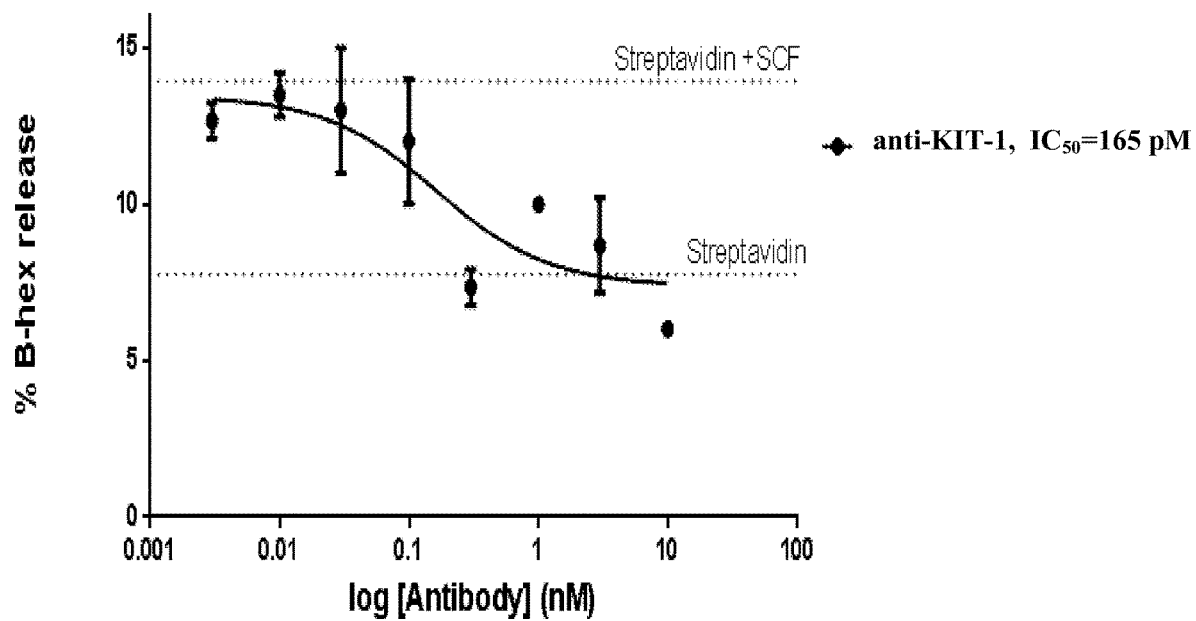
Figure 3B:
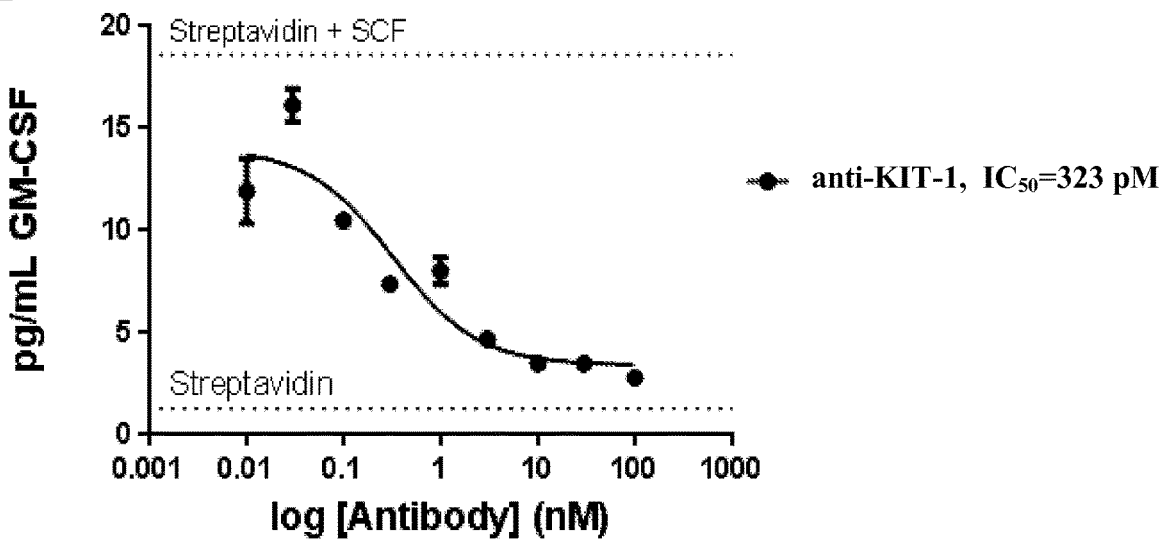
Figure 3C:
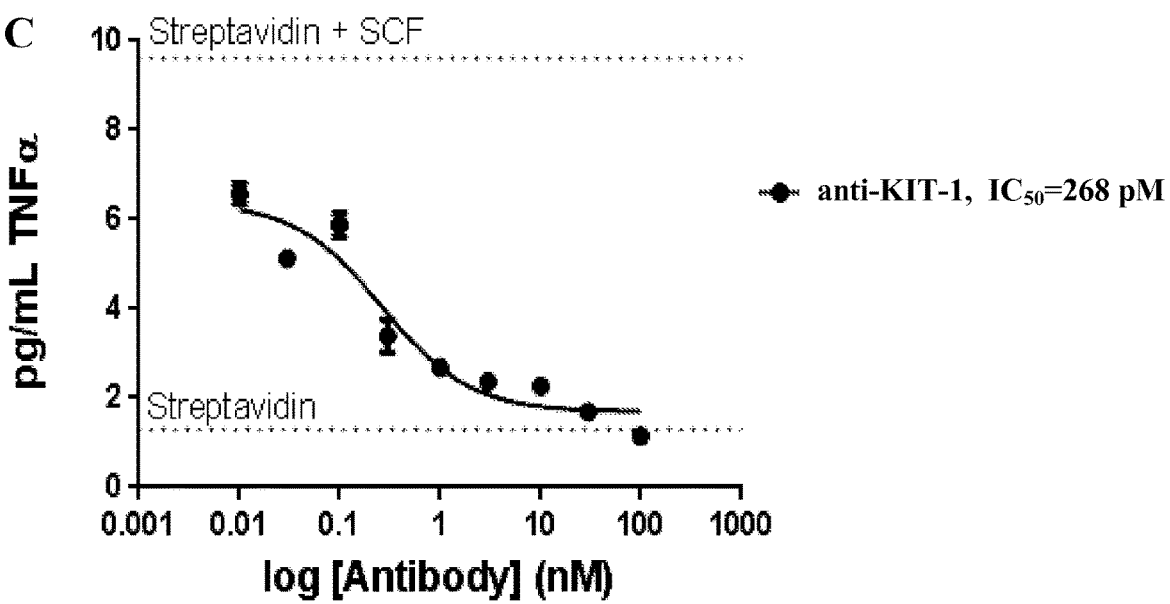

FIG. 3A, FIG. 3B, and FIG. 3C demonstrate that anti-KIT-1 antibody inhibits mast cell degranulation and cytokine release. (A) The percent of β-hexosaminidase ("B-hex") released by LAD2 cells is analyzed in the presence and absence of anti-KIT-1 in the presence and absence of ligand stimulation. The dotted line associated with "Streptavidin" refers to the percent of β-hexosaminidase released in cells treated with streptavidin in the absence of the KIT ligand stem cell factor ("SCF") and in the absence of anti-KIT-1. The dotted line associated with "Streptavidin+SCF" refers to the percent of β-hexosaminidase released in cells treated with streptavidin and SCF and in the absence of anti-KIT-1. (B) Concentration of tumor necrosis factor alpha ("TNFα") released from LAD2 cells in the presence and absence of anti-KIT-1 antibody in the presence and absence of ligand stimulation. (C) Concentration of granulocyte macrophage colony-stimulating factor ("GM-CSF") released from LAD2 cells in the presence and absence of anti-KIT-1 antibody in the presence and absence of ligand stimulation.

Figure 4:
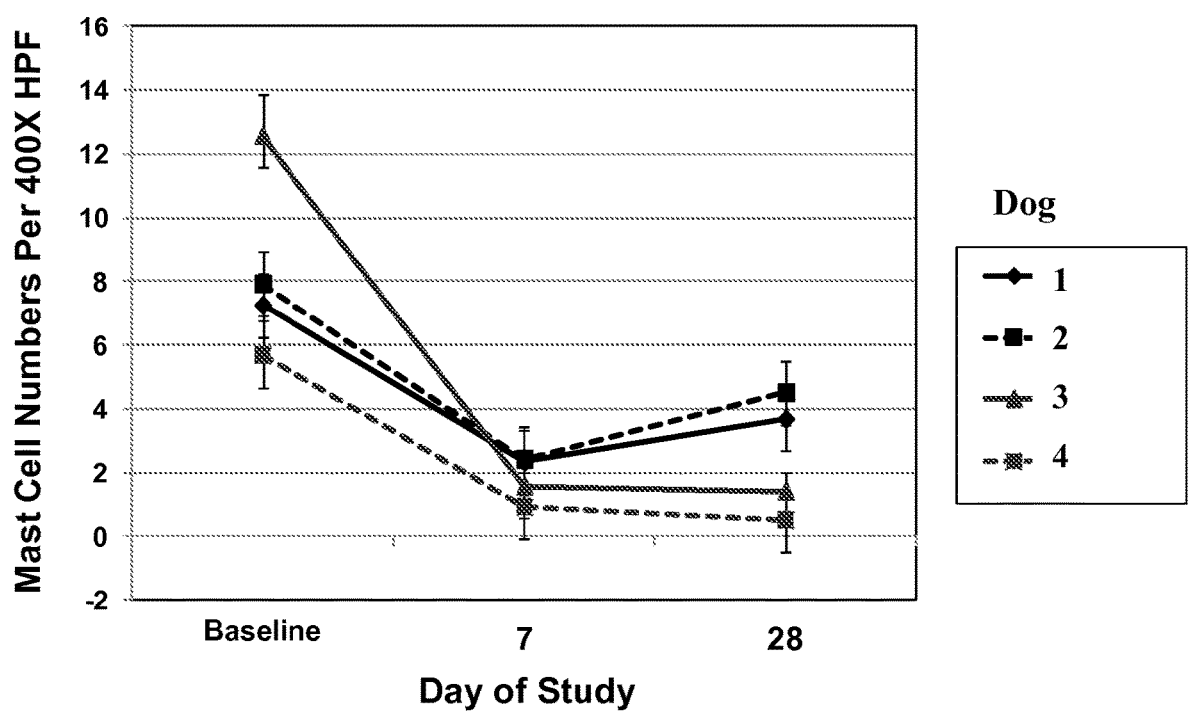

FIG. 4 demonstrates that administration of anti-KIT-1 results in a decrease in mast cell numbers in each 400× high powered field ("400× HPF") in dogs 1, 2, 3, and 4 (black diamonds, black squares, grey triangles, and grey squares, respectively).

Figure 5A:
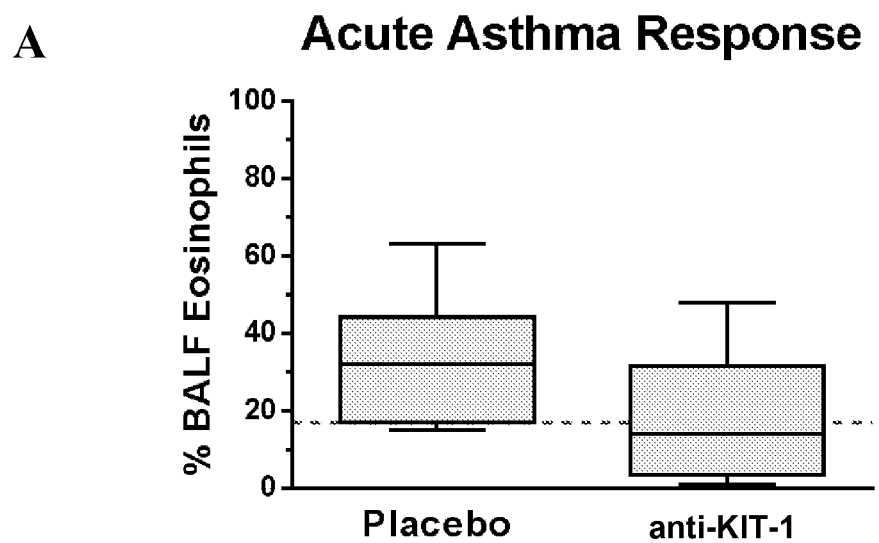
Figure 5B:
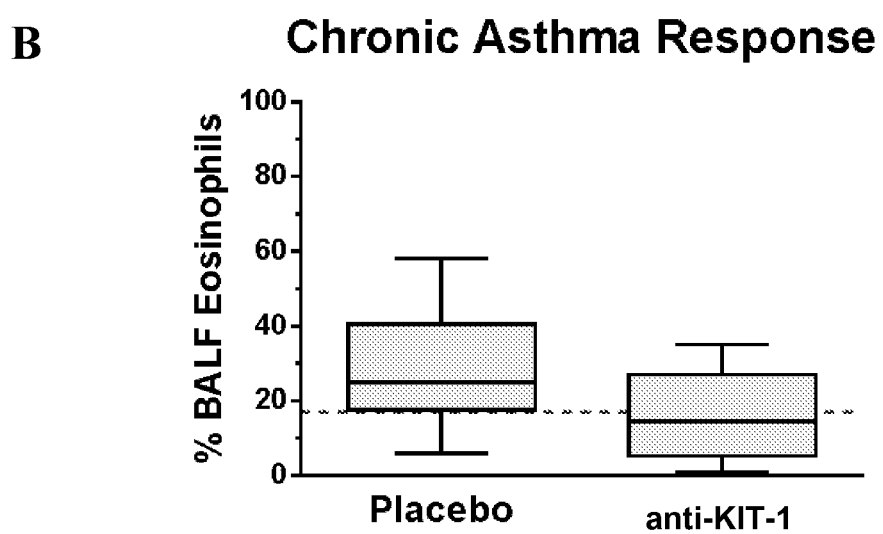

FIG. 5A and FIG. 5B demonstrate that anti-KIT-1 administration decreases the airway eosinophil population. (A) Acute asthma model cats administered anti-KIT-1 display a significant reduction in the percentage of airway broncho-alveolar lavage fluid ("BALF") eosinophils as compared to placebo treatment. (B) Chronic asthma model cats administered anti-KIT-1 display a significant reduction in the percentage of airway BALF eosinophils as compared to placebo treatment. The dotted line represents 17% BALF eosinophils; greater than 17% BALF eosinophils is indicative of an asthma phenotype.

Figures 6A, 6B:
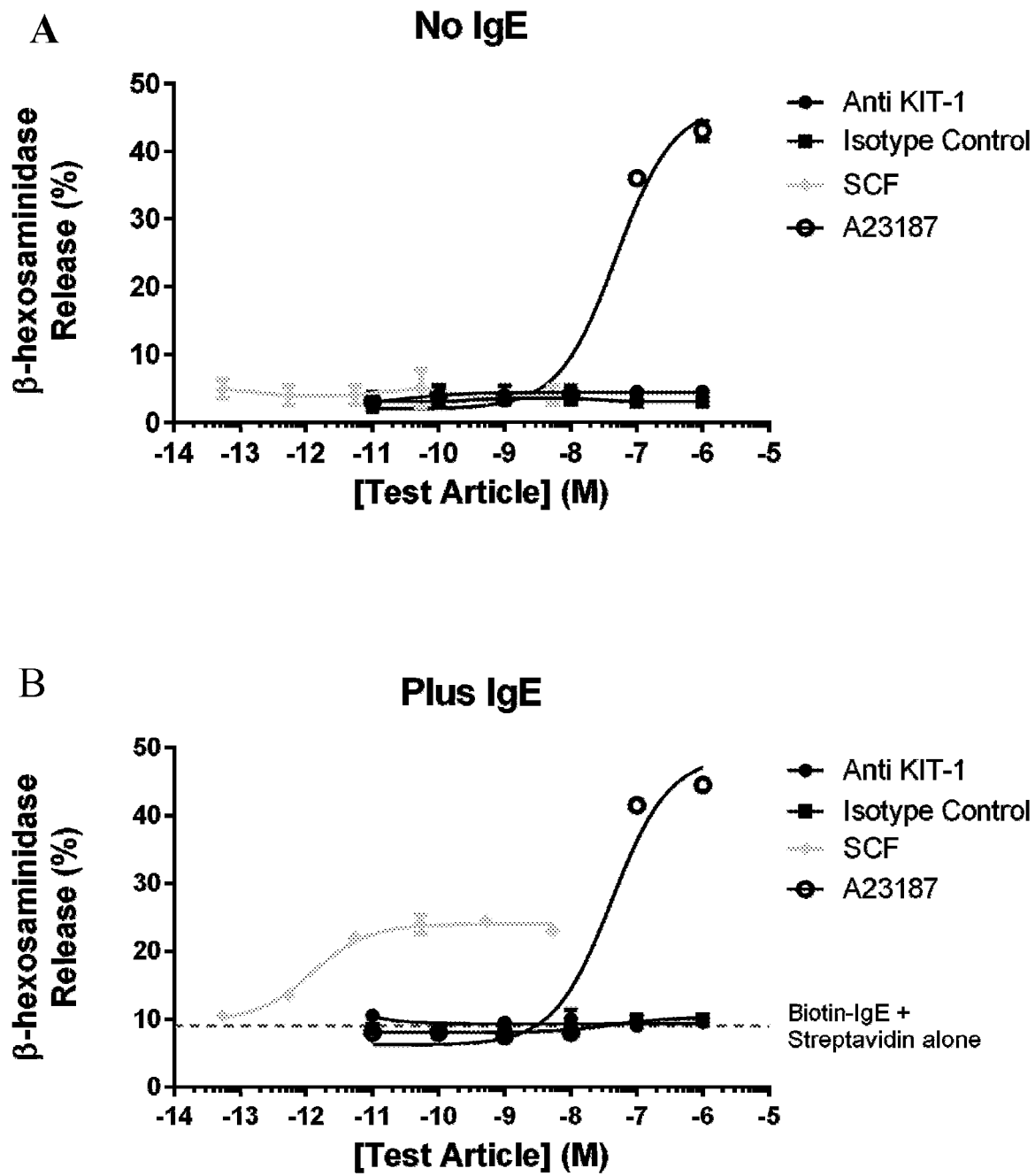

FIG. 6A and FIG. 6B demonstrate that anti-KIT-1 antibody does not induce primary human mast cell degranulation in vitro. Mast cell degranulation was assessed by measuring β-hexosaminidase activity released into culture supernatants. β-hexosaminidase release was measured after treating mast cells with serial 10-fold dilutions of anti-KIT-1, isotype control antibody, SCF, or the calcium ionophore A23187, showing their ability to degranulate mast cells alone (A), or their ability to augment IgE-mediated degranulation (B).

Figure 7:
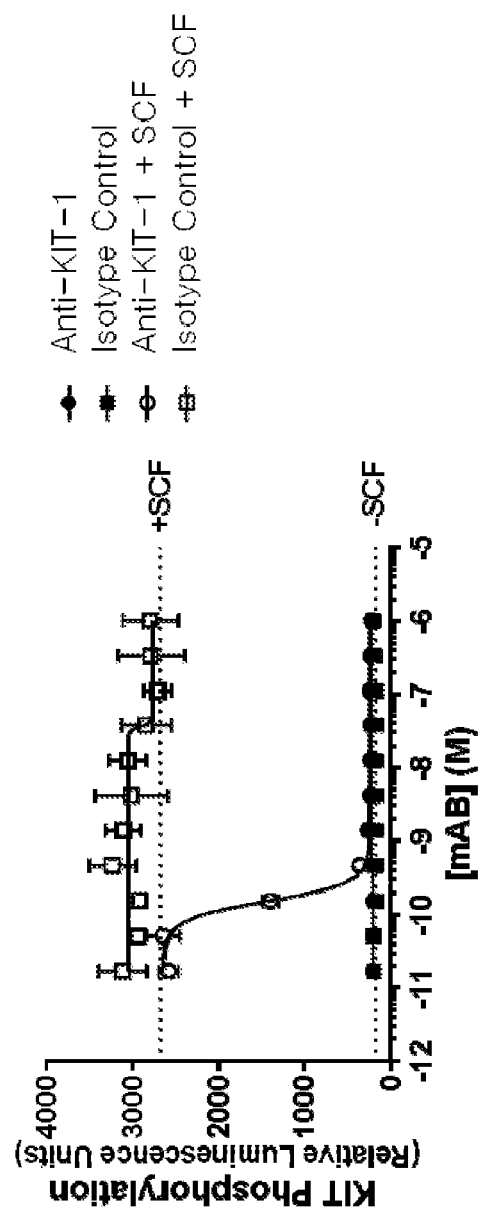

FIG. 7 demonstrates the effects of anti-KIT-1 antibody on SCF-induced KIT phosphorylation in CHO-WT KIT cells. In CHO-WT KIT cells treated with SCF, anti-KIT-1 antibody inhibited KIT phosphorylation in a dose-dependent manner over 4 independent experiments. The isotype control antibody had no effect on SCF induced KIT phosphorylation. In the absence of SCF, the level of KIT phosphorylation was similar in cells treated with either anti-KIT-1 antibody or the isotype control antibody at concentrations up to 1 μM (150 μg/mL).

Figures 8A, 8B:
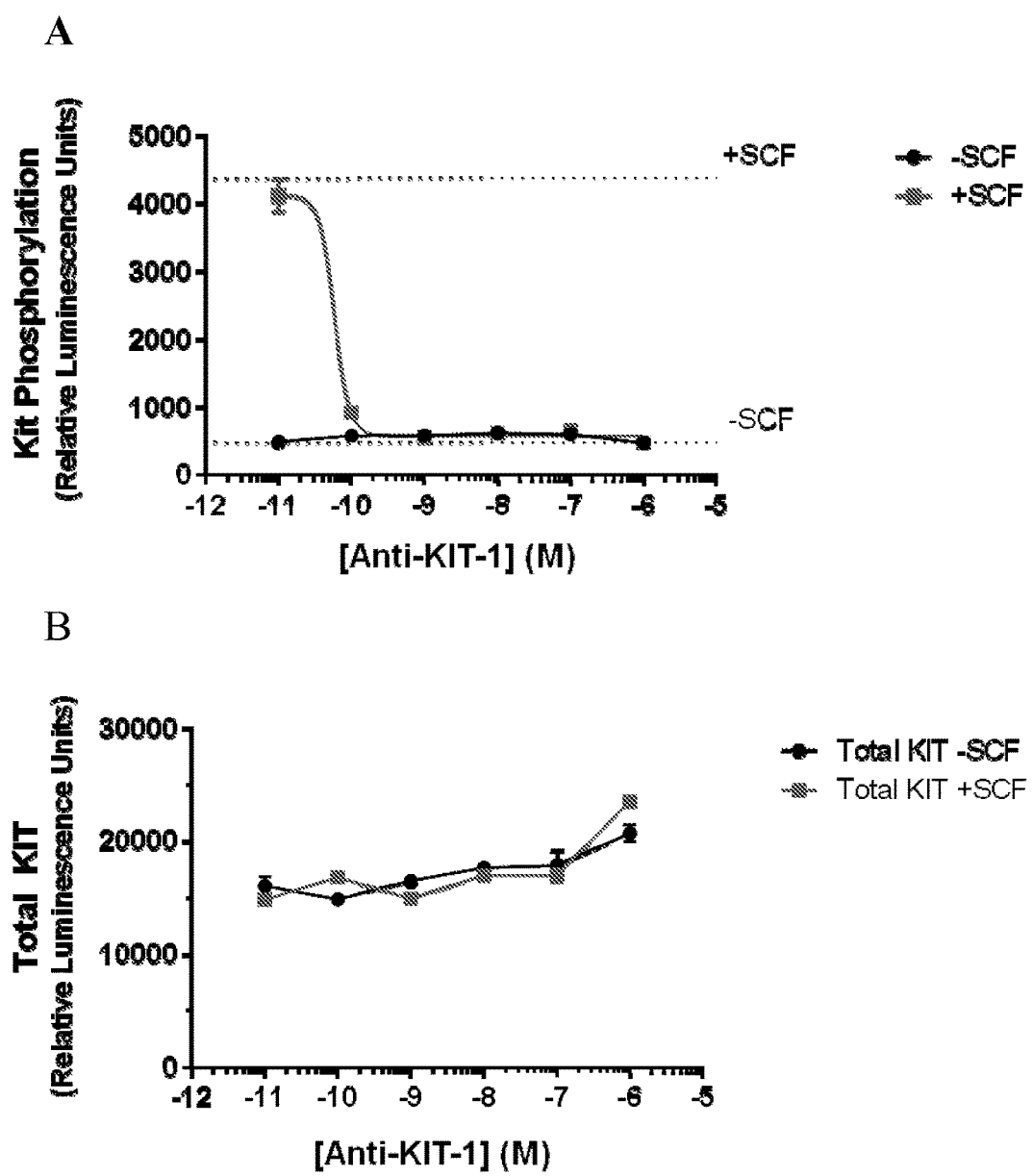

FIG. 8A and FIG. 8B demonstrate the effects of the anti-KIT-1 antibody on (A) SCF-induced KIT phosphorylation and (B) total KIT levels in M-07e cells.

5. DETAILED DESCRIPTION

In one aspect, provided herein are antibodies that specifically bind to a KIT receptor (e.g., human KIT receptor), or an antigen binding fragment thereof, useful in therapeutic methods to prevent, manage or treat an eosinophil or mast cell related disorder, such as an eosinophil or mast cell related disorder of the nervous system, e.g., central nervous system. Non-limiting examples of such disorders include NMO or NMOSD, MS, and NF.

In another aspect, provided herein are methods of preventing, treating, or managing an eosinophil or mast cell related disorder, comprising administering to a subject in need thereof a therapeutically effective amount of an antibody that specifically binds to a KIT receptor (e.g., human KIT receptor), or an antigen binding fragment thereof. In certain aspects, provided herein are methods of alleviating one or more symptoms of an eosinophil or mast cell related disorder, comprising administering to a subject in need thereof a therapeutically effective amount of an antibody that specifically binds to a KIT receptor (e.g., human KIT receptor), or an antigen binding fragment thereof.

In one embodiment, provided herein are methods of preventing, treating, or managing an eosinophil or mast cell related disorder of the nervous system, e.g., central nervous system, comprising administering to a subject in need thereof a therapeutically effective amount of an antibody that specifically binds to a KIT receptor (e.g., human KIT receptor), or an antigen binding fragment thereof. In specific aspects, an eosinophil or mast cell related disorder of the central nervous system is NMO or NMOSD. In another aspect, an eosinophil or mast cell related disorder of the nervous system is NF. In another aspect, an eosinophil or mast cell related disorder of the nervous system is MS. In certain aspects, provided herein are methods of alleviating one or more symptoms of an eosinophil or mast cell related disorder of the nervous system, e.g., central nervous system, comprising administering to a subject in need thereof a therapeutically effective amount of an antibody that specifically binds to a KIT receptor (e.g., human KIT receptor), or an antigen binding fragment thereof.

Antibodies that specifically binds to a KIT receptor (e.g., human KIT receptor as set forth in SEQ ID NO: 1 and FIG. 1), or an antigen binding fragment thereof, for use in the methods provided herein are also described herein, as well as compositions, such as pharmaceutical compositions comprising such antibodies.

As used herein, "administer" or "administration" refers to the act of injecting or otherwise physically delivering a substance (e.g., a humanized anti-KIT antibody provided herein or an antigen-binding fragment thereof) to a subject or a patient (e.g., human), such as by mucosal, topical, intradermal, parenteral, intravenous, intramuscular delivery and/or any other method of physical delivery described herein or known in the art.

As used herein, the terms "effective amount" or "therapeutically effective amount" refer to an amount of a therapy (e.g., an antibody or pharmaceutical composition provided herein) which is sufficient to reduce and/or ameliorate the severity and/or duration of a given disease and/or a symptom related thereto. These terms also encompass an amount necessary for the reduction, slowing, or amelioration of the advancement or progression of a given disease, reduction, slowing, or amelioration of the recurrence, development or onset of a given disease, and/or to improve or enhance the prophylactic or therapeutic effect(s) of another therapy (e.g., a therapy other than an anti-KIT antibody provided herein). In some embodiments, "effective amount" as used herein also refers to the amount of an antibody described herein to achieve a specified result, for example, reduction in the number and/or activity of mast cells, reduction in the number and/or activity of eosinophils, inhibition (e.g., partial inhibition) of a KIT biological activity of a cell, such as inhibition of cell proliferation or cell survival, or enhancement or induction of apoptosis or cell differentiation, and the like.

As used herein, the terms "D4/D5 region" or "D4/D5 domain" refer to a region within a KIT polypeptide spanning the fourth Ig-like extracellular ("D4") domain, the fifth Ig-like extracellular ("D5") domain, and the hinge region in between the D4 and D5 domains ("D4-D5 hinge region"), of KIT, in the following order from the amino terminus to the carboxyl terminus: D4, D4-D5 hinge region, and D5. As used herein, amino acids V308 to H515 of FIG. 1 are considered an example of a D4/D5 region or domain.

As used herein, the terms "KIT" or "KIT receptor" or "KIT polypeptide" refer to any form of full-length KIT including, but not limited to, native KIT, an isoform of KIT, an interspecies KIT homolog, or a KIT variant, e.g., naturally occurring (for example, allelic or splice variant, or mutant, e.g., somatic mutant) or artificially constructed variant (for example, a recombinant or chemically modified variant). KIT is a type III receptor tyrosine kinase encoded by the c-kit gene (see, e.g., Yarden et al., Nature, 1986, 323:226-232; Ullrich and Schlessinger, Cell, 1990, 61:203-212; Clifford et al., J. Biol. Chem., 2003, 278:31461-31464; Yarden et al., EMBO J., 1987, 6:3341-3351; Mol et al., J. Biol. Chem., 2003, 278:31461-31464). GenBank™ accession number NM_000222 provides an exemplary human KIT nucleic acid sequence. GenBank™ accession numbers NP_001087241, P10721, and AAC50969 provide exemplary human KIT amino acid sequences. GenBank™ accession number AAH75716 provides an exemplary murine KIT amino acid sequence. Native KIT comprises five extracellular immunoglobulin (Ig)-like domains (D1, D2, D3, D4, D5), a single transmembrane region, an inhibitory cytoplasmic juxtamembrane domain, and a split cytoplasmic kinase domain separated by a kinase insert segment (see, e.g., Yarden et al., Nature, 1986, 323:226-232; Ullrich and Schlessinger, Cell, 1990, 61:203-212; Clifford et al., J. Biol. Chem., 2003, 278:31461-31464). An exemplary amino acid sequence of the D4/D5 region of human KIT is provided in FIG. 1, at amino acid residues V308 to H515. In a specific embodiment, KIT is human KIT. In a particular embodiment, KIT can exist as a monomer, dimer, multimer, native form, or denatured form.

As used herein, the term "in combination" in the context of the administration of other therapies refers to the use of more than one therapy. The use of the term "in combination" does not restrict the order in which therapies are administered. The therapies may be administered, e.g., serially, sequentially, concurrently, or concomitantly.

As used herein, the terms "manage," "managing," and "management" refer to the beneficial effects that a subject derives from a therapy (e.g., a prophylactic or therapeutic agent), which does not result in a cure of an eosinophil or mast cell related disorder, such as NMO, NMOSD, MS, or NF (e.g., NF1 or NF2). In certain embodiments, a subject is administered one or more therapies (e.g., prophylactic or therapeutic agents, such as an antibody described herein) to "manage" an eosinophil or mast cell related disorder, such as NMO, NMOSD, MS, or NF (e.g., NF1 or NF2), one or more symptoms thereof, so as to prevent the progression or worsening of the disorder.

As used herein, the terms "impede" or "impeding" in the context of an eosinophil or mast cell related disorder, such as NMO, NMOSD, MS, or NF (e.g., NF1 or NF2), refer to the total or partial inhibition (e.g., less than 100%, 95%, 90%, 80%, 70%, 60%, 50%, 40%, 30%, 20%, 10%, or 5%) or blockage of the development, recurrence, onset or spread of an eosinophil or mast cell related disorder, such as NMO, NMOSD, MS, or NF (e.g., NF1 or NF2), and/or symptom related thereto, resulting from the administration of a therapy or combination of therapies provided herein (e.g., a combination of prophylactic or therapeutic agents, such as an antibody described herein).

As used herein, the term "prophylactic agent" refers to any agent that can totally or partially inhibit the development, recurrence, onset or spread of an eosinophil or mast cell related disorder, such as NMO, NMOSD, MS, or NF (e.g., NF1 or NF2), and/or symptom related thereto in a subject. In certain embodiments, the term "prophylactic agent" refers to an antibody described herein. In certain other embodiments, the term "prophylactic agent" refers to an agent other than an antibody described herein. Generally, a prophylactic agent is an agent which is known to be useful to or has been or is currently being used to prevent an eosinophil or mast cell related disorder, such as NMO, NMOSD, MS, or NF (e.g., NF1 or NF2), and/or a symptom related thereto or impede the onset, development, progression and/or severity of an eosinophil or mast cell related disorder, such as NMO, NMOSD, MS, or NF (e.g., NF1 or NF2), and/or a symptom related thereto. In specific embodiments, the prophylactic agent is a human anti-KIT antibody, such as a humanized or a fully human anti-KIT monoclonal antibody.

As used herein, the term "side effects" encompasses unwanted and adverse effects of a therapy (e.g., a prophylactic or therapeutic agent). Unwanted effects are not necessarily adverse. An adverse effect from a therapy (e.g., a prophylactic or therapeutic agent) can be harmful or uncomfortable or risky. Examples of side effects include, diarrhea, cough, gastroenteritis, wheezing, nausea, vomiting, anorexia, abdominal cramping, fever, pain, loss of body weight, dehydration, alopecia, dyspenea, insomnia, dizziness, mucositis, nerve and muscle effects, fatigue, dry mouth, and loss of appetite, rashes or swellings at the site of administration, flu-like symptoms such as fever, chills and fatigue, digestive tract problems and allergic reactions. Additional undesired effects experienced by patients are numerous and known in the art. Many are described in the *Physician's Desk Reference* (63$^{rd}$ ed., 2009).

As used herein, the terms "subject" and "patient" are used interchangeably. As used herein, a subject is a mammal such as a non-primate (e.g., cows, pigs, horses, cats, dogs, goats, rabbits, rats, mice, etc.) or a primate (e.g., monkey and human), for example a human. In one embodiment, the subject is a mammal, e.g., a human, diagnosed with an eosinophil or mast cell related disorder, such as NMO, NMOSD, MS, or NF (e.g., NF1 or NF2). In another embodiment, the subject is a mammal, e.g., a human, at risk of developing an eosinophil or mast cell related disorder, such as NMO, NMOSD, MS, or NF (e.g., NF1 or NF2). In another embodiment, the subject is a non-human primate. In a specific embodiment, the subject is an adult human subject at least 18 years old. In a specific embodiment, the subject is a human child between 1 year old to 18 years old. In a specific embodiment, the subject is a human between 1 year to 3 years old. In a specific embodiment, the subject is a human between 3 years to 12 years old or between 12 years to 18 years old.

As used herein, the terms "therapies" and "therapy" can refer to any protocol(s), method(s), compositions, formulations, and/or agent(s) that can be used in the prevention, treatment, management, or amelioration of a condition or disorder or symptom thereof (e.g., an eosinophil or mast cell related disorder, such as a mast cell related disorder of the nervous system, e.g., central nervous system, for example NMO, NMOSD, MS, or NF (e.g., NF1 or NF2) or one or more symptoms or condition associated therewith). In certain embodiments, the terms "therapies" and "therapy" refer to drug therapy, adjuvant therapy, radiation, surgery, biological therapy, supportive therapy, and/or other therapies useful in treatment, management, prevention, or amelioration of a condition or disorder or one or more symptoms thereof (e.g., an eosinophil or mast cell related disorder, such as a mast cell related disorder of the nervous system, e.g., central nervous system, for example NMO, NMOSD, MS, or NF (e.g., NF1 or NF2) or one or more symptoms or condition associated therewith). In certain embodiments, the term "therapy" refers to a therapy other than an anti-KIT antibody described herein or pharmaceutical composition thereof. In specific embodiments, an "additional therapy" and "additional therapies" refer to a therapy other than a treatment using an anti-KIT antibody described herein or pharmaceutical composition thereof. In a specific embodiment, a therapy includes the use of an anti-KIT antibody described herein as an adjuvant therapy. For example, using an anti-KIT antibody described herein in conjunction with a drug therapy, biological therapy, surgery, and/or supportive therapy.

As used herein, the term "therapeutic agent" refers to any agent that can be used in the treatment, management or amelioration of an eosinophil or mast cell related disorder, such as a mast cell related disorder of the nervous system, e.g., central nervous system, for example NMO, NMOSD, MS, or NF (e.g., NF1 or NF2) and/or a symptom related thereto. In certain embodiments, the term "therapeutic agent" refers to an anti-KIT antibody described herein or an antigen-binding fragment thereof. In certain other embodiments, the term "therapeutic agent" refers to an agent other than an antibody described herein. In specific embodiments, a therapeutic agent is an agent which is known to be useful for, or has been or is currently being used for the treatment, management or amelioration of an eosinophil or mast cell related disorder, such as a mast cell related disorder of the nervous system, e.g., central nervous system, for example NMO, NMOSD, MS, or NF (e.g., NF1 or NF2) or one or more symptoms related thereto.

5.1 Eosinophil and Mast Cell Related Disorders

Mast cells, derived from bone marrow progenitors, are large cells found in connective tissues throughout the body, most abundantly in the submucosal tissues and the dermis. They contain large granules that store a variety of mediator molecules including the vasoactive amine histamine, and have high-affinity Fcε receptors (FcεRI) that allow them to bind IgE monomers. Antigen-binding to IgE bound to mast cells triggers mast-cell degranulation and mast-cell activation, producing a local or systemic immediate hypersensitivity reaction. Therefore, mast cells play important roles in inflammatory and allergic reactions. However, without proper balance and regulation, mast cells can also be responsible for detrimental exaggerated reactions to antigen observed in disorders such as anaphylaxis, atopy, and rhinitis.

Receptor-mediated mast cell activation leads to release of inflammatory mediators, such as, but not limited to, (i) granule-associated mediators, including histamine, serotonin (5-hydroxytryptamine), and a variety of proteases and peptidases; (ii) eicosanoids such as prostaglandin $D_2$ ($PGD_2$) and leukotriene $C_4$ ($LTC_4$); and (iii) cytokines including interleukin-2 (IL-2), IL-3, IL-4, IL-5, IL-6, IL-10, IL-13, granulocyte-macrophage colony-stimulating factor (GM-CSF), and tumor necrosis factor α (TNFα), and chemokines including CCL-2, CCL-3, CCL-5, and CXCL8.

KIT signaling is important for mast cell development and homeostasis, for example, expansion of mast cells from their progenitor cells and their subsequent maturation and survival in their resident tissues, homing of mast cells to their sites of residence in vivo, and promoting adhesion of mast cells to extracellular matrix proteins. Activation mutations of KIT, such as at amino acid residue 816 or 560 of KIT, have been associated with mastocytosis, characterized by overproduction of mast cells, and gastrointestinal stromal cell tumors (GIST).

As used herein, the term "mast cell related disorder" or "mast cell related disorders" refers to disorders where mast cell activity contributes to the pathology and/or mast cells are found in abnormal amounts, such as above-normal amounts or below-normal amounts, in various parts of the body. For example, mast cell related disorders can exhibit accumulation of pathological mast cells in potentially any or all organs and tissues and/or aberrant release of one or more mast cell mediators such as inflammatory mediators. Non-limiting examples of inflammatory mediators released by mast cells include any of: (i) granule-associated mediators, including histamine, serotonin (5-hydroxytryptamine), and a variety of proteases and peptidases; (ii) eicosanoids such as prostaglandin $D_2$ ($PGD_2$) and leukotriene $C_4$ ($LTC_4$); and (iii) cytokines including interleukin-2 (IL-2), IL-3, IL-4, IL-5, IL-6, IL-10, IL-13, granulocyte-macrophage colony-stimulating factor (GM-CSF), and tumor necrosis factor α (TNFα), and chemokines including CCL-2, CCL-3, CCL-5, and CXCL8.

In a specific aspect, a mast cell related disorder is a mast cell related disorder of the nervous system, e.g., central nervous system, such as NMO, NMOSD, MS, or NF (e.g., NF type 1 (NF1), NF type 2 (NF2), or Schwannomatosis).

MS is a chronic inflammatory demyelinating disorder of the central nervous system (brain and spinal cord) involving episodes where white matter within the brain or spinal cord becomes inflamed and then damaged by the individual's own immune system. These inflamed areas become scarred within the brain and spinal cord. The damage disrupts the ability of parts of the nervous system to communicate, resulting in a variety of symptoms, including physical, mental, and/or psychiatric problems. Forms of MS include, but are not limited to, relapsing forms, with symptoms either occurring in isolated attacks, and progressive forms, with symptoms building up over time. Guidelines for diagnosing MS have been described, see, for example, National Collaborating Centre for Chronic Conditions (UK), "Multiple Sclerosis: National Clinical Guideline for Diagnosis and Management in Primary and Secondary Care," London: Royal College of Physicians (UK), 2004, (NICE Clinical Guidelines, No. 8.), available from: http://www.ncbi.nlm.nih.gov/books/NBK48919/. Symptoms of MS can manifest as any neurological symptom or sign such as autonomic, visual, motor, and sensory problems. Non-limiting examples of symptoms of MS include loss of sensitivity or changes in sensation such as tingling, pins and needles or numbness, muscle weakness, very pronounced reflexes, muscle spasms, or difficulty in moving, difficulties with coordination and balance (ataxia), problems with speech or swallowing, visual problems (nystagmus, optic neuritis or double vision), fatigue, acute or chronic pain, bladder and bowel difficulties, emotional problems such as depression or unstable mood, Uhthoff's phenomenon (a worsening of symptoms due to exposure to higher than usual temperatures), and Lhermitte's sign (an electrical sensation that runs down the back when bending the neck). In specific aspects, provided herein are methods for protecting against, treating, alleviating, or managing one or more of these symptoms of MS by administering to a subject in need thereof a therapeutically effective amount of an antibody which specifically binds to KIT (e.g., human KIT) or an antigen binding fragment thereof.

Other non-limiting examples of mast cell related disorders include, for example, anaphylaxis, atopic disease, mast cell activation syndrome, allergic rhinitis, food and venom-related allergies (e.g., tree nut, shellfish, fish, hymenoptera venom or bee sting allergies), psoriasis, atopic dermatitis, rosacea, eczema, tubulointerstitial nephritis, glomerulonephritis, diabetic nephropathy, allograft rejection, amyloidosis, renovascular ischemia, reflux nephropathy, polycystic kidney disease, drug-induced nephropathy, post transplantation fibrosis, and liver fibrosis (e.g. due to alcohol consumption, viral hepatitis B and C, and non-alcoholic steatohepatits (NASH)), parasite infection (e.g., schistosomiasis, amebiasis, echinococcosis), and non-IgE mast cell mediated activation such as angioedema and anaphylaxis.

Eosinophils are white blood cells activated by the lymphocytes of the adaptive immune response and are important in defense against parasitic infections. The level of eosinophils in the blood is normally low, and it can increase markedly in certain situations, such as atopy, which can result in eosinophilia, an abnormally large number of eosinophils in the blood.

As used herein, the term "eosinophil related disorder" or "eosinophil related disorders" refers to disorders that arise when eosinophils are found in abnormal amounts, such as above-normal amounts or below-normal amounts, in various parts of the body. For example, when the body produces too many eosinophils, they can cause chronic inflammation resulting in tissue damage. In certain aspects, an eosinophil disorder may be associated with an abnormal amount of eosinophil in a tissue for a prolonged period of time in response to a trigger. For example, higher amounts of eosinophils may be produced in response to a trigger, such as an infection or allergen, but the high amounts of eosinophils do not decrease at a normal rate and thus are maintained at a high amount for a longer period of time than expected.

Eosinophil related disorders can be diagnosed according to the location where the levels of eosinophils are elevated. Non-limiting examples of eosinophil related disorders include allergic disorders, infectious diseases, blood disorders, immunologic disorders and reactions, endocrine disorders, pulmonary conditions, gastrointestinal disorders, neurologic disorders, rheumatologic disorders, cardiac conditions, and renal diseases. In certain aspects, eosinophilia is an eosinophil related disorder characterized by a peripheral blood eosinophil count greater than a normal level, for example, greater than 450/μL. Eosinophilia can be induced or triggered by a variety of conditions, such as allergy or infection. In particular aspects, elevated levels of eosinophils are observed locally, for example, in the lung, heart, spinal cord, or brain.

Non-limiting examples of neurologic disorders involving eosinophils include central nervous system infections, ventriculoperitoneal shunts, and drug-induced adverse reactions. In certain aspects, an increase in eosinophil count or activity can be detected in cerebrospinal fluid (CSF) or in other samples obtained from tissue of fluid of the central nervous system.

Non-limiting examples of eosinophil or mast cell related indications include upper airway diseases such as allergic rhinitis and sinusitis, foreign body aspiration, glottic stenosis, tracheal stenosis, laryngotracheomalacia, vascular rings, chronic obstructive pulmonary disease (COPD), and congestive heart failure, eosinophilic bronchitis, polychondritis, sarcoidosis, papillomatosis, arthritis (e.g., rheumatoid arthritis) and Wegener's granulomatosis.

In certain embodiments, "eosinophil related disorder" or "eosinophil related disorders" can involve disorders where eosinophil activity contributes to the disorder, e.g., disorders that arise when eosinophils are found in abnormal amounts, such as above-normal amounts or below-normal amounts, in various parts of the body.

In a certain aspect, an anti-KIT antibody or antigen binding fragment thereof described herein or a pharmaceutical composition thereof is administered to a subject in need thereof in accordance with the methods provided herein for treating an eosinophil or mast cell related disorder in the nervous system, e.g., central nervous system, at a dosage and a frequency of administration that achieves one or more of the following in a subject diagnosed with an eosinophil or mast cell related disorder in the nervous system, e.g., central nervous system: reduction in the number and/or activity of eosinophils, reduction in mast cell proliferation, reduction in mast cell number or amount, inhibition or reduction in mast cell activity, reduction in mast cell induced production of inflammatory factors, reduction in production of inflammatory factors, restoration of mast cell homeostasis, reduced mast cell migration, reduced mast cell adhesion, inhibition or reduction in mast cell recruitment of eosinophils, and inhibition or reduction in antigen-mediated degranulation of mast cells.

For example, cell proliferation can be assayed by measuring Bromodeoxyuridine (BrdU) incorporation (see, e.g., Hoshino et al., 1986, Int. J. Cancer 38, 369; Campana et al., 1988, J. Immunol. Meth. 107:79) or (3H) thymidine incorporation (see, e.g., Blechman et al., Cell, 1995, 80:103-113; Chen, J., 1996, Oncogene 13:1395-403; Jeoung, J., 1995, J. Biol. Chem. 270:18367 73), by direct cell count at various time intervals (e.g., 12-hour or 24-hour intervals), or by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as ELISA, Western blotting or immunoprecipitation using antibodies, including commercially available antibodies. mRNA can be quantitated using methods that are well known and routine in the art, for example, using northern analysis, RNase protection, or polymerase chain reaction in connection with reverse transcription.

Cell survival assays are described in the art and can be readily carried out by one of skill in the art. For example, cell viability can be assessed by using trypan-blue staining or other cell death or viability markers known in the art. In a specific embodiment, the level of cellular ATP is measured to determined cell viability. In specific embodiments, cell viability is measured in three-day and seven-day periods using an assay standard in the art, such as the CellTiter-Glo Assay Kit (Promega) which measures levels of intracellular ATP. A reduction in cellular ATP is indicative of a cytotoxic effect. In another specific embodiment, cell viability can be measured in the neutral red uptake assay. In other embodiments, visual observation for morphological changes can include enlargement, granularity, cells with ragged edges, a filmy appearance, rounding, detachment from the surface of the well, or other changes. These changes are given a designation of T (100% toxic), PVH (partially toxic—very heavy—80%), PH (partially toxic—heavy—60%), P (partially toxic—40%), Ps (partially toxic—slight—20%), or 0 (no toxicity—0%), conforming to the degree of cytotoxicity seen. A 50% cell inhibitory (cytotoxic) concentration (IC50) is determined by regression analysis of these data.

Apoptosis assays are described in the art and can be readily carried out by one of skill in the art. For example, flow cytometry can be used to detect activated caspase 3, an apoptosis-mediating enzyme, in cells undergoing apoptosis, or Western blotting can be used to detect cleavage of poly(ADP-ribose) polymerase (PARP) (see, e.g., Smolich et al., Blood, 2001, 97:1413-1421). Cleavage of PARP is an indicator of apoptosis.

Assays to measure mast cell activity, such as release of mediators, from mast cell cultures, such as rodent and human mast cell cultures, have been described (see, e.g., Kuehn et al., "Measuring Mast Cell Mediator Release," in Current Protocols in Immunology, Unite 7.38.1-7.38.9, November 2010 (John Wiley & Sons, Inc.). For example, certain assays are designed to monitor mast cell degranulation through the measurement of the release of the granule component β-hexosaminidase, determination of the generation of products of phospholipid metabolism such as the eicosanoids, leukotriene $C_4$ ($LTC_4$), and prostaglandin $D_2$ ($PGD_2$), or determination of the generation of multiple cytokines. In certain aspects, measurement of mast cell culture release of cytokines can be performed with enzyme-linked immunosorbent assays (ELISAs).

5.1.1 Neuromyelitis Optica and Neuromyelitis Optica Spectrum Disorder

In particular aspects, provided herein are methods of preventing, managing, or treating NMO in a subject, comprising administering to a subject in need thereof an antibody that specifically binds to a KIT receptor (e.g., human KIT receptor), or an antigen binding fragment thereof. In a specific aspect, provided herein is a method of preventing, managing or treating an NMOSD in a subject, comprising administering to a subject in need thereof an antibody that specifically binds to a KIT receptor (e.g., human KIT receptor), or an antigen binding fragment thereof.

Neuromyelitis optica (NMO), or Devic's disease, is an autoimmune inflammatory disorder of the central nervous system that predominantly affects the optic nerves and spinal cord, and also the brain in some cases. NMO can lead to paralysis and blindness. A majority of patients with NMO are seropositive for immunoglobulin autoantibodies (AQP4-IgG or NMO-IgG) against aquaporin-4 (AQP4), a water channel widely expressed in optic nerves, spinal cord, and periventricular regions. A small percentage of NMO patients are NMO-IgG negative.

NMOSD refers to a variety of disorders related to NMO but may not quite meet the clinical diagnostic criteria for definite NMO. Non-limiting examples of disorders that are typically included in this classification of NMOSDs include NMO-IgG seropositive limited forms of NMO (e.g., single or recurrent longitudinally extensive transverse myelitis (LETM) [for example, ≥3 vertebral segment spinal cord lesions seen on MRI), recurrent or simultaneous bilateral optic neuritis (ON)], Asian opticospinal MS (OSMS), optic neuritis or LETM associated with systemic autoimmune disease, and optic neuritis or myelitis associated with brain lesions typical of NMO (e.g., hypothalamic or brainstem lesions) (see, e.g., Oh et al., Neurology Research International, vol. 2012, Article ID 460825, 13 pages, 2012).

In particular aspects, diagnosis criteria for NMO include, but are not limited to, the presence of myelitis and optic neuritis, and any two of the following: (i) extended myelitis on spinal cord MRI, (ii) normal brain MRI at onset, and (iii) positive anti-AQP4 antibodies (see, e.g., Collongues et al., Ther. Adv. Neurol. Disord., 2011, 4:111-121).

In particular aspects, provided herein are methods for alleviating one or more symptoms (e.g., myelitis) of NMO in a subject, comprising administering to a subject in need thereof an antibody that specifically binds to a KIT receptor (e.g., human KIT receptor), or an antigen binding fragment thereof. In a specific aspect, provided herein is a method for alleviating one or more symptoms of NMOSD in a subject, comprising administering to a subject in need thereof an antibody that specifically binds to a KIT receptor (e.g., human KIT receptor), or an antigen binding fragment thereof.

Non-limiting examples of symptoms of NMO or NMOSD include acute optic neuritis (e.g., bilateral), transverse myelitis (e.g., longitudinally extensive), unilateral or bilateral loss of visual acuity, ocular pain, severe paraplegia, asymmetric sensory level, bladder dysfunction, paroxysmal tonic spasms of the trunk and limbs, and Lhermitte's phenomenon. In certain aspects, rostral extension of cervical cord lesions into the cervicomedullary junction can cause symptoms such as acute respiratory decompensation, nausea, intractable vomiting, and hiccups. In some aspects, hypothalamic-pituitary axis dysfunction associated with NMO can manifest as hypersomnolence, hyponatremia, hypothermia, hypothyroidism, and hyperprolactinemia. In addition, confusion, abrupt changes in level of consciousness, cortical blindness, and imaging findings suggestive of posterior reversible encephalopathy syndrome (PRES) also can be associated with NMO.

In particular aspects, methods described herein for preventing, treating or managing NMO or NMOSD or for alleviating one or more symptoms of NMO or NMOSD can achieve one or more of the following:

(i) reduction in pain in the eye;
(ii) improved vision;
(iii) inhibition of vision loss or inhibition of further vision loss;
(iv) reduction in weakness or numbness in the arm or leg;
(v) inhibition of further weakness or numbness in the arm or leg;
(vi) improvement in bladder and/or bowel control;
(vii) reduction in sensory disturbances;
(viii) reduction in, or inhibition of, paralysis.

In specific aspects, methods provided herein can reduce the severity of a symptom of NMO or NMOSD by at least about 10%, 20%, 30%, 40%, 50%, 60%, 70%, or 80%.

In certain aspects, a patient with NMO has recurring episodes/attacks wherein one or more symptoms of NMO manifest for a period of time and then subside. In certain aspects, a patient with NMO may be affected by only one episode. In certain aspects, a patient with NMO may be affected by more than one episodes (e.g., at least 2, 3, 4, or 5) over a period of time (e.g., at least 1 year, 2 years, 3 years, 4, years, 5, years, 10 years, 15 years, 20 years, 25 years, 30 years or more). In certain cases, ambulatory difficulties and/or residual visual deficits are observed in NMO patients following an episode.

Therefore, in certain aspects, provided herein are methods of reducing the number of episodes that manifest in a patient with NMO, comprising administering to a subject in need thereof an antibody that specifically binds to a KIT receptor (e.g., human KIT receptor), or antigen binding fragment thereof. In some aspects, provided herein are methods of reducing the duration of an episode that manifests in a patient with NMO, comprising administering to a subject in need thereof an antibody that specifically binds to a KIT receptor (e.g., human KIT receptor), or antigen binding fragment thereof. In a particular aspect, provided herein are methods of increase the period of time between episodes in a patient with NMO, comprising administering to a subject in need thereof an antibody that specifically binds to a KIT receptor (e.g., human KIT receptor), or antigen binding fragment thereof.

In a certain aspect, an anti-KIT antibody or antigen binding fragment thereof described herein or a pharmaceutical composition thereof is administered to a subject in need thereof in accordance with the methods provided herein for treating NMO or NMOSD provided herein at a dosage and a frequency of administration that achieves one or more of the following in a subject diagnosed with NMO or NMOSD: reduction in the number and/or activity of eosinophils, reduction in mast cell proliferation, reduction in mast cell number or amount, inhibition or reduction in mast cell activity, reduction in mast cell induced production of inflammatory factors, reduction in production of inflammatory factors, restoration of mast cell homeostasis, reduced mast cell migration, reduced mast cell adhesion, inhibition or reduction in mast cell recruitment of eosinophils, and inhibition or reduction in antigen-mediated degranulation of mast cells.

In particular aspects, methods described herein for preventing, managing, or treating NMO comprise administering an antibody which specifically binds to KIT (e.g., human KIT), or an antigen binding fragment thereof, in combination with another therapy for NMO. Non-limiting therapies for NMO include a corticosteroid (e.g., methylprednisolone), an immunosuppressive drug (e.g., azathioprine or cyclophosphamide), anti-CD20 antibody (e.g., rituximab), antibody targeting the complement protein C5 (e.g., eculizumab), and antimetabolites (e.g., methotrexate).

Animal models of NMO have been described (see, e.g., Jones et al., Multiple Sclerosis and Related Disorders, 2002, 1: 174-179), and can be used to confirm and characterize the efficacy of an anti-KIT antibody described herein in methods of treating or managing NMO.

5.1.2 Neurofibromatosis

In particular aspects, provided herein are methods of preventing, managing, or treating NF in a subject, comprising administering to a subject in need thereof an antibody that specifically binds to a KIT receptor (e.g., human KIT receptor), or an antigen binding fragment thereof. In a specific aspect, provided herein is a method of preventing, managing or treating NF type 1 (NF1), NF type 2 (NF2), or Schwannomatosis in a subject, comprising administering to a subject in need thereof an antibody that specifically binds to a KIT receptor (e.g., human KIT receptor), or an antigen binding fragment thereof.

NF is a genetic disorder of the nervous system that primarily affects the development and growth of neural (nerve) tissues, and that causes tumors called neurofibromas to grow along nerves in the body. Although NF generally is an inherited disorder, new cases can arise spontaneously through gene mutation. NF is commonly diagnosed in childhood, approximately around 3-16 years of age, and sometimes in infancy (in children with severe cases).

Non-limiting types of NF include NF type 1 (NF1), NF type 2 (NF2), and Schwannomatosis. NF1 is also known as von Recklinghausen disease. Phenotypic manifestations of NF1 include presence of light brown skin spots at birth or during childhood, neurofibromas (tumors that grow along nerves under the skin, which can also be referred to as dermal neurofibromas), plexiform neurofibromas (tumors involving multiple nerves), spinal cord and optic nerve tumors, and learning disabilities. In certain aspects, an individual affected by NF1 may have a greater probability of developing gastrointestinal stromal tumor (GIST) than the general population. Neurofibromas can be considered external neurofibromas, e.g., cutaneous or dermal neurofibromas, or can be considered internal neurofibromas, e.g., plexiform neurofibromas.

NF2 is an autosomal dominant genetic disorder associated with neurologic, ophthalmologic, and cutaneous abnormalities. Non-limiting examples of NF2 symptoms include hearing loss, tinnitus, visual impairment, imbalance, and painful skin lesions. In certain aspects, skull-base tumors (including vestibular schwannomas (VS) and meningiomas) in NF2 patients because they can lead to lower cranial nerve dysfunction and death.

Diagnosis of NF2 can be established by the presence of bilateral vestibular schwannoma (VS) or unilateral VS in conjunction with the presence of NF2-associated tumors (e.g., meningiomas, schwannomas, ependymomas, glioma, or neurofibroma), posterior cataracts, or a family history of other NF2-related tumors. In addition to the morbidity associated with auditory and vestibular deficits, patients may experience other neurologic dysfunction related to VS growth (e.g., due to compression of other cranial nerves).

Schwannomatosis shares many features with the better-known forms of NF. Multiple schwannomas, or tumors of nerve sheaths, are seen in schwannomatosis, but not the characteristic vestibular (ear nerve) tumors seen in NF2. In certain aspects, patients with schwannomatosis develop tumors on the sheaths, or coverings, of their nerves (see, e.g., MacCollin et al., Neurology, 2005, 64:1838-1845).

Also provided herein are methods of alleviating one or more symptoms of NF (e.g., NF1, NF2 or Schwannomatosis) in a subject, comprising administering to a subject in need thereof an antibody that specifically binds to a KIT receptor (e.g., human KIT receptor), or an antigen binding fragment thereof.

In particular aspects, provided herein is a method of treating neurofibromas in a subject diagnosed with NF (e.g., NF1, NF2 or Schwannomatosis), comprising administering to a subject in need thereof an antibody that specifically binds to a KIT receptor (e.g., human KIT receptor), or an antigen binding fragment thereof.

In specific aspects, provided herein is a method of inhibiting growth of neurofibromas in a subject diagnosed with NF (e.g., NF1, NF2 or Schwannomatosis), comprising administering to a subject in need thereof an antibody that specifically binds to a KIT receptor (e.g., human KIT receptor), or an antigen binding fragment thereof.

In specific aspects, provided herein is a method of protecting against neurofibromas in a subject diagnosed with NF (e.g., NF1, NF2 or Schwannomatosis), comprising administering to a subject in need thereof an antibody that specifically binds to a KIT receptor (e.g., human KIT receptor), or an antigen binding fragment thereof.

In specific aspects, methods provided herein can reduce the severity of one or more symptoms of NF (e.g., NF1, NF2 or Schwannomatosis) in a subject by at least about 10%, 20%, 30%, 40%, 50%, 60%, 70%, or 80%.

In certain aspect, an anti-KIT antibody or antigen binding fragment thereof described herein or a pharmaceutical composition thereof is administered to a subject in need thereof in accordance with the methods provided herein for treating NF (e.g., NF1, NF2 or Schwannomatosis) provided herein at a dosage and a frequency of administration that achieves one or more of the following: reduces or ameliorates the severity of NF and/or a symptom associated therewith in a subject with NF; reduces the number symptoms and/or the duration of a symptom(s) associated with NF in a subject with NF; prevents the onset, progression or recurrence of one or more symptoms associated with NF in a subject with NF; prevents the recurrence of a tumor associated with NF; reduces hearing loss, tinnitus, visual impairment, imbalance, and/or painful skin lesions associated with NF in a subject with NF; improves hearing, hearing function and/or word recognition in a subject with NF; enhances or improves the therapeutic effect of another therapy in a subject with NF or an animal model; reduction or inhibition in the growth of a tumor or neoplasm associated with NF and/or decrease in the tumor size (e.g., volume or diameter) of a tumor associated with NF (e.g., neurofibromas, plexiform neurofibromas, meningiomas, schwannomas, gliomas, or ependymomas) in a subject with NF or an animal model; improvement in neural function, e.g., hearing, balance, tinnitus, or vision; stabilization or reduction of peritumoral inflammation or edema in a subject; and/or improvement in quality of life as assessed by methods well known in the art, e.g., questionnaires.

In a certain aspect, an anti-KIT antibody or antigen binding fragment thereof described herein or a pharmaceutical composition thereof is administered to a subject in need thereof in accordance with the methods provided herein for treating NF (e.g., NF1, NF2 or Schwannomatosis) provided herein at a dosage and a frequency of administration that achieves one or more of the following in a subject diagnosed with NF: reduction in the number and/or activity of eosinophils, reduction in mast cell proliferation, reduction in mast cell number or amount, inhibition or reduction in mast cell activity, reduction in mast cell induced production of inflammatory factors, reduction in production of inflammatory factors, restoration of mast cell homeostasis, reduce mast cell migration, reduce mast cell adhesion, inhibition or reduction in mast cell recruitment of eosinophils, and inhibition or reduction in antigen-mediated degranulation of mast cells.

5.2 Antibodies

Provided herein are antibodies (e.g., anti-KIT antibodies) that specifically bind to a KIT receptor (e.g., extracellular domain of a human KIT receptor for example as set forth in SEQ ID NO: 1 or FIG. 1), or an antigen binding fragment thereof, for use in methods for preventing, treating or managing an eosinophil or mast cell related disorder, such as a mast cell related disorder of the nervous system, e.g., central nervous system, for example NMO, NMOSD, MS, or NF (e.g., NF1 or NF2).

As used herein, the terms "antibody" and "immunoglobulin" and "Ig" are terms of art and can be used interchangeably herein and refer to a molecule with an antigen binding site that immunospecifically binds an antigen.

Antibodies include, for example, monoclonal antibodies, recombinantly produced antibodies, monospecific antibodies, multispecific antibodies (including bispecific antibodies), human antibodies, humanized antibodies, chimeric antibodies, synthetic antibodies, tetrameric antibodies comprising two heavy chain and two light chain molecule, an antibody light chain monomer, an antibody heavy chain monomer, an antibody light chain dimer, an antibody heavy chain dimer, an antibody light chain-antibody heavy chain pair, intrabodies, heteroconjugate antibodies, single domain antibodies, monovalent antibodies, single chain antibodies or single-chain Fvs (scFv), camelized antibodies, affybodies, Fab fragments, F(ab') fragments, disulfide-linked Fvs (sdFv), anti-idiotypic (anti-Id) antibodies (including, e.g., anti-anti-Id antibodies), and epitope-binding fragments of any of the above. In certain embodiments, antibodies described herein refer to polyclonal antibody populations. Antibodies can be of any type (e.g., IgG, IgE, IgM, IgD, IgA or IgY), any class, (e.g., IgG1, IgG2, IgG3, IgG4, IgA1 or IgA2), or any subclass (e.g., IgG2a or IgG2b) of immunoglobulin molecule. In certain embodiments, antibodies described herein are IgG antibodies, or a class (e.g., human IgG1 or IgG4) or subclass thereof.

As used herein, an "antigen" is a moiety or molecule that contains an epitope, and, as such, also is specifically bound by an antibody. In a specific embodiment, the antigen, to which an antibody described herein binds, is KIT (e.g., human KIT), or a fragment thereof, for example, an extracellular domain of KIT (e.g., human KIT) or a D4 region of KIT (e.g., human KIT).

As used herein, the terms "antigen binding domain," "antigen binding region," "antigen binding fragment," and similar terms refer to a portion of an antibody molecule which comprises the amino acid residues that interact with an antigen and confer on the antibody molecule its specificity for the antigen (e.g., the complementarity determining regions (CDR)). The antigen binding region can be derived from any animal species, such as rodents (e.g., mouse, rat or hamster) and humans. The CDRs of an antibody molecule can be determined by any method well known to one of skill in the art. In particular, the CDRs can be determined according to the Kabat numbering system (see Kabat et al. (1991) *Sequences of Proteins of Immunological Interest.* (U.S. Department of Health and Human Services, Washington, D.C.) 5$^{th}$ ed.). In certain aspects, the CDRs of an antibody can be determined according to (i) the Chothia numbering scheme, which will be referred to herein as the "Chothia CDRs" (see, e.g., Chothia and Lesk, 1987, J. Mol. Biol., 196:901-917; Al-Lazikani et al., 1997, J. Mol. Biol., 273:927-948; and U.S. Pat. No. 7,709,226); or (ii) the IMGT numbering system, for example, as described in Lefranc, M.-P., 1999, The Immunologist, 7:132-136 and Lefranc, M.-P. et al., 1999, Nucleic Acids Res., 27:209-212.

As used herein, the term "constant region" or "constant domain" refers to an antibody portion, e.g., a carboxyl terminal portion of a light and/or heavy chain which is not directly involved in binding of an antibody to antigen but which exhibits or contributes to various effector functions, such as interaction with the Fc receptor. The terms refer to a portion of an immunoglobulin molecule having a generally more conserved amino acid sequence relative to an immunoglobulin variable domain.

As used herein, an "epitope" is a term in the art and refers to a localized region of an antigen to which an antibody can specifically bind. A region or a polypeptide contributing to an epitope can be contiguous amino acids of the polypeptide or an epitope can come together from two or more non-contiguous regions of the polypeptide.

As used herein, the term "heavy chain" when used in reference to an antibody refers to any distinct types, e.g., alpha (α), delta (δ), epsilon (ε), gamma (γ) and mu (μ), based on the amino acid sequence of the constant domain, which give rise to IgA, IgD, IgE, IgG and IgM classes of antibodies, respectively, including subclasses of IgG, e.g., IgG$_1$, IgG$_2$, IgG$_3$ and IgG$_4$. In a specific embodiment, the heavy chain is a human heavy chain.

As used herein, the terms "immunospecifically binds," "immunospecifically recognizes," "specifically binds," and "specifically recognizes" are analogous terms in the context of antibodies and refer to molecules that bind to an antigen (e.g., epitope or immune complex) as such binding is understood by one skilled in the art. For example, a molecule that specifically binds to an antigen may bind to other peptides or polypeptides, generally with lower affinity as determined by, e.g., immunoassays, Biacore™, KinExA 3000 instrument (Sapidyne Instruments, Boise, Id.), or other assays known in the art. In a specific embodiment, molecules that immunospecifically bind to an antigen bind to the antigen with a $K_a$ that is at least 2 logs, 2.5 logs, 3 logs, 4 logs or greater than the $K_a$ when the molecules bind to another antigen. In another specific embodiment, molecules that immunospecifically bind to an antigen do not cross react with other proteins. In another specific embodiment, molecules that immunospecifically bind to an antigen do not cross react with other non-KIT proteins.

As used herein, an "isolated" or "purified" antibody is substantially free of cellular material or other contaminating proteins from the cell or tissue source from which the antibody is derived, or substantially free of chemical precursors or other chemicals when chemically synthesized.

The terms "Kabat numbering," and like terms are recognized in the art and refer to a system of numbering amino acid residues in the heavy and light chain variable regions of an antibody, or an antigen binding portion thereof (Kabat et al. (1971) *Ann. NY Acad. Sci.* 190:382-391 and, Kabat et al. (1991) *Sequences of Proteins of Immunological Interest*, Fifth Edition, U.S. Department of Health and Human Services, NIH Publication No. 91-3242). Using the Kabat numbering system, CDRs within an antibody heavy chain molecule are typically present at amino acid positions 31 to 35 ("CDR1"), amino acid positions 50 to 65 ("CDR2"), and amino acid positions 95 to 102 ("CDR3"). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3).

As used herein, the term "light chain" when used in reference to an antibody refers to any distinct types, e.g., kappa (κ) of lambda (λ) based on the amino acid sequence of the constant domains. Light chain amino acid sequences are well known in the art. In specific embodiments, the light chain is a human light chain.

As used herein, the term "monoclonal antibody" refers to an antibody obtained from a population of homogenous or substantially homogeneous antibodies, and each monoclonal antibody will typically recognize a single epitope on the antigen. The term "monoclonal" is not limited to any particular method for making the antibody. Generally, a population of monoclonal antibodies can be generated by cells, a population of cells, or a cell line. In specific embodiments, a "monoclonal antibody," as used herein, is an antibody produced by a single hybridoma or other cell (e.g., host cell producing a recombinant antibody), wherein the antibody immunospecifically binds to a KIT epitope (e.g., an epitope of a D4 of human KIT) as determined, e.g., by ELISA or other antigen-binding or competitive binding assay known in the art or in the Examples provided herein. Monoclonal antibodies described herein can, for example, be made by the hybridoma method as described in Kohler et al.; Nature, 256:495 (1975) or can be isolated from phage libraries using the techniques as described herein, for example. Other methods for the preparation of clonal cell lines and of monoclonal antibodies expressed thereby are well known in the art (see, for example, Chapter 11 in: *Short Protocols in Molecular Biology*, (2002) 5th Ed., Ausubel et al., eds., John Wiley and Sons, New York). In specific embodiments, a monoclonal antibody is a monospecific antibody in that its antigen binding regions are specific for the same epitope. In further specific embodiments, a monoclonal monospecific antibody can be monovalent (having one antigen binding region) or multivalent (having more than one antigen binding regions), for example, bivalent (having two antigen binding regions).

As used herein, the term "naked antibody" refers to an antibody which is not linked, fused or conjugated to another agent or molecule (e.g., label or drug), peptide or polypeptide. In specific embodiments, a naked antibody expressed by a mammalian host cell can be glycosylated by the host cell's glycosylation machinery, for example glycosylation enzymes. In certain embodiment, a naked antibody is not glycosylated when it is expressed by a host cell which does not have its own glycosylation machinery, for example glycosylation enzymes. In certain embodiments, a naked antibody is a whole antibody, and in other embodiments, a naked antibody is an antigen binding fragment of a whole antibody, such as a Fab antibody.

As used herein, the term "polyclonal antibodies" refers to an antibody population that includes a variety of different antibodies directed to the same and to different epitopes within an antigen or antigens. Methods for producing polyclonal antibodies are known in the art (See, e.g., see, for example, Chapter 11 in: *Short Protocols in Molecular Biology*, (2002) 5th Ed., Ausubel et al., eds., John Wiley and Sons, New York).

As used herein, the term "recombinant human antibody" includes human antibodies that are isolated, prepared, expressed, or created by recombinant means, such as antibodies expressed using a recombinant expression vector transfected into a host cell, antibodies isolated from a recombinant, combinatorial human antibody library, antibodies isolated from an animal (e.g., a mouse, rabbit, goat, or cow) that is transgenic and/or transchromosomal for human immunoglobulin genes (see e.g., Taylor, L. D. et al. (1992) *Nucl. Acids Res.* 20:6287-6295) or antibodies prepared, expressed, created or isolated by any other means that involves creation, e.g., via synthesis, genetic engineering of DNA sequences that encode human immunoglobulin sequences, or splicing of sequences that encode human immunoglobulins, e.g., human immunoglobulin gene sequences, to other such sequences. Such recombinant human antibodies can have variable and constant regions derived from human germline immunoglobulin sequences. In certain embodiments, the amino acid sequences of such recombinant human antibodies have been modified such thus the amino acid sequences of the VH and/or VL regions of the recombinant antibodies are sequences that, while derived from and related to human germline VH and VL sequences, do not naturally exist within the human antibody germline repertoire in vivo. As a non-limiting example, a recombinant human antibody can be obtained by assembling several human sequence fragments into a composite human sequence of a recombinant human antibody.

As used herein, the terms "variable region" or "variable domain" refer to a portion of an antibody, generally, a portion of a light or heavy chain, typically about the amino-terminal 110 to 120 amino acids in the mature heavy chain and about 90 to 100 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction of the antibody with antigen. In a specific embodiment, numbering of amino acid positions of antibodies described herein is according to the EU Index, as in Kabat et al. (1991) *Sequences of Proteins of Immunological Interest*, Fifth Edition, U.S. Department of Health and Human Services, NIH Publication No. 91-3242 ("Kabat et al."). In certain aspects, the CDRs of an antibody can be determined according to (i) the Chothia numbering scheme, which will be referred to herein as the "Chothia CDRs" (see, e.g., Chothia and Lesk, 1987, J. Mol. Biol., 196:901-917; Al-Lazikani et al., 1997, J. Mol. Biol., 273:927-948; and U.S. Pat. No. 7,709,226); or (ii) the IMGT numbering system, for example, as described in Lefranc, M.-P., 1999, The Immunologist, 7:132-136 and Lefranc, M.-P. et al., 1999, Nucleic Acids Res., 27:209-212. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs). As a non-limiting example, a variable region described herein is obtained from assembling two or more fragments of human sequences into a composite human sequence.

Antibodies (e.g., anti-KIT antibodies) that specifically bind to a KIT receptor (e.g., human KIT receptor for example as set forth in SEQ ID NO: 1 or FIG. 1), or an antigen binding fragment thereof, have been described. Suitable anti-KIT antibodies for use in the methods provided herein can be selected as described herein.

In a specific aspect, anti-KIT antibodies (e.g., humanized antibodies) or antigen binding fragments thereof for use in methods for preventing, treating or managing an eosinophil or mast cell related disorder, such as a mast cell related disorder of the nervous system, e.g., central nervous system, for example NMO, NMOSD, MS, or NF (e.g., NF1 or NF2), comprise a light chain variable region ("VL") comprising VL CDRs 1-3 as set forth in Table 1 (SEQ ID NOs: 2-4) and a heavy chain variable region ("VH") comprising VH CDRs 1-3 as set forth in Table 1 (SEQ ID NOs: 5-7). In a particular embodiment, such anti-KIT antibody is a naked antibody. In a specific embodiment, such anti-KIT antibody is a bivalent monospecific antibody.

In a certain embodiment, such anti-KIT antibody is not a bispecific antibody.

TABLE 1

CDR Amino Acid Sequences

| | amino acid sequence | SEQ ID NO: |
|---|---|---|
| VL CDR1 | KASQNVRTNVA | 2 |
| VL CDR2 | SASYRYS | 3 |
| VL CDR3 | QQYNSYPRT | 4 |
| VH CDR1 | DYYIN | 5 |
| VH CDR2 | RIYPGSGNTYYNEKFKG | 6 |
| VH CDR3 | GVYYFDY | 7 |

In a particular aspect, an anti-KIT antibody (e.g., humanized antibody) or antigen binding fragment thereof for use in methods for preventing, treating or managing an eosinophil or mast cell related disorder, such as a mast cell related disorder of the nervous system, e.g., central nervous system, for example NMO, NMOSD, MS, or NF (e.g., NF1 or NF2), comprises:

(i) a light chain variable region ("VL") comprising the amino acid sequence:

(SEQ ID NO: 17)
DIVMTQSPSX$_{K1}$LSASVGDRVTITCKASQNVRTNVAWYQQKPGKAP

KX$_{K2}$LIYSASYRYSGVPDRFX$_{K3}$GSGSGTDFTLTISSLQX$_{K4}$EDFAX$_{K5}$

YX$_{K6}$CQQYNSYPRTFGGGTKVEIK, wherein $X_{K1}$ to $X_{K6}$ is any amino acid; and
(ii) a VH comprising the amino acid sequence:

(SEQ ID NO: 18)
QVQLVQSGAEX$_{H1}$KKPGASVKX$_{H2}$SCKASGYTFTDYYINWVX$_{H3}$QAP

GKGLEWIARIYPGSGNTYYNEKFKGRX$_{H4}$TX$_{H5}$TAX$_{H6}$KSTSTAYMX$_{H7}$

LSSLRSEDX$_{H8}$AVYFCARGVYYFDYWGQGTTVTSS, wherein $X_{H1}$ to $X_{H8}$ is any amino acid.

In a particular embodiment, $X_{K1}$ is an amino acid with an aromatic or aliphatic hydroxyl side chain, $X_{K2}$ is an amino acid with an aromatic or aliphatic hydroxyl side chain, $X_{K3}$ is an amino acid with an aliphatic hydroxyl side chain, $X_{K4}$ is an amino acid with an aliphatic hydroxyl side chain or is P, $X_{K5}$ is an amino acid with a charged or acidic side chain, $X_{K6}$ is an amino acid with an aromatic side chain, $X_{H1}$ is an amino acid with an aliphatic side chain, $X_{H2}$ is an amino acid with an aliphatic side chain, $X_{H3}$ is an amino acid with a polar or basic side chain, $X_{H4}$ is an amino acid with an aliphatic side chain, $X_{H5}$ is an amino acid with an aliphatic side chain, $X_{H6}$ is an amino acid with an acidic side chain, $X_{H7}$ is an amino acid with an acidic or amide derivative side chain, and $X_{H8}$ is an amino acid with an aliphatic hydroxyl side chain.

In a specific embodiment, $X_{K1}$ is the amino acid F or S, $X_{K2}$ is the amino acid A or S, $X_{K3}$ is the amino acid T or S, $X_{K4}$ is the amino acid S or P, $X_{K5}$ is the amino acid D or T, $X_{K6}$ is the amino acid F or Y, $X_{H1}$ is the amino acid L or V, $X_{H2}$ is the amino acid L or V, $X_{H3}$ is the amino acid K or R, $X_{H4}$ is the amino acid V or A, $X_{H5}$ is the amino acid L or I, $X_{H6}$ is the amino acid E or D, $X_{H7}$ is the amino acid Q or E, and $X_{H8}$ is the amino acid S or T.

In a specific aspect, anti-KIT antibodies (e.g., humanized antibodies) or antigen binding fragments thereof for use in methods for preventing, treating or managing an eosinophil or mast cell related disorder, such as a mast cell related disorder of the nervous system, e.g., central nervous system, for example NMO, NMOSD, MS, or NF (e.g., NF1 or NF2), comprise a heavy chain variable region ("VH") comprising an amino acid sequence selected from Table 2 (SEQ ID NOs: 8-12) and/or a light chain variable region ("VL") comprising an amino acid sequence selected from Table 3 (SEQ ID NOs: 13-16). In a particular embodiment, such anti-KIT antibody is a naked antibody. In a specific embodiment, such anti-KIT antibody is a bivalent monospecific antibody. In a certain embodiment, such anti-KIT antibody is not a bispecific antibody.

TABLE 2

VH amino acid sequence

| | Amino Acid Sequence | SEQ ID NO: |
|---|---|---|
| VH1 | Q V Q L V Q S G A E L K K P G A S V K L S C K A S G Y T F T D Y Y I N W V K Q A P G K G L E W I A R I Y P G S G N T Y Y N E K F K G R A T L T A E K S T S T A Y M Q L S S L R S E D S A V Y F C A R G V Y Y F D Y W G Q G T T V T V S S | 8 |
| VH2 | Q V Q L V Q S G A E V K K P G A S V K L S C K A S G Y T F T D Y Y I N W V K Q A P G K G L E W I A R I Y P G S G N T Y Y N E K F K G R A T L T A E K S T S T A Y M Q L S S L R S E D T A V Y F C A R G V Y Y F D Y W G Q G T T V T V S S | 9 |
| VH3 | Q V Q L V Q S G A E V K K P G A S V K L S C K A S G Y T F T D Y Y I N W V R Q A P G K G L E W I A R I Y P G S G N T Y Y N E K F K G R A T L T A D K S T S T A Y M Q L S S L R S E D T A V Y F C A R G V Y Y F D Y W G Q G T T V T V S S | 10 |
| VH4 | Q V Q L V Q S G A E V K K P G A S V K V S C K A S G Y T F T D Y Y I N W V R Q A P G K G L E W I A R I Y P G S G N T Y Y N E K F K G R A T I T A D K S T S T A Y M E L S | 11 |

TABLE 2 -continued

VH amino acid sequence

| | Amino Acid Sequence | SEQ ID NO: |
|---|---|---|
| | S L R S E D T A V Y F C A R G V Y Y F D Y W G Q G T T V T V S S | |
| VH5 | Q V Q L V Q S G A E V K K P G A S V K V S C K A S G Y T F T D Y Y I N W V R Q A P G K G L E W I A R I Y P G S G N T Y Y N E K F K G R V T I T A D K S T S T A Y M E L S S L R S E D T A V Y F C A R G V Y Y F D Y W G Q G T T V T V S S | 12 |

TABLE 3

VL Amino Acid Sequence

| | Amino Acid Sequence | SEQ ID NO: |
|---|---|---|
| VL1 | D I V M T Q S P S F L S A S V G D R V T I T C K A S Q N V R T N V A W Y Q Q K P G K A P K A L I Y S A S Y R Y S G V P D R F T | 13 |
| VL2 | G S G S G T D F T L T I S S L Q S E D F A D Y F C Q Q Y N S Y P R T F G G G T K V E I K D I V M T Q S P S S L S A S V G D R V T I T C K A S Q N V R T N V A W Y Q Q K P G K A P K A L I Y S A S Y R Y S G V P D R F T G S G S G T D F T L T I S S L Q P E D F A D Y F C Q Q Y N S Y P R T F G G G T K V E I K | 14 |
| VL3 | D I V M T Q S P S S L S A S V G D R V T I T C K A S Q N V R T N V A W Y Q Q K P G K A P K A L I Y S A S Y R Y S G V P D R F S G S G S G T D F T L T I S S L Q P E D F A D Y F C Q Q Y N S Y P R T F G G G T K V E I K | 15 |
| VL4 | D I V M T Q S P S S L S A S V G D R V T I T C K A S Q N V R T N V A W Y Q Q K P G K A P K S L I Y S A S Y R Y S G V P D R F S G S G S G T D F T L T I S S L Q P E D F A T Y Y C Q Q Y N S Y P R T F G G G T K V E I K | 16 |

In a specific aspect, anti-KIT antibodies (e.g., humanized antibodies) or antigen binding fragments thereof for use in methods for preventing, treating or managing an eosinophil or mast cell related disorder, such as a mast cell related disorder of the nervous system, e.g., central nervous system, for example NMO, NMOSD, MS, or NF (e.g., NF1 or NF2), comprise a VH comprising the amino acid sequence of SEQ ID NO: 8, and/or a VL comprising the amino acid sequence of SEQ ID NO: 13. In one embodiment, the anti-KIT antibody or antigen binding fragment thereof comprises a VH comprising the amino acid sequence of SEQ ID NO: 8, and/or a VL comprising the amino acid sequence of SEQ ID NO: 14. In one embodiment, the anti-KIT antibody or antigen binding fragment thereof comprises a VH comprising the amino acid sequence of SEQ ID NO: 8, and/or a VL comprising the amino acid sequence of SEQ ID NO: 15. In one embodiment, the anti-KIT antibody or antigen binding fragment thereof comprises a VH comprising the amino acid sequence of SEQ ID NO: 8, and/or a VL comprising the amino acid sequence of SEQ ID NO: 16.

In one embodiment, the anti-KIT antibody or antigen binding fragment thereof comprises a VH comprising the amino acid sequence of SEQ ID NO: 9, and/or a VL comprising the amino acid sequence of SEQ ID NO: 13. In one embodiment, the anti-KIT antibody or antigen binding fragment thereof comprises a VH comprising the amino acid sequence of SEQ ID NO: 9, and/or a VL comprising the amino acid sequence of SEQ ID NO: 14. In one embodiment, the anti-KIT antibody or antigen binding fragment thereof comprises a VH comprising the amino acid sequence of SEQ ID NO: 9, and/or a VL comprising the amino acid sequence of SEQ ID NO: 15. In one embodiment, the anti-KIT antibody or antigen binding fragment thereof comprises a VH comprising the amino acid sequence of SEQ ID NO: 9, and/or a VL comprising the amino acid sequence of SEQ ID NO: 16.

In one embodiment, the anti-KIT antibody or antigen binding fragment thereof comprises a VH comprising the amino acid sequence of SEQ ID NO: 10, and/or a VL comprising the amino acid sequence of SEQ ID NO: 13. In one embodiment, the anti-KIT antibody or antigen binding fragment thereof comprises a VH comprising the amino acid sequence of SEQ ID NO: 10, and/or a VL comprising the amino acid sequence of SEQ ID NO: 14. In one embodiment, the anti-KIT antibody or antigen binding fragment thereof comprises a VH comprising the amino acid sequence of SEQ ID NO: 10, and/or a VL comprising the amino acid sequence of SEQ ID NO: 15. In one embodiment, the anti-KIT antibody or antigen binding fragment thereof comprises a VH comprising the amino acid sequence of SEQ ID NO: 10, and/or a VL comprising the amino acid sequence of SEQ ID NO: 16.

In one embodiment, the anti-KIT antibody or antigen binding fragment thereof comprises a VH comprising the amino acid sequence of SEQ ID NO: 11, and/or a VL comprising the amino acid sequence of SEQ ID NO: 13. In one embodiment, the anti-KIT antibody or antigen binding fragment thereof comprises a VH comprising the amino acid sequence of SEQ ID NO: 11, and/or a VL comprising the amino acid sequence of SEQ ID NO: 14. In one embodiment, the anti-KIT antibody or antigen binding fragment thereof comprises a VH comprising the amino acid sequence of SEQ ID NO: 11, and/or a VL comprising the amino acid sequence of SEQ ID NO: 15. In one embodiment, the anti-KIT antibody or antigen binding fragment thereof comprises a VH comprising the amino acid sequence of SEQ ID NO: 11, and/or a VL comprising the amino acid sequence of SEQ ID NO: 16.

In one embodiment, the anti-KIT antibody or antigen binding fragment thereof comprises a VH comprising the amino acid sequence of SEQ ID NO: 12, and/or a VL comprising the amino acid sequence of SEQ ID NO: 13. In one embodiment, the anti-KIT antibody or antigen binding fragment thereof comprises a VH comprising the amino acid sequence of SEQ ID NO: 12, and/or a VL comprising the amino acid sequence of SEQ ID NO: 14. In one embodiment, the anti-KIT antibody or antigen binding fragment thereof comprises a VH comprising the amino acid sequence of SEQ ID NO: 12, and/or a VL comprising the amino acid sequence of SEQ ID NO: 15. In one embodiment, the anti-KIT antibody or antigen binding fragment thereof comprises a VH comprising the amino acid sequence of SEQ ID NO: 12, and/or a VL comprising the amino acid sequence of SEQ ID NO: 16.

In certain aspects, anti-KIT antibodies or antigen binding fragments thereof for use in methods for preventing, treating or managing an eosinophil or mast cell related disorder, such as a mast cell related disorder of the nervous system, e.g., central nervous system, for example NMO, NMOSD, MS, or NF (e.g., NF1 or NF2), have been described or can be readily obtained using methods known in the art, for example, see Section 5.2.1 below.

In a particular aspect, an anti-KIT antibody or an antigen binding fragment thereof for use in methods provided herein specifically binds to a D4 domain of human KIT and a D4/D5 region of KIT, e.g., human KIT. In another specific embodiment, an anti-KIT antibody or an antigen binding fragment thereof for use in methods provided herein specifically binds to a D5 domain of KIT, e.g., human KIT, with lower affinity than to a D4 domain of KIT, e.g., human KIT. In a particular embodiment, an anti-KIT antibody or an antigen binding fragment thereof for use in methods provided herein specifically binds to a D4 domain of KIT, e.g., human KIT, with higher affinity than to a D5 domain of KIT, e.g., human KIT; for example, the higher affinity is at least 1 fold, 2 fold, 3 fold, 4 fold, 5 fold, 10 fold, 20 fold, 50 fold, 100 fold, 500 fold, or 1000 fold as determined by methods known in the art, e.g., ELISA or Biacore assays.

In a particular embodiment, an anti-KIT antibody or an antigen binding fragment thereof for use in methods provided herein specifically binds to a D4 or D4/D5 region of KIT, e.g., human KIT, and has at least 1 fold, 2 fold, 3 fold, 4 fold, 5 fold, or 10 fold higher affinity for a KIT antigen consisting essentially of a D4 domain only than a KIT antigen consisting essentially of a D5 domain only.

In a particular embodiment, an anti-KIT antibody or an antigen binding fragment thereof for use in methods provided herein specifically binds to a KIT polypeptide (e.g., the D4 region of human KIT) with an $EC_{50}$ (half maximal effective concentration) value of about 50 nM, 10 nM, 500 pM, 300 pM, 200 pM, 100 pM or 50 pM or less as determined by an assay described in the art, such as ELISA.

In a particular embodiment, an anti-KIT antibody or an antigen binding fragment thereof for use in methods provided herein specifically binds to a KIT polypeptide (e.g., the D4 region of human KIT) with an $EC_{50}$ value of about 200 pM or 150 pM or less as determined by an assay described in the art, such as ELISA or FACs with CHO-WT-KIT cells (CHO cells engineered to recombinantly express wild-type human KIT).

In a particular embodiment, an anti-KIT antibody or an antigen binding fragment thereof for use in methods provided herein specifically binds to a KIT polypeptide (e.g., the D4 region of human KIT), is capable of blocking KIT phosphorylation with $IC_{50}$ (50% inhibition concentration) value of about 600 pM or less.

In particular embodiments, an anti-KIT antibody or an antigen binding fragment thereof for use in methods provided herein does not bind the extracellular ligand binding site of KIT, e.g., the SCF binding site of KIT. In particular embodiments, an anti-KIT antibody or an antigen binding fragment thereof for use in methods provided herein does not inhibit ligand binding to KIT, e.g., does not inhibit KIT ligand (e.g., SCF) binding to KIT, as determined by a method described in the art, for example, ELISA. In certain embodiments, an anti-KIT antibody or an antigen binding fragment thereof for use in methods provided herein does not fully inhibit, or partially inhibits, ligand binding to KIT, e.g., does not fully inhibit, or partially inhibits, KIT ligand (e.g., SCF) binding to KIT, as determined by a method described in the art, for example, ELISA or FACS (fluorescence-activated cell sorting).

In specific aspects, anti-KIT antibodies (e.g., human or humanized antibodies) for use in the methods provided herein are inhibitory antibodies, that is, antibodies that inhibit (e.g., partially inhibit) KIT activity, i.e., one or more KIT activities. In a specific embodiment, partial inhibition of a KIT activity results in, for example, about 25% to about 65% or 75% inhibition. In a specific embodiment, partial inhibition of a KIT activity results in, for example, about 35% to about 85% or 95% inhibition. Non-limiting examples of KIT activities include KIT dimerization, KIT phosphorylation (e.g., tyrosine phosphorylation), signaling downstream of KIT (e.g., Stat, AKT, MAPK, or Ras signaling), induction or enhancement of gene transcription (e.g., c-Myc), induction or enhancement of cell proliferation or cell survival. In a particular embodiment, an antibody described herein inhibits KIT phosphorylation (e.g., ligand-induced phosphorylation).

In a specific embodiment, an anti-KIT antibody or an antigen binding fragment thereof for use in methods provided herein inhibits KIT tyrosine phosphorylation in the KIT cytoplasmic domain.

In another particular embodiment, an anti-KIT antibody or an antigen binding fragment thereof for use in methods provided herein inhibits cell proliferation, for example, mast cell proliferation or eosinophil proliferation. In yet another particular embodiment, an anti-KIT antibody or an antigen binding fragment thereof for use in methods provided herein inhibits cell survival, for example mast cell survival or eosinophil cell survival. In certain aspects, inhibition of cell proliferation, for example, mast cell proliferation or eosinophil proliferation, is at least 10%, 20%, 30%, 40%, 50%, 60%, 70%, 80%, or 90%.

In another particular embodiment, an anti-KIT antibody or an antigen binding fragment thereof for use in methods provided herein inhibits mast cell activation or eosinophil activation. In certain aspects, inhibition of mast cell activation or activity or eosinophil activation or activity, is at least 10%, 20%, 30%, 40%, 50%, 60%, 70%, 80%, or 90%.

In a specific embodiment, an anti-KIT antibody or an antigen binding fragment thereof for use in methods provided herein inhibits eosinophil or mast cell degranulation (see, e.g., Staats et al., 2012, Med. Chem. Commun., 2013, 4:88-94; and Ochkur et al., 2012, J. Immunol. Methods, 384:10-20). In certain aspects, inhibition of eosinophil or mast cell degranulation is at least 10%, 20%, 30%, 40%, 50%, 60%, 70%, 80%, or 90%.

In another particular embodiment, an anti-KIT antibody or an antigen binding fragment thereof for use in methods provided herein inhibits mast cell mediator release. In certain aspects, mast cell mediator release is at least 10%, 20%, 30%, 40%, 50%, 60%, 70%, 80%, or 90%. Assays to measure mast cell activity, such as release of mediators, from mast cell cultures, such as rodent and human mast cell cultures, have been described (see, e.g., Kuehn et al., "Measuring Mast Cell Mediator Release," in Current Protocols in Immunology, Unite 7.38.1-7.38.9, November 2010 (John Wiley & Sons, Inc.). In certain aspects, $CD34^+$ peripheral blood progenitor cells or a mast cell line, such as HMC-1 or human LAD2 mast cell line can be used in these assays to ascertain the effects of an anti-KIT antibody on mast cells.

In a specific embodiment, an anti-KIT antibody or an antigen binding fragment thereof for use in methods provided herein induces apoptosis, for example mast cell apoptosis or eosinophil apoptosis. In another specific embodiment, an anti-KIT antibody or an antigen binding fragment thereof for use in methods provided herein induces cell differentiation, e.g., mast cell differentiation.

In a particular embodiment, an anti-KIT antibody or an antigen binding fragment thereof for use in methods provided herein can achieve any one of the following: reduction in the number and/or activity of eosinophils, reduction in mast cell proliferation, reduction in mast cell number or amount, inhibition or reduction in mast cell activity, reduction in mast cell induced production or release of inflammatory factors, reduction in release of inflammatory factors, restoration of mast cell homeostasis, reduced mast cell migration, reduced mast cell adhesion, inhibition or reduction in mast cell recruitment of eosinophils, and inhibition or reduction in antigen-mediated degranulation of mast cells.

In a particular embodiment, an anti-KIT antibody or an antigen binding fragment thereof for use in methods provided herein inhibits KIT activity but does not inhibit KIT dimerization. In another particular embodiment, an anti-KIT antibody or an antigen binding fragment thereof for use in methods provided herein inhibits KIT activity and does not inhibit ligand binding to KIT, e.g., does not inhibit KIT ligand (e.g., SCF) binding to KIT, but does inhibit KIT dimerization.

In a particular embodiment, an anti-KIT antibody or an antigen binding fragment thereof for use in methods provided herein inhibits a KIT activity, such as ligand-induced tyrosine phosphorylation of a KIT cytoplasmic domain, by about 25% to about 65% or 75%, as determined by a cell-based phosphorylation assay well known in the art, for example, the cell-based phosphorylation assay described herein. In a certain embodiment, an anti-KIT antibody or an antigen binding fragment thereof for use in methods provided herein inhibits a KIT activity, such as ligand-induced tyrosine phosphorylation of a KIT cytoplasmic domain, by about 35% to about 85% or 95%, as determined by a cell-based phosphorylation assay well known in the art, for example, the cell-based phosphorylation assay described herein.

In a particular embodiment, an anti-KIT antibody or an antigen binding fragment thereof for use in methods provided herein inhibits a KIT activity, such as ligand-induced tyrosine phosphorylation of a KIT cytoplasmic domain, with a 50% inhibition concentration ($IC_{50}$) of less than about 600 pM, or less than about 500 pM, or less than about 250 pM, as determined by a cell-based phosphorylation assay well known in the art, for example, the cell-based phosphorylation assay described herein. In a specific embodiment, the $IC_{50}$ is less than about 550 pM or 200 pM. In a specific embodiment, the $IC_{50}$ is in the range of about 50 pM to about 225 pM, or in the range of 100 pM to about 600 pM. In a specific embodiment, the $IC_{50}$ is in the range of about 50 pM to about 550 pM, or about 50 pM to about 600 pM, or about 150 pM to about 550 pM.

In a specific embodiment, an anti-KIT antibody or an antigen binding fragment thereof for use in methods provided herein, (i) immunospecifically binds to a KIT polypeptide comprising the D4 region of human KIT, (ii) inhibits KIT phosphorylation (e.g., tyrosine phosphorylation), and (iii) does not fully inhibit, or partially inhibits, KIT ligand (e.g., SCF) binding to KIT. In yet another specific embodiment, such an antibody does not inhibit KIT dimerization. In yet another specific embodiment, such an antibody can be recombinantly expressed by CHO cells at an average titer of at least 0.5 µg/mL, for example at least 1.0 µg/mL. In a further specific embodiment, such an antibody comprises a VH domain and a VL domain that are non-immunogenic, for example, the VH domain and VL domain do not contain T cell epitopes.

In other specific embodiments, an anti-KIT antibody or an antigen binding fragment thereof for use in methods provided herein immunospecifically binds to a monomeric form of KIT (e.g., human KIT). In particular embodiments, an anti-KIT antibody or an antigen binding fragment thereof for use in methods provided herein specifically bind to a monomeric form of KIT (e.g., human KIT). In specific embodiments, an anti-KIT antibody or an antigen binding fragment thereof for use in methods provided herein specifically binds to a dimeric form of KIT (e.g., human KIT).

In specific embodiments, an anti-KIT antibody or an antigen binding fragment thereof for use in methods provided herein does not bind to a monomeric form of KIT and specifically binds to a dimeric form of KIT or multimeric form of KIT. In certain embodiments, an antibody has higher affinity for a KIT monomer than a KIT dimer. In certain embodiments, an antibody has higher affinity for a KIT monomer than a KIT multimer.

In specific embodiments, an anti-KIT antibody or an antigen binding fragment thereof for use in methods provided herein specifically binds to a native isoform or native variant of KIT (that is a naturally occurring isoform or variant of KIT in an animal (e.g., monkey, mouse, goat, donkey, dog, cat, rabbit, pig, rat, human, frog, or bird) that can be isolated from an animal, preferably a human). In particular embodiments, an anti-KIT antibody or an antigen binding fragment thereof for use in methods provided herein specifically binds to human KIT or a fragment thereof In specific embodiments, an anti-KIT antibody or an antigen binding fragment thereof for use in methods provided herein specifically binds to human KIT or a fragment thereof and does not specifically bind to a non-human KIT (e.g., monkey, mouse, goat, donkey, dog, cat, rabbit, pig, rat, or bird) or a fragment thereof. In specific embodiments, an anti-KIT antibody or an antigen binding fragment thereof for use in methods provided herein specifically binds to human KIT or a fragment thereof and does not specifically bind to murine KIT. In certain embodiments, an anti-KIT antibody or an antigen binding fragment thereof for use in methods provided herein specifically binds to human KIT or a fragment thereof (e.g., a D4 region of human KIT) and to canine (dog) and non-human primate (e.g., monkey) KIT. In certain embodiments, an anti-KIT antibody or an antigen binding fragment thereof for use in methods provided herein specifically binds to human KIT or a fragment thereof (e.g., a D4 region of human KIT) and to canine (dog) and non-human primate (e.g., monkey) KIT, but does not specifically bind to murine or rat KIT or a fragment thereof (e.g., a D4 region of murine KIT).

In certain embodiments, an anti-KIT antibody or an antigen binding fragment thereof for use in methods provided herein specifically binds to human KIT or a fragment thereof (e.g., a D4 region of human KIT) and to canine (dog), feline (cat) and cynomologous KIT, but does not specifically bind to murine or rat KIT or a fragment thereof (e.g., a D4 region of murine KIT).

In specific embodiments, an anti-KIT antibody or an antigen binding fragment thereof for use in methods provided herein specifically binds to human KIT or a fragment thereof (e.g., a D4 region of human KIT), and to canine (dog), feline (cat) and cynomologous KIT, with high affinity (e.g., at least 0.5 fold, 1 fold, 2 fold, 3 fold, 4 fold, 5 fold, or 10 fold) than to murine or rat KIT or a fragment thereof (e.g., a D4 region of murine KIT).

In certain embodiments, an anti-KIT antibody or an antigen binding fragment thereof for use in methods provided herein specifically binds to an extracellular domain of human KIT comprising a mutation, for example a somatic mutation, such as a mutation in exon 9 of human KIT wherein the Ala and Tyr residues at positions 502 and 503 are duplicated (see, e.g., Marcia et al., (2000) Am. J. Pathol. 156(3):791-795; and Debiec-Rychter et al., (2004) European Journal of Cancer. 40:689-695, which are both incorporated herein by reference in their entireties, describing KIT mutations).

In certain embodiments, an anti-KIT antibody or an antigen binding fragment thereof for use in methods provided herein specifically binds to an extracellular domain of human KIT which is glycosylated. In certain embodiments, an antibody described herein or antigen-binding fragment thereof binds to two different glycosylated forms of an extracellular domain of human KIT. For example, two forms of human KIT with different molecular weights, indicating different glycosylation patterns, have been observed by immunoblotting. In certain embodiments, an antibody described herein may specifically bind to both of these forms of human KIT which have different glycosylation patterns, e.g., one form is more glycosylated than the other. In certain embodiments, an antibody described herein or antigen-binding fragment thereof binds to an extracellular domain of human KIT which is not glycosylated.

In a specific embodiment, an anti-KIT antibody or antigen binding fragment thereof for use in the methods provided herein is a bivalent monospecific antibody, in that it has two antigen binding regions (e.g., two identical antigen binding regions) and both antigen binding regions specifically bind the same antigen, KIT (e.g., human KIT). In certain embodiments, the antigen binding region comprises the VH and VL CDRs as set forth in Table 1. In particular embodiments, the antigen binding region comprises a VH comprising the amino acid sequence of any one of SEQ ID NOs: 8-12, and/or a VL comprising the amino acid sequence of any one of SEQ ID NOs: 13-16. In certain aspects, an anti-KIT antibody or antigen binding fragment thereof for use in the methods provided herein is not a bispecific antibody.

In a particular embodiment, an anti-KIT antibody for use in the methods provided herein is a Fab fragment that immunospecifically binds to a KIT polypeptide, such as the D4 region of KIT. In a specific embodiment, antibodies for use in the methods described herein are monoclonal antibodies or isolated monoclonal antibodies. In another specific embodiment, an antibody for use in the methods described herein is a humanized monoclonal antibody. In a particular embodiment, an antibody for use in the methods described herein is a recombinant antibody, for example, a recombinant human antibody, recombinant humanized antibody or a recombinant monoclonal antibody. In certain embodiments, an antibody for use in the methods described herein contains non-human amino acid sequences, e.g., non-human CDRs or non-human (e.g., non-human primate) framework residues.

In particular embodiments provided herein, recombinant antibodies can be isolated, prepared, expressed, or created by recombinant means, such as antibodies expressed using a recombinant expression vector transfected into a host cell, antibodies isolated from a recombinant, combinatorial antibody library, or antibodies prepared, expressed, created or isolated by any other means that involves creation, e.g., via synthesis, genetic engineering of DNA sequences that encode human immunoglobulin sequences, or splicing of sequences that encode human immunoglobulins, e.g., human immunoglobulin gene sequences, to other such sequences. In certain embodiments, the amino acid sequences of such recombinant antibodies have been modified such thus the amino acid sequences of such antibodies, e.g., VH and/or VL regions, are sequences that do not naturally exist within an organism's antibody germline repertoire in vivo, for example a murine or human germline repertoire. In a particular embodiment, a recombinant antibody can be obtained by assembling several sequence fragments that naturally exist in an organism (e.g., primate, such as human) into a composite sequence of a recombinant antibody, wherein the composite sequence does not naturally exist within an organism (e.g., primate such as human).

Antibodies for use in the methods provided herein include immunoglobulin molecules of any type (e.g., IgG, IgE, IgM, IgD, IgA and IgY), class (e.g., IgG1, IgG2, IgG3, IgG4, IgA1 and IgA2) or subclass of immunoglobulin molecule. In a specific embodiment, an antibody for use in the methods provided herein is an IgG antibody (e.g., human IgG antibody), or a class (e.g., human IgG1 or IgG4) or subclass thereof. In another specific embodiment, an antibody for use in the methods described herein is an IgG1 (e.g., human IgG1 (isotype a, z, or f)) or IgG4 antibody. In certain embodiments, an antibody for use in the methods described herein is a whole or entire antibody, e.g., a whole or entire humanized, human, or composite human antibody.

Antibodies provided herein can include antibody fragments that retain the ability to specifically bind to an antigen, e.g., KIT epitope (e.g., a KIT epitope within a KIT polypeptide containing a D4 region of human KIT). In a specific embodiment, fragments include Fab fragments (an antibody fragment that contains the antigen-binding domain and comprises a light chain and part of a heavy chain (i.e., the VH and CH1 domains of a heavy chain) bridged by a disulfide bond); Fab' (an antibody fragment containing a single antigen-binding domain comprising an Fab and an additional portion of the heavy chain through the hinge region); $F(ab')_2$ (two Fab' molecules joined by interchain disulfide bonds in the hinge regions of the heavy chains; the Fab' molecules can be directed toward the same or different epitopes); a bispecific Fab (a Fab molecule having two antigen binding domains, each of which can be directed to a different epitope); a single chain Fab chain comprising a variable region, also known as a sFv (the variable, antigen-binding determinative region of a single light and heavy chain of an antibody linked together by a chain of 10-25 amino acids); a disulfide-linked Fv, or dsFv (the variable, antigen-binding determinative region of a single light and heavy chain of an antibody linked together by a disulfide bond); a camelized VH (the variable, antigen-binding determinative region of a single heavy chain of an antibody in which some amino acids at the VH interface are those found in the heavy chain of naturally occurring camel antibodies); a bispecific sFv (a sFv or a dsFv molecule having two antigen-binding domains, each of which can be directed to a different epitope); a diabody (a dimerized sFv formed when the VH domain of a first sFv assembles with the VL domain of a second sFv and the VL domain of the first sFv assembles with the VH domain of the second sFv; the two antigen-binding regions of the diabody can be directed towards the same or different epitopes); and a triabody (a trimerized sFv, formed in a manner similar to a diabody, but in which three antigen-binding domains are created in a single complex; the three antigen binding domains can be directed towards the same or different epitopes). Antibodies provided herein can also include one or more CDR sequences of an antibody. The CDR sequences can be linked together on a scaffold when two or more CDR sequences are present. In certain embodiments, an antibody comprises a single-chain Fv ("scFv"). scFvs are antibody fragments comprising the VH and VL domains of an antibody, wherein these domains are present in a single polypeptide chain. Generally, the scFv polypeptide further comprises a polypeptide linker between the VH and VL domains which enables the scFv to form the desired structure for antigen binding. For a review of scFvs, see Pluckthun in *The Pharmacology of Monoclonal Antibodies*, vol. 113, Rosenburg and Moore eds. Springer-Verlag, New York, pp. 269-315 (1994). Without being bound by any particular theories, Fv molecules can be able to penetrate tissues because of their small size. A whole antibody can be enzymatically cleaved by pepsin to produce a $F(ab')_2$ fragment, or can be enzymatically cleaved by papain to produce two Fab fragments.

In certain embodiments, anti-KIT antibodies for use in the methods described herein are human, composite human, or humanized monoclonal antibodies. In a particular embodiment, an antibody for use in the methods described herein is an engineered antibody, for example, antibody produced by recombinant methods. In a specific embodiment, an antibody described herein is a humanized antibody comprising one or more non-human (e.g., rodent or murine) CDRs and one or more human framework regions (FR), and optionally human heavy chain constant region and/or light chain constant region. In a specific embodiment, an antibody described herein comprises one or more primate (or non-human primate) framework regions. In a specific embodiment, an antibody described herein does not comprise non-human primate framework regions.

Antibodies for use in the methods provided herein can include antibodies comprising chemical modifications, for example, antibodies which have been chemically modified, e.g., by covalent attachment of any type of molecule to the antibody. For example, but not by way of limitation, an anti-KIT antibody can be glycosylated, acetylated, pegylated, phosphorylated, or amidated, can be derivitized via protective/blocking groups, or can further comprise a cellular ligand and or other protein or peptide, etc. For example, an antibody provided herein can be chemically modified, e.g., by glycosylation, acetylation, pegylation, phosphorylation, amidation, derivatization by known protecting/blocking groups, proteolytic cleavage, linkage to a cellular ligand or other protein, etc. Further, an anti-KIT antibody described herein can contain one or more non-classical amino acids.

In specific aspects, an anti-KIT antibody for use in the methods provided herein is a naked antibody which is not linked, fused or conjugated (e.g., artificially linked, fused or conjugated) to another molecule, peptide or polypeptide (for example, a heterologous polypeptide). In a particular embodiment, an anti-KIT antibody for use in the methods provided herein is not an antibody-drug conjugate. In a particular embodiment, an anti-KIT antibody for use in the methods provided herein is not a fusion protein. In particular embodiments, an anti-KIT antibody described herein does not comprise any non-classical amino acids.

5.2.1 Antibody Production

Antibodies (e.g., human or humanized antibodies) described herein (or an antigen-binding fragment thereof) that immunospecifically bind to a KIT antigen can be produced by any method known in the art for the synthesis of antibodies, for example, by chemical synthesis or by recombinant expression techniques. The methods described herein employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described in the references cited herein and are fully explained in the literature. See, e.g., Maniatis et al. (1982) *Molecular Cloning: A Laboratory Manual*, Cold Spring Harbor Laboratory Press; Sambrook et al. (1989), *Molecular Cloning: A Laboratory Manual*, Second Edition, Cold Spring Harbor Laboratory Press; Sambrook et al. (2001) *Molecular Cloning: A Laboratory Manual*, Cold Spring Harbor Laboratory Press, Cold Spring Harbor, N.Y.; Ausubel et al., *Current Protocols in Molecular Biology*, John Wiley & Sons (1987 and annual updates); *Current Protocols in Immunology*, John Wiley & Sons (1987 and annual updates) Gait (ed.) (1984) *Oligonucleotide Synthesis: A Practical Approach*, IRL Press; Eckstein (ed.) (1991) *Oligonucleotides and Analogues: A Practical Approach*, IRL Press; Birren et al. (eds.) (1999) *Genome Analysis: A Laboratory Manual*, Cold Spring Harbor Laboratory Press.

For example, humanized antibodies can be produced using a variety of techniques known in the art, including but not limited to, CDR-grafting (European Patent No. EP 239,400; International publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973), chain shuffling (U.S. Pat. No. 5,565,332), and techniques disclosed in, e.g., U.S. Pat. Nos. 6,407,213, 5,766,886, WO 9317105, Tan et al., J. Immunol. 169:1119 25 (2002), Caldas et al., Protein Eng. 13(5):353-60 (2000), Morea et al., Methods 20(3):267 79 (2000), Baca et al., J. Biol. Chem. 272(16):10678-84 (1997), Roguska et al., Protein Eng. 9(10):895 904 (1996), Couto et al., Cancer Res. 55 (23 Supp):5973s-5977s (1995), Couto et al., Cancer Res. 55(8): 1717-22 (1995), Sandhu J S, Gene 150(2):409-10 (1994), and Pedersen et al., J. Mol. Biol. 235(3):959-73 (1994). See also U.S. Patent Pub. No. US 2005/0042664 A1 (Feb. 24, 2005), which is incorporated herein by reference.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563 681 (Elsevier, N.Y., 1981). The term "monoclonal antibody" as used herein is not limited to antibodies produced through hybridoma technology. For example, monoclonal antibodies can be produced by recombinant technology, e.g., recombinant monoclonal antibodies expressed by a host cell, such as a mammalian host cell.

Methods for producing and screening for specific antibodies using hybridoma technology are routine and well known in the art. For example, in the hybridoma method, a mouse or other appropriate host animal, such as a sheep, goat, rabbit, rat, hamster or macaque monkey, is immunized to elicit lymphocytes that produce or are capable of producing antibodies that will specifically bind to the protein (e.g., extracellular domain of human KIT) used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)). Additionally, a RIMMS (repetitive immunization multiple sites) technique can be used to immunize an animal (Kilptrack et al., 1997 Hybridoma 16:381-9, which is incorporated herein by reference).

Non-limiting examples of myeloma cell lines include murine myeloma lines, such as those derived from MOPC-21 and MPC-11 mouse tumors available from the Salk Institute Cell Distribution Center, San Diego, Calif., USA, and SP-2 or X63-Ag8.653 cells available from the American Type Culture Collection, Rockville, Md., USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Antibodies described herein include antibody fragments which recognize specific KIT antigens and can be generated by any technique known to those of skill in the art. For example, Fab and F(ab')$_2$ fragments described herein can be produced by proteolytic cleavage of immunoglobulin molecules, using enzymes such as papain (to produce Fab fragments) or pepsin (to produce F(ab')$_2$ fragments). A Fab fragment corresponds to one of the two identical arms of an antibody molecule and contains the complete light chain paired with the VH and CH1 domains of the heavy chain. A F(ab')$_2$ fragment contains the two antigen-binding arms of an antibody molecule linked by disulfide bonds in the hinge region.

In one aspect, to generate whole antibodies, PCR primers including VH or VL nucleotide sequences, a restriction site, and a flanking sequence to protect the restriction site can be used to amplify the VH or VL sequences from a template, e.g., scFv clones. Utilizing cloning techniques known to those of skill in the art, the PCR amplified VH domains can be cloned into vectors expressing a VH constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

Single domain antibodies, for example, antibodies lacking the light chains, can be produced by methods well-known in the art. See Riechmann et al., 1999, J. Immunol. 231:25-38; Nuttall et al., 2000, Curr. Pharm. Biotechnol. 1(3):253-263; Muylderman, 2001, J. Biotechnol. 74(4):277302; U.S. Pat. No. 6,005,079; and International Publication Nos. WO 94/04678, WO 94/25591, and WO 01/44301.

5.3 Compositions

Provided herein are compositions, such as pharmaceutical compositions, comprising one or more anti-KIT antibodies (e.g., humanized antibodies) for use in the methods described herein, or antigen-binding fragments thereof. In particular aspects, compositions described herein can be for in vitro, in vivo, or ex vivo uses. In specific embodiments, provided herein is a pharmaceutical composition comprising an anti-KIT antibody (e.g., a humanized antibody) for use in the methods described herein (or an antigen-binding fragment thereof) and a pharmaceutically acceptable carrier or excipient.

As used herein, the term "pharmaceutically acceptable" means being approved by a regulatory agency of the Federal or a state government, or listed in the U.S. Pharmacopeia, European Pharmacopeia or other generally recognized Pharmacopeia for use in animals, and more particularly in humans.

Therapeutic formulations containing one or more antibodies (e.g., humanized antibodies) provided herein can be prepared for storage by mixing the antibody having the desired degree of purity with optional physiologically acceptable carriers, excipients or stabilizers (*Remington's Pharmaceutical Sciences* (1990) Mack Publishing Co., Easton, Pa.; *Remington: The Science and Practice of Pharmacy*, 21st ed. (2006) Lippincott Williams & Wilkins, Baltimore, Md.), in the form of lyophilized formulations or aqueous solutions. Acceptable carriers, excipients, or stabilizers are nontoxic to recipients at the dosages and concentrations employed, and include buffers such as phosphate, citrate, and other organic acids; and/or non-ionic surfactants such as TWEEN™, PLURONICS™ or polyethylene glycol (PEG).

Formulations, such as those described herein, can also contain more than one active compounds (for example, molecules, e.g., antibody or antibodies described herein) as necessary for the particular indication being treated. In certain embodiments, formulations comprise an antibody provided herein and one or more active compounds with complementary activities that do not adversely affect each other. Such molecules are suitably present in combination in amounts that are effective for the purpose intended.

The formulations to be used for in vivo administration can be sterile. This is readily accomplished by filtration through, e.g., sterile filtration membranes.

In specific aspects, the pharmaceutical compositions provided herein contain therapeutically effective amounts of one or more of the anti-KIT antibodies (e.g., humanized antibodies) provided herein, and optionally one or more additional prophylactic of therapeutic agents, in a pharmaceutically acceptable carrier. Such pharmaceutical compositions are useful in the prevention, treatment, management or amelioration of an eosinophil or mast cell related disorder, such as NMO, NMOSD, MS, NF (e.g. NF1 or NF2), or one or more of the symptoms thereof.

Pharmaceutical carriers suitable for administration of the antibodies provided herein include any such carriers known to those skilled in the art to be suitable for the particular mode of administration.

In addition, the antibodies described herein can be formulated as the sole pharmaceutically active ingredient in the composition or can be combined with other active ingredients (such as one or more other prophylactic or therapeutic agents).

Compositions can contain one or more anti-KIT antibodies provided herein. In one embodiment, the antibodies are formulated into suitable pharmaceutical preparations, such as solutions, suspensions, powders, or elixirs, in sterile solutions or suspensions for parenteral administration. In one embodiment, the antibodies are formulated into suitable pharmaceutical preparations, such as solutions, suspensions, tablets, dispersible tablets, pills, capsules, powders, sustained release formulations or elixirs, for oral administration, as well as transdermal patch preparation and dry powder inhalers.

In such compositions, one or more antibodies provided herein (or conjugates thereof) is (are) mixed with a suitable pharmaceutical carrier. Concentrations of an antibody or antibodies in the compositions can, for example, be effective for delivery of an amount, upon administration, that treats, prevents, protects against or manages an eosinophil or mast cell related disorder, such as NMO, NMOSD, MS, NF (e.g. NF1 or NF2), or one or more symptoms thereof.

In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

In certain aspects, an antibody (e.g., a humanized antibody) provided herein (or an antibody-drug conjugate thereof) is included in the pharmaceutically acceptable carrier in an effective amount sufficient to exert a therapeutically useful effect in the absence of, or with minimal or negligible, undesirable side effects on the patient treated. A therapeutically effective concentration can be determined empirically by testing the compounds in in vitro and in vivo systems using routine methods and then extrapolated therefrom for dosages for humans.

The concentration of antibody in the pharmaceutical composition will depend on, e.g., the physicochemical characteristics of the antibody, the dosage schedule, and amount administered as well as other factors known to those of skill in the art. In certain aspects, the concentration of antibody-drug conjugate in the pharmaceutical composition will depend on, e.g., the physicochemical characteristics of the antibody and/or the drug, the dosage schedule, and amount administered as well as other factors known to those of skill in the art.

In one embodiment, a therapeutically effective dosage produces a serum concentration of antibody of from about 0.1 ng/ml to about 50-100 µg/ml. The pharmaceutical compositions, in another embodiment, provide a dosage of from about 0.001 mg to about 2000 mg of antibody per kilogram of body weight for administration over a period of time, e.g., every day, every week, every 2 weeks, or every 3 weeks. Pharmaceutical dosage unit forms can be prepared to provide from about 0.01 mg to about 2000 mg, and in one embodiment from about 10 mg to about 500 mg of the antibody and/or a combination of other optional essential ingredients per dosage unit form.

In a particular embodiment, an antibody-drug conjugate described herein is administered at an effective dosage of about 1 to 100 mg of antibody-drug conjugate per kilogram of body weight for administration over a period of time, e.g., every day, every week, every 2 weeks, or every 3 weeks.

An anti-KIT antibody described herein can be administered at once, or can be divided into a number of smaller doses to be administered at intervals of time. It is understood that the precise dosage and duration of treatment is a function of the disease being treated and can be determined empirically using known testing protocols or by extrapolation from in vivo or in vitro test data. It is to be noted that concentrations and dosage values can also vary with the severity of the condition to be alleviated. It is to be further understood that for any particular subject, specific dosage regimens can be adjusted over time according to the individual need and the professional judgment of the person administering or supervising the administration of the compositions, and that the concentration ranges set forth herein are exemplary only and are not intended to limit the scope or practice of the claimed compositions.

Upon mixing or addition of an antibody, the resulting mixture can be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and can be empirically determined.

Pharmaceutical compositions described herein are provided for administration to humans and animals, such as mammals (e.g., cat or dog), in unit dosage forms, such as sterile parenteral (e.g., intravenous) solutions or suspensions containing suitable quantities of the compounds or pharmaceutically acceptable derivatives thereof. Pharmaceutical compositions are also provided for administration to humans and animals, such as mammals (e.g., cat or dog), in unit dosage form, such as tablets, capsules, pills, powders, granules, and oral solutions or suspensions, and oil-water emulsions containing suitable quantities of the compounds or pharmaceutically acceptable derivatives thereof. The antibody is, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the antibody sufficient to produce the desired therapeutic effect, in association with the required pharmaceutical carrier, vehicle or diluent. Examples of unit-dose forms include ampoules and syringes and individually packaged tablets or capsules. Unit-dose forms can be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

In certain embodiments, one or more anti-KIT antibodies described herein are in a liquid pharmaceutical formulation. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered can also contain minor amounts of nontoxic auxiliary substances such as wetting agents, emulsifying agents, solubilizing agents, and pH buffering agents and the like.

Actual methods of preparing such dosage forms are known, or will be apparent, to those skilled in this art; for example, see, e.g., *Remington's Pharmaceutical Sciences* (1990) Mack Publishing Co., Easton, Pa.; *Remington: The Science and Practice of Pharmacy,* 21st ed. (2006) Lippincott Williams & Wilkins, Baltimore, Md.

Dosage forms or compositions containing antibody in the range of 0.005% to 100% with the balance made up from non-toxic carrier can be prepared. Methods for preparation of these compositions are known to those skilled in the art.

Parenteral administration, in one embodiment, is characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents. Other routes of administration may include, epidural administration, enteric administration, intracerebral administration, nasal administration, intraarterial administration, intracardiac administration, intraosseous infusion, intrathecal administration, and intraperitoneal administration.

Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions can be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Pharmaceutical carriers also include ethyl alcohol, polyethylene glycol and propylene glycol for water miscible vehicles; and sodium hydroxide, hydrochloric acid, citric acid or lactic acid for pH adjustment.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

An anti-KIT antibody described herein can be suspended in micronized or other suitable form. The form of the resulting mixture depends upon a number of factors, including the intended mode of administration and the solubility of the compound in the selected carrier or vehicle. The effective concentration is sufficient for ameliorating the symptoms of the condition and can be empirically determined.

In other embodiments, the pharmaceutical formulations are lyophilized powders, which can be reconstituted for administration as solutions, emulsions and other mixtures. They can also be reconstituted and formulated as solids or gels.

The lyophilized powder is prepared by dissolving an antibody provided herein, in a suitable solvent. In some embodiments, the lyophilized powder is sterile. The solvent can contain an excipient which improves the stability or other pharmacological component of the powder or reconstituted solution, prepared from the powder. Excipients that can be used include, but are not limited to, dextrose, sorbital, fructose, corn syrup, xylitol, glycerin, glucose, sucrose or other suitable agent. The solvent can also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Antibodies described herein can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

The antibodies and other compositions provided herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874. In some embodiments, the anti-KIT antibodies described herein are targeted (or otherwise administered) to the bone marrow. In some embodiments, anti-KIT antibodies described herein are targeted (or otherwise administered) to the gastrointestinal tract. In some embodiments, anti-KIT antibodies described herein are targeted (or otherwise administered) to the brain. In specific embodiments, an anti-KIT antibody described herein is capable of crossing the blood-brain barrier.

In specific embodiments, anti-KIT antibodies described herein are targeted (or otherwise administered) to an ocular tissue or organ. In particular aspects, a composition comprising anti-KIT antibodies described herein can be targeted to an ocular tissue or organ as eye drops or gels. In particular aspects, a composition comprising anti-KIT antibodies described herein can be targeted to the ear.

Provided herein is a pharmaceutical pack or kit comprising one or more containers filled with one or more of the ingredients of the pharmaceutical compositions described herein, such as one or more antibodies provided herein. Optionally associated with such container(s) can be a notice in the form prescribed by a governmental agency regulating the manufacture, use or sale of pharmaceuticals or biological products, which notice reflects approval by the agency of manufacture, use or sale for human administration.

5.4 Dosages and Administration

The dosage and frequency of administration of an anti-KIT antibody described herein or a pharmaceutical composition thereof is administered to a subject in need thereof (e.g., mammal, such as human, dog or cat) in accordance with the methods for treating an eosinophil or mast cell related disorder, such as NMO, NMOSD, MS, or NF (e.g., NF1 or NF2), provided herein will be efficacious while minimizing side effects. The exact dosage of an anti-KIT antibody described herein to be administered to a particular subject or a pharmaceutical composition thereof can be determined in light of factors related to the subject that requires treatment. Factors which can be taken into account include the severity of the disease state, general health of the subject, age, and weight of the subject, diet, time and frequency of administration, combination(s) with other therapeutic agents or drugs, reaction sensitivities, and tolerance/response to therapy. The dosage and frequency of administration of an anti-KIT antibody described herein or a pharmaceutical composition thereof can be adjusted over time to provide sufficient levels of the anti-KIT antibody or to maintain the desired effect.

The precise dose to be employed in the formulation will also depend on the route of administration, and the seriousness of a KIT-associated disorder or disease (e.g., cancer, inflammatory condition, fibrosis), and should be decided according to the judgment of the practitioner and each patient's circumstances.

In certain aspects, for the anti-KIT antibodies described herein, the dosage administered to a patient, to prevent, protect against, manage, or treat an eosinophil or mast cell related disorder, such as NMO, NMOSD, MS, or NF (e.g., NF1 or NF2), is typically 0.1 mg/kg to 100 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of the antibodies described herein can be reduced by enhancing uptake and tissue penetration of the antibodies by modifications such as, for example, lipidation.

In one embodiment, approximately 0.001 mg/kg (mg of antibody per kg weight of a subject) to approximately 500 mg/kg of an anti-KIT antibody described herein is administered to prevent, protect against, manage, or treat an eosinophil or mast cell related disorder, such as NMO, NMOSD, MS, or NF (e.g., NF1 or NF2).

In some embodiments, an effective amount of an antibody provided herein is from about 0.01 mg to about 1,000 mg. In specific embodiments, an "effective amount" or "therapeutically effective amount" of an anti-KIT antibody described herein refers to an amount of an anti-KIT antibody described herein which is sufficient to achieve at least one, two, three, four or more of the following effects: the reduction or amelioration of the severity of an eosinophil or mast cell related disorder, such as NMO, NMOSD, MS, or NF (e.g., NF1 or NF2), and/or one or more symptoms associated therewith; the reduction in the duration of one or more symptoms associated with an eosinophil or mast cell related disorder, such as NMO, NMOSD, MS, or NF (e.g., NF1 or NF2); the prevention in the recurrence of one or more symptoms of an eosinophil or mast cell related disorder, such as NMO, NMOSD, MS, or NF (e.g., NF1 or NF2); the regression of an eosinophil or mast cell related disorder, such as NMO, NMOSD, MS, or NF (e.g., NF1 or NF2), and/or one or more symptoms associated therewith; the reduction in hospitalization of a subject; the reduction in hospitalization length; the increase in the survival of a subject with an eosinophil or mast cell related disorder, such as NMO, NMOSD, MS, or NF (e.g., NF1 or NF2); the inhibition (e.g., partial inhibition) of the progression of an eosinophil or mast cell related disorder, such as NMO, NMOSD, MS, or NF (e.g., NF1 or NF2), and/or one or more symptoms associated therewith; the prevention of the development or onset of one or more symptoms associated an eosinophil or mast cell related disorder, such as NMO, NMOSD, MS, or NF (e.g., NF1 or NF2); a decrease in the concentration of one or more inflammatory mediators (e.g., cytokines or interleukins) in biological specimens (e.g., plasma, serum, cerebral spinal fluid, urine, or any other biofluids) of a subject with an eosinophil or mast cell related disorder, such as NMO, NMOSD, MS, or NF (e.g., NF1 or NF2); and improvement in the quality of life as assessed by methods well known in the art, e.g., questionnaires. In some embodiments, "effective amount" as used herein also refers to the amount of an antibody described herein to achieve a specified result (e.g., inhibition of one or more KIT biological activities of a cell, such as inhibition of cell proliferation).

In some embodiments, an anti-KIT antibody described herein is administered as necessary, e.g., weekly, biweekly (i.e., once every two weeks), monthly, bimonthly, trimonthly, etc.

In some embodiments, a single dose of an anti-KIT antibody described herein is administered one or more times to a patient to impede, prevent, manage, treat and/or ameliorate an eosinophil or mast cell related disorder, such as NMO, NMOSD, MS, or NF (e.g., NF1 or NF2).

In particular embodiments, an anti-KIT antibody or pharmaceutical composition thereof is administered to a subject in accordance with the methods for treating an eosinophil or mast cell related disorder, such as NMO, NMOSD, MS, or NF (e.g., NF1 or NF2), provided herein in cycles, wherein the anti-KIT antibody or pharmaceutical composition is administered for a period of time, followed by a period of rest (i.e., the anti-KIT antibody or pharmaceutical composition is not administered for a period of time).

The methods provided herein involve administering an anti-KIT antibody by any suitable routes. Non-limiting examples of routes of administration include, parenteral administration for example subcutaneous, intramuscular or intravenous administration, epidural administration, enteric administration, intracerebral administration, nasal administration, intraarterial administration, intracardiac administration, intraosseous infusion, intrathecal administration, and intraperitoneal administration. Methods provided herein include routes of administration targeting the brain, an ocular tissue or organ, spinal cord, or ear or auricular tissue. In a particular aspect, methods provided herein include routes of administration targeting the nervous system, e.g., central nervous system.

In specific embodiments, methods provided herein involve administering an anti-KIT antibody via a route suitable for crossing the blood-brain barrier.

6. EXAMPLES

The examples in this section (i.e., section 6) are offered by way of illustration, and not by way of limitation.

6.1 Example 1: Xenograft Animal Model of NF

Confirmation that NF1 tumor growth can be inhibited by an anti-KIT antibody or antigen binding fragment thereof may be determined using a sciatic nerve xenograft model. In a specific embodiment, the anti-KIT antibody is an antibody comprising the VH and VL CDRs as set forth in Table 1.

A sciatic nerve xenograft model, which shows robust growth of a human NF1 malignant peripheral nerve sheath tumor ("MPNST") cell line within the nerve compartment, can result in visibly-enlarged nerves within 8 weeks (FIG. 3, from Perrin et al., Laboratory Investigation 87:1092-1102 (2007)). This provides a model similar to a rapidly-growing plexiform neurofibroma, with histology better resembling an MPNST.

Scid (immunocompromised) female mice (8-12 weeks old) have human NF1 tumor-derived sNF96.2 cells xenografted into sciatic nerves. After several weeks (e.g., two weeks), the mice are treated with an anti-KIT antibody. Control mice also are given unilateral xenografts but do not receive treatment with an anti-KIT antibody. A period of time (e.g., 12 weeks) after xenografting, the mice are humanely euthanized and their sciatic nerves dissected out. Equal lengths of nerve are weighed, measured, and photographed for all nerves (control xenografts, normal nerves of treated mice, xenografts of treated mice). In addition, the nerves are fixed and longitudinally embedded in paraffin, then cut into 7-micron sections. Immunohistochemical staining is done for Ki67 (proliferation index) and von Willebrand factor (to analyze vascularity, number of blood vessels per microscopic field), to compare the treated with untreated xenografts (e.g., 2-tailed t test for comparing immunostain outcomes). Detection of a clear reduction in xenograft size in the treated mice, compared to untreated, and of a decreased proliferation index and/or decreased vascularity is an indication of anti-tumor efficacy of an anti-KIT antibody.

Additional NF1 or NF2 cell lines may be tested in similar xenograft mouse models with appropriate adaptations made by those skilled in the art. Schwannomatosis cell lines may be tested in similar xenograft mouse models with appropriate adaptations made by those skilled in the art.

Neurofibroma Schwann cells immortalized into cell line cultures and then implanted into mice may provide longer-term xenograft models to confirm if more slowly-growing NF1 tumors respond to an anti-KIT antibody. Alternatively, genetically engineered mice that form neurofibromas (e.g., the Dhh-Cre Nf1 knockout mice) can be treated with an anti-KIT antibody to assess the efficacy of long-term anti-KIT antibody therapy in prevention of tumor formation in a mouse model. Efficacy of an anti-KIT antibody for treating NF can be assessed/confirmed in some of the same xenografts (e.g., mice implanted with sNF96.2 cells), but using scid mice having an NF1 heterozygous background.

6.2 Example 2: Treatment of Mast Cells with Anti-KIT Antibody Inhibits Mast Cell Activity

6.2.1 Introduction

This example demonstrates that treatment of mast cells with anti-KIT antibody inhibits ligand-induced phosphorylation of KIT, degranulation, and cytokine release.

6.2.2 Materials and Methods

Cells and Flow Cytometry

LAD2 cells, an SCF-dependent human mast cell line that express KIT and FcεR1 (FIG. 2A and FIG. 2B; see also, Kirshenbaum et al., 2003, Leuk. Res. 27: 677-682) were utilized. LAD2 cells (100,000 LAD2 cells per sample) were resuspended in 10 mL of phosphate buffered saline ("PBS") and centrifuged at 1200 rpm for 3 minutes, washed in FACS buffer (PBS containing 1% newborn fetal calf serum and 0.01% sodium azide), and spun again at 1200 rpm for 3 minutes. The cell pellet was resuspended in 200 µL of FACS buffer and incubated on ice for one hour. The cells were either unstained, or incubated in anti-human Fc epsilon receptor 1 alpha-APC (eBioscience, 17-5899), or anti-human CD117-PE (anti-KIT, BD Pharmingen, 555714), or the isotype controls, mouse IgG2b APC (eBioscience, 8017-4732) and mouse IgG1, kappa PE (R&D Systems), respectively. After a one hour incubation on ice, the cells were washed three times with FACS buffer as above and resuspended in 500 µL of FACS buffer. Samples were analyzed on the Accuri C6 instrument using the FL2 channel for PE labeled samples and the FL4 channel for APC labeled samples.

ELISA Assay for Ligand-Induced Phosphorylation Analysis of KIT

LAD2 cells (500,000 LAD2 cells per condition) were incubated overnight under standard conditions (37° C. with 5% $CO_2$) in StemPro-34 serum free media with StemPro Nutrient Supplement, 1× penicillin, 1× streptomycin, and 1× L-glutamine in the absence of SCF. To prepare the ELISA plates, 100 ng/mL of anti-KIT antibody (Neomarkers, 1 mg/mL # MS-289-PABX) in 100 µL of PBS was bound to each well of a white NUNC maxisorb plate overnight at 4° C. After overnight incubation, the cells were incubated with or without serial dilutions of an IgG1 antibody (herein referred to as "anti-KIT-1") comprising the CDRs depicted in Table 1, above, that binds to the extracellular domain of canine, feline, monkey, and human KIT, but not murine KIT, for 4 hours under standard conditions. During antibody incubation, ELISA plates were blocked for 1 hour at room temperature with 100 μL of blocking buffer (3% bovine serum albumin, "BSA", in tris-buffered-saline with tween, "TBST") per well. The blocking buffer was then removed and the plates were washed one time with TBST. After washing, 50 μL of dilution buffer (1% BSA in TBST with 1 mM NaVO$_4$) was added to each well. Next, the cells were incubated with or without 12 μL of 50 μg/mL SCF for 10 minutes at 37° C. After incubation, the cells and supernatant were collected and the cells were pelleted and lysed in 200 μL of lysis buffer (25 mM Tris pH 7.4, 150 mM NaCl, 1% Triton X-100, 1 mM EDTA, 1 mM Orthovanadate and protease inhibitors). Fifty (50) μL of the lysate was aliquoted into the appropriate wells of the ELISA plate and incubated overnight at 4° C.

The ELISA plates were washed three times with TBST followed by incubation with 100 μL per well of an anti-phosphorylated-tyrosine antibody diluted 1:1000 in TBST with 1% BSA and 1 mM NaVO$_4$ for two hours at room temperature. The plates were then washed three times with TBST and 100 μL per well of ImmunoPure Streptavidin-HRP antibody (Thermo Scientific cat #21126) diluted 1:5000 in TBST with 1% BSA and 1 mM NaVO$_4$ for 1 hour. The plates were washed three times with TBST. Finally, 100 μL of 1:1 Western Pico Reagent was added to each well and the plate was read on the Lumi Glo program on a BioTek, Synergy HT plate reader.

Ligand-Induced Degranulation Analyses

LAD2 cells were incubated under standard conditions overnight with 100 ng/mL of biotinylated human myeloma IgE in StemPro-34-SFM Cytokine-Free Media containing 1× penicillin streptomycin and L-glutamine (Gibco by Life Technologies). The cells were then washed three times with 37° C. HEPES buffer, pH 7.4, counted, resuspended at 10,000 cells per 70 μL of HEPES buffer, pH 7.4, per well, and aliquoted into two 96-well places. All subsequent cell incubations were performed in the absence of CO$_2$. Twenty (20) μL and 10 μL of HEPES buffer, pH 7.4 was added to each well of column 1 and 2, respectively, and the plate was incubated at 37° C. for 10 minutes. Cells were subsequently incubated with serial dilutions of anti-KIT-1 antibody for one hour at 37° C., followed by stimulation with 10 ng/mL of SCF for 30 minutes at 37° C. Next, the cells were incubated with serial dilutions of streptavidin at 37° C. for 30 minutes. The cells were subsequently spun for 5 minutes at 450×g at 4° C. to stop the reaction and to sediment the cells. Three-hundred fifty (350) μg of p-nitrophenyl N-acetyl-β-D-glucosamide (PNAG) dissolved in citrate buffer was aliquoted into two 96 well plates at 100 μL per well. Fifty (50) μL of the cell-free supernatant was added to 96 well plates containing 100 μL (350 μg) of p-nitrophenyl N-acetyl-β-D-glucosamide dissolved in citrate buffer and incubated for 90 minutes at 37° C.

To calculate the β-hexosaminidase activity, 150 μL of 0.1% Triton X solution was added to each well of the 96 well plate containing the supernatant and cell mixture, resuspended, and added to the remaining plate of PNAG. 150 μL of 0.1% Triton X solution was also added to each well of the 96 well plate containing the supernatant/PNAG mixture. The plates were incubated for 90 minutes at 37° C., followed by the addition of 50 μL of 400 mM glycine to each well. The plate absorbance was read at 405 nm to calculate the total amount of β-hexosaminidase (as determined by the supernatant and cell lysate plate) and the amount of secreted β-hexosaminidase activity (as determined by the supernatant plate). The percentage of β-hexosaminidase activity present in the supernatant was calculated as one hundred times the supernatant content divided by the supernatant and lysate content. Cells treated with streptavidin alone (i.e. no antibody, no SCF) represent the baseline of β-hexosaminidase in unstimulated cells. Cells treated with streptavidin and SCF, in the absence of antibody, represent unperturbed degranulation.

Cytokine Release $2.3 \times 10^6$ LAD2 cells were incubated with 100 ng/mL of biotin IgE in SCF-free media overnight under standard conditions. Following sensitization with IgE, the cells were washed three times in SCF-free media and resuspended in 12 mLs of SCF-free media. 500 μL of cells was aliquoted into each well of a 24 well plate. The cells were then incubated with a negative control antibody that recognizes KLH or with serial dilutions of anti-KIT-1 antibody, under standard conditions for 4 hours. Next, the cells were incubated with or without 100 ng/mL of SCF (in a volume of 10 μL) and/or 100 ng/mL of streptavidin for 16 hours under standard conditions. After incubation, the lysate was centrifuged at 1200 rpm for 5 minutes at room temperature. The supernatants were then run on MSD V-PLEX TNA-alpha or GM-CSF kits (MSD) according to the manufacturer's instructions to determine the degree of cytokine release.

6.2.3 Results

Treatment of Mast Cells with Anti-KIT Antibody Inhibits Ligand-Induced KIT Phosphorylation To investigate the ability of anti-KIT antibody to interfere with mast cell activity, ligand-induced KIT phosphorylation was assessed in the presence and absence of anti-KIT antibody in LAD2 cells. In particular, LAD2 cells were incubated with anti-KIT-1 antibody prior to exposure to the KIT ligand SCF. An ELISA assay specific for phosphorylated tyrosine was performed to determine the level of SCF-induced phosphorylated KIT in the presence and absence of the anti-KIT-1 antibody. Preincubation with anti-KIT-1 antibody resulted in diminished ligand-dependent autophosphorylation of KIT in a dose-dependent manner (FIG. 2C). These data demonstrate anti-KIT antibody treatment can block ligand-induced autophosphorylation of KIT expressed on mast cells, a precursor event to the activation of mast cells via KIT signaling.

Treatment of Mast Cells with anti-KIT Antibody Inhibits Ligand-Dependent Mast Cell Degranulation and Cytokine Release KIT signaling in mast cells leads to degranulation and a triggering of the inflammatory response. To investigate the effect of anti-KIT antibody on ligand-induced mast cell degranulation, LAD2 cells were incubated with either anti-KIT-1 antibody prior to ligand exposure. Incubation with anti-KIT-1 antibody resulted in a dose-dependent decrease in B-hex release, a readout for degranulation, after exposure to SCF (FIG. 3A). Further, the antibody also inhibited the release of the cytokines TNFα and GM-CSF after stimulation with the KIT ligand (FIG. 3B and FIG. 3C). These data demonstrate that treatment with anti-KIT antibody inhibits ligand-induced degranulation and cytokine release in mast cells. Moreover, these data demonstrate that anti-KIT-1 antibody, that is, an antibody comprising the CDRs as depicted in Table 1, above, exhibits particularly effective inhibition of such ligand-induced activity in mast cells.

6.3 Example 3: Anti-KIT Antibody Treatment Reduces Mast Cell Numbers

6.3.1 Introduction

This example demonstrates that administration of anti-KIT-1 antibody to healthy dogs significantly reduces the population of mast cells.

6.3.2 Materials and Methods

Animals

Four healthy, 1 year old, unrelated hound dogs, weighing between 20-25 kgs each, were utilized. The dogs were allowed acclimation to the environment for two weeks. Dogs were divided into two groups (one female, one male) for administration of a low dose (10 mg/kg; dogs 1 and 2) or high dose (30 mg/kg; dogs 3 and 4) of anti-KIT-1 antibody.

Anti-KIT-1 Antibody Administration 10 mg/kg (dogs 1 and 2) or 30 mg/kg (dogs 3 and 4) of anti-KIT-1 antibody was administered once via a 20-gauge intravenous catheter in the cephalic vein, in the absence of premedications (sedative, anti-emetics). The day of antibody administration was considered day 0. The anti-KIT-1 antibody was diluted into a total volume of 200 ml 0.9% NaCl. Temperature, heart rate, and respiratory rate were monitored at specific intervals over the 6 hour antibody infusion period. The intravenous catheters were removed following completion of the infusion. Preliminary evaluations of tolerability indicated that anti-KIT-1 antibody was tolerated with mild clinical toxicities.

Skin Biopsy and Evaluation for Mast Cell Numbers

Skin biopsies were performed on Days −7, −3, 7, and 28. While the dogs were under general anesthesia, a 5 cm by 5 cm area of skin on the dorsum was clipped and prepped in a sterile manner. Four separate skin punch 8 mm biopsies were obtained from the clipped area, placed in formalin and the skin was then closed with simple interrupted sutures using 3-0 nylon. The four formalin fixed skin biopsies from each time point were placed into a single cassette and embedded in paraffin. Slides were made from each time cassette and were stained with hematoxylin and eosin for standard histopathological evaluation and Toluidine blue to facilitate identification of mast cells.

Mast cells with metachromatic granules were counted in three random 400× fields in each biopsy sample (n=4 per cassette) at each time point for each dog, including superficial dermal, periadnexal, and deep dermal areas of each Toluidine blue stained slide. The mean number of mast cells was then provided for each time point for each dog's set of skin biopsies.

6.3.3 Results

Anti-KIT-1 antibody was administered to healthy dogs as described above. Preliminary evaluations indicated that anti-KIT-1 antibody in dogs is well-tolerated with minimal clinical toxicity.

To investigate the ability of anti-KIT antibody to diminish mast cell populations, skin biopsies were performed throughout the study. Mast cell numbers in the skin are viewed as a surrogate to monitor the effects of KIT signaling modulators in peripheral tissues. Skin biopsies did not reveal any overt histopathologic lesions. Mast cell numbers were markedly decreased in a dose-dependent fashion at both day 7 and day 28 when compared to baseline evaluation (FIG. 4). Mast cells from the dogs treated with the high dose of anti-KIT-1 exhibited features of apoptosis/necrosis at day 7. The dogs treated with the low dose of anti-KIT-1 exhibited evidence of mast cell recovery in the skin samples by day 28, however, the mast cell numbers remained lower than those present at baseline (FIG. 4). Finally, the mast cells exhibited decreased granularity in all dogs at day 28 when compared to baseline.

In all dogs, mast cell numbers in the skin were markedly decreased at 7 days after dosing. In the dogs receiving 30 mg/kg of anti-KIT-1 antibody, skin mast cell counts on Day 28 were similar to those observed on Day 7 whereas counts in the 10 mg/kg cohort showed evidence of recovery, suggesting a dose-related effect.

These data demonstrate that treatment with anti-KIT-1 antibody markedly decreases the mast cell population in the skin and that sufficient concentrations of anti-KIT-1 antibody were achieved in the skin to inhibit KIT signaling and mast cell survival.

6.4 Example 4: Treatment of a Feline Asthma Model with Anti-KIT Antibody Reduces Eosinophil Cell Populations

6.4.1 Introduction

The example presented herein demonstrates successful use of anti-KIT antibody (anti-KIT-1) to significantly reduce airway eosinophilia, one of the key features of asthma and a critical target of any effective therapy, in a feline model of asthma.

6.4.2 Materials and Methods

Anti-KIT-1 Antibody Administration

Cats were administered 20 mg/kg of anti-KIT-1 antibody via slow intravenous infusion. Infusions began at 10 mL/hour for at least 30 minutes. If side effects were absent, infusions were optionally increased to 20 mL/hour for the remainder of the infusion. Administration of anti-KIT-1 antibody was not associated with induction of any clinically important abnormalities in CBC, serum biochemical profile, or urine concentrating ability over a 28 day period.

Phase I: For Evaluation of Acute Effects of Anti-KIT-1 Administration in a Feline Model of Asthma Cats were challenged with bermuda grass allergen ("BGA") for 30 seconds on day −7. All challenges with BGA were performed with 1.25-40 µg/mL of nebulized bermuda glass allergen ("BGA") for 30 seconds. On day −1, cats were administered anti-KIT-1 antibody or placebo, followed by an additional BGA challenge. The following day, day 0, cats were again challenged with BGA. After BGA challenge on day 0, ventilator acquired pulmonary mechanics were analyzed and blood and bronchoalveolar lavage fluid ("BALF") were collected. Cats were additionally challenged with BGA on day 7. On day 14, cats were administered a second dose of anti-KIT-1 antibody or placebo and subsequently challenged with BGA. On day 27, cats were additionally challenged with BGA. Finally, on day 28, cats were challenged with 0.0625-32 mg/mL of nebulized methacholine for 30 seconds to assess ventilator acquired pulmonary mechanics, followed by BALF and blood collection.

Phase II: For Evaluation of Chronic Effects of Anti-KIT-1 Administration in a Feline Model of Asthma In order to assess the chronic asthma feline model, Phase II studies were initiated, wherein, during days 28 to day 90 after Phase I, above, cats were challenged weekly with BGA. On day 90, the events of Phase I were repeated.

Evaluation of Airway Eosinophilia

BALF was collected and a cytospin was prepared using standard techniques. The concentrated cells were subsequently stained for differential cell counts. The percent of eosinophil cells in the population was determined by counting 200 total nucleated cells.

Airway Response to Bronchoprovocation

The airway response to bronchoprovocation was measured using ventilator-acquired pulmonary mechanics. Bronchoprovocation was performed with bermuda grass allergen (BGA) on day 0 and with methacholine on day 28. To assess airway reactivity, ventilator-calculated airway resistance measurements were collected in response to bronchoprovocation with BGA or with methacholine. Measurements were collected until the airway reactivity reached 150% or 200% above the baseline for BGA and methacholine, respectively. The data was calculated as the effective concentration of BGA or mathacholine required to increase the baseline airway response by 150% or by 200%, respectively. No significant reduction in airway reactivity was observed during the acute or chronic phases for anti-KIT-1 antibody-treated cats, as compared to placebo-treated cats.

Statistical Analyses

Data were assessed for normality using a Shapiro-Wilk test. Normally distributed data were analyzed using a One-Way Repeated Measures Analysis of Variance (ANOVA). Post-hoc analysis was performed using the Holm-Sidak method. Non-normally distributed data were analyzed using the Friedman Repeated Measures Analysis of Variance on Ranks $P<0.05$ was considered significant.

6.4.3 Results

Treatment of Asthmatic Cats with Anti-Kit Antibody Decreases Airway Eosinophil Cell Numbers Anti-KIT-1 antibody was evaluated in an established feline model of BGA-induced asthma, with each cat acting as its own control after a wash-out period. Ten cats were dosed at 20 mg/kg anti-KIT-1 antibody on days −1 and 14 of each 28-day treatment phase. For analysis of the acute phase of asthma, airway eosinophilia were assessed one day after the first 20 mg/kg infusion of anti-KIT-1. Airway eosinophilia were significantly reduced in the acute model (FIG. 5A, p=0.009). To analyze the chronic phase of asthma, airway eosinophilia were assessed one week after the second anti-KIT-1 antibody administration during phase II. Sustained reductions in the airway eosinophilia were observed in the chronic phase as compared to placebo-treated cats (FIG. 5B, p=0.032). Effects of airway reactivity were not observed in either the acute or chronic phase.

These data indicate that administration of anti-KIT-1 antibody significantly reduces eosinophil accumulation during an allergic asthma response.

6.5 Example 5: Treatment of Mast Cells with Anti-KIT-1 Antibody Does Not Induce Degranulation in Primary Human Mast Cells In Vitro 6.5.1 Introduction This Example demonstrates the effect of anti-KIT-1 antibody alone on degranulation of human mast cells. In particular, this Example demonstrates that the anti-KIT-1 antibody alone does not induce degranulation of mast cells.

6.5.2 Materials and Methods

Cell Culture

Primary human mast cells were obtained by isolating $CD34^+$ progenitor cells from human peripheral blood and differentiating the progenitors into mature mast cells by standard methods (Saito et al., Nature Protocols. 2006; 1:2178-83). Prior to analysis, the human mast cells were counted, washed twice and resuspended at a density of $5\times10^5$ cells/mL in cytokine free media (StemPro-SFM II media+1× P/S/L-Glut [no SCF]). The cells were then incubated overnight at 37° C. in a $CO_2$ incubator. For experiments assessing the ability to augment IgE-mediated degranulation, mast cells were sensitized to IgE by incubating overnight with 200 ng/mL biotinylated human myeloma IgE in cytokine-free medium.

The β-hexosaminidase release assay was performed as previously described (Kuehn et al., Current Protocols in Immunology. 2010; Chapter 7:Unit7.38). Briefly, the cells were washed three times with 10 mL HEPES buffer (10 mM HEPES, 137 mM NaCl, 2.7 mM KCl, 0.4 mM $Na_2HPO_4.7H_2O$, 5.6 mM glucose, 1.8 mM $CaCl_2.2H_2O$, 0.4% (w/v) Bovine erum Albumin), pH 7.4 at 37° C.

For experiments performed without IgE stimulation, the cells were then counted, resuspended at a final density of 10,000 cells/90 μL in HEPES buffer, pH 7.4., and 90 μL was added to each well of a 96-well plate. Cells were incubated at 37° C. for approximately 10 minutes. Serial 10-fold dilutions of anti-KIT-1 antibody, isotype control antibody and calcium ionophore A23187 were prepared to generate 10× stock solutions at concentrations ranging from 10000 to 0.1 nM. Serial 10-fold dilutions of SCF were also prepared to generate 10× stock solutions at concentrations ranging from 1000 to 0.01 ng/mL (5400-0.054 pM). Following addition of 10 μL of the 10× stock solutions to the appropriate wells, the cells were incubated in a 37° C. warm air oven (without $CO_2$) for 30 minutes. The cells were then assayed for β-hexosaminidase release.

For experiments involving IgE stimulation, IgE-sensitized mast cells were washed and resuspended to 10,000 cells/70 μL HEPES buffer, pH 7.4. The cells (70 μL/well) were plated into 96-well plate. and incubated at 37° C. for 5-10 minutes to equilibrate the cells at the activation temperature. The 10× stock solutions of anti-KIT-1 antibody, isotype control antibody, SCF and calcium ionophore A23187 were prepared as described above and 10 μL was added to the appropriate wells. The cells were then incubated at 37° C. in a warm air oven (without $CO_2$) for 30 minutes. Then, intermediate dilutions of streptavidin (SA) were prepared: 1) 10 μg/mL=2 μL stock into 198 μL buffer, and 2) 10 μL of 10 μg/mL stock into 5 mL buffer to give 20 ng/mL. 10 μL of 20 ng/mL streptavidin was then added to the appropriate wells and the cells were incubated for 30 minutes in a 37° C. warm air oven (without $CO_2$). The cells were then assayed for β-hexosaminidase release.

6.5.3 Results

Treatment of Mast Cells with Anti-KIT-1 Antibody Does Not Induce Degranulation in Primary Human Mast Cells In Vitro The β-hexosaminidase activity was measured after treatment with anti-KIT-1 antibody, isotype control antibody, SCF and calcium ionophore A23187 alone (FIG. 6A) or in combination with IgE-stimulation (FIG. 6B). These two assays tested 1) the anti-KIT-1 antibody's ability to degranulate the mast cells directly, by adding the antibody directly to the mast cells, using the calcium ionophore as a positive control (FIG. 6A), and 2) the anti-KIT-1 antibody's ability to augment IgE-mediated degranulation (FIG. 6B). The results presented in FIG. 6A show that treatment with the anti-KIT-1 antibody alone at concentrations up to 1 μM did not cause degranulation. In addition, at concentration up to 1 μM anti-KIT-1 antibody did not increase mast cell degranulation above the level observed for IgE crosslinking alone (FIG. 6B). This is in direct contrast to the results obtained using SCF, which increased IgE-mediated degranulation in a dose-dependent manner.

These experiments demonstrate that the anti-KIT-1 antibody does not have any agonistic activity on human mast cells.

6.6 Example 6: Anti-KIT-1 Antibody Shows No Agonist Activity in Cell Lines Exogenously or Endogenously Expressing KIT

6.6.1 Introduction

The purpose of this Example was to determine the ability of the anti-KIT-1 antibody to activate KIT phosphorylation in cells expressing wild-type human KIT using a cell line transfected to express human KIT or a human leukemia cell line that expresses KIT and is responsive to SCF.

6.6.2 Materials and Methods

Production of the CHO-WT KIT Cell Line

Chinese Hamster Ovary (CHO) cells were transfected by electroporation with a plasmid (pcDNA3.1) containing the full length human KIT cDNA. Stably transfected cells were selected by culturing in Ham's F-12 media containing 800 µg/mL Geneticin. Fluorescence activated cell sorting (FACS) was utilized to select the highest KIT-expressing cells (CHO-wild-type (WT) KIT cells). Sorted cells were grown out under selective pressure with Geneticin, and KIT expression was monitored by flow cytometry.

Assay Protocol: KIT Phosphorylation in CHO-WT KIT Cells

CHO-WT KIT cells were maintained in CHO complete media. The cells were passaged between one and three days prior to the assay. On the first day of the assay, cells were trypsinized and counted. Cells were then added to two 96-well culture plates in complete culture medium at a concentration of 12,500 cells/well and incubated overnight at 37° C. Two Multi-Array 96-well plates were prepared by diluting anti-KIT-1 antibody to 1 µg/ml in PBS and then adding 100 µL/well followed by incubation overnight at 2-8° C.

On assay day 2, three-fold serial dilutions of anti-KIT-1 and isotype control antibodies ranging from 1000 nM to 0.016 nM were prepared using CHO starvation medium. Each antibody was made in duplicate to be tested in the absence and presence of SCF. Prior to addition of the antibody dilutions, the 96-well culture plate supernatants were removed and the cells were washed with 100 µL of starvation medium. After removal of the remaining starvation medium, 100 µL of the dilutions were transferred into each culture plate. The plate was incubated in a cell culture incubator at 37° C. for 2 hours. Cells on the bottom half of the plate were then stimulated by adding 10 µL/well of SCF, unstimulated well controls were also included, followed by incubation for 10 minutes in a cell culture incubator at 37° C.

Following stimulation, plates were placed on ice, cell culture supernatant removed and wells washed with cold PBS. Cold lysis buffer (100 µL/well) was then added and plates incubated on ice for 30-60 minutes to lyse the cells.

Approximately 1 hour prior to use, the coated MSD plates were blocked with 200 µL blocking buffer at room temperature in preparation for cell lysate. Prior to loading the sample, the blocking buffer was removed from the MSD plate and washed 3 times with TBS (~300 µL/well). Next, 50 µL of cell lysate was then transferred to the MSD plate.

Plates were then incubated for 1 hour at ambient temperature with shaking on an orbital plate shaker. The cell lysate was then removed, plates washed 3 times with TBST (~300 µL/well) and 50 µL/well of SULFO-TAG anti-phospho-tyrosine antibody diluted 1:500 in dilution buffer added. Plates were incubated for 1 hour at ambient temperature with shaking. The plates were then washed 3 times with TBST (~300 µL/well). Read Buffer T was diluted 1:4 in ddH$_2$O, 150 µL/well of substrate was added, and the luminescence of each well was then immediately measured using the Meso QuickPlex SQ 120 plate reader. Curves were fitted using a 4-parameter logistic model and half maximal inhibitory concentration (IC$_{50}$) values were interpolated, where possible, using GraphPad Prism 6.0.

Assay Protocol: KIT Phosphorylation in M-07e Cells

The human KIT expressing and SCF-responsive acute megakaryoblastic leukemia cell line M-07e (Avanzi, G C, et al., 1988, British J. Haematol. 69:359-366) was obtained from the Deutsche Sammlung von Mikroorganismen and Zellkulturen (DSMZ). Cells were maintained in M-07e complete medium.

M-07e cells were passed between 1 and 3 days prior to the assay. On the first day of the assay, cells were counted. Cells were spun down to remove the M-07e complete media and resuspended in M-07e starvation media at a concentration of $0.5 \times 10^6$ cells/mL. Cells were then plated in three 6-well dishes at $1 \times 10^6$ cells/well. Serial dilutions of anti-KIT-1 antibody were prepared using M-07e starvation medium at the following 20× concentrations: 20,000 nM, 2000 nM, 200 nM, 2 nM, 0.2 nM and 0.02 nM. Next, 100 µL of each dilution was added to the appropriate well in duplicate. The plate was incubated in a CO$_2$ incubator at 37° C. for 2 hours. After the 2 hour incubation, SCF was added to the appropriate wells at a final concentration of 30 ng/mL. Unstimulated and stimulated dishes were incubated at 37° C. for 10 minutes.

Following stimulation, plates were placed on ice and each sample was transferred to an ice cold 15 mL tube. Cells were spun at 1.2×g for 5 minutes and the supernatant was carefully aspirated. One (1) mL of ice cold PBS was added to each sample and transferred to microcentrifuge tubes. Cells were pelleted in a microcentrifuge and the supernatants were carefully aspirated. Cold lysis buffer (~300 µL) was added to each sample and incubated on ice for 30-60 minutes to lyse the cells. After the incubation, samples were spun to pellet debris and supernatants transferred into fresh microcentrifuge tubes.

One hour prior to use, 150 µL/well of Blocker A was added to a Phospho(Tyr721)/Total c-Kit MSD plate and blocked for 1 hour at room temperature with shaking (1000 rpm). Just prior to loading cell lysates, the blocking buffer was removed from the MSD plate and washed 3 times with 1× Tris wash buffer (~300 µL/well). Cell lysates were diluted by adding 20 µL of the sample into 35 µL of lysis buffer before transferring 25 µL into each of 2 wells of the MSD plate. The plate was incubated for 1 hour at ambient temperature with shaking on an orbital plate shaker (1000 rpm). The cell lysate was then removed and plate washed 3 times with 1× Tris wash buffer (~300 µL/well). The SULFO-TAG Anti-Total c-Kit detection antibody (included in reference number K15119D-2) was diluted 1:50 in antibody dilution buffer and 25 µL was added to each well. Plates were incubated for 1 hour at ambient temperature with shaking. The plates were then washed 3 times with 1× Tris wash buffer (~300 µL/well). Read Buffer T was diluted 1:4 in ddH2O just prior to use, and 150 µL/well was added to each well. Luminescence of each well was then immediately measured using the Meso QuickPlex SQ 120 plate reader.

Due to the experimental design, IC$_{50}$ values could not be accurately calculated for experiments done with M-07e cells. The percent inhibition (% Inhibition) values for anti-KIT-1 antibody treated cells were calculated relative the mean RLU values for control samples with SCF (% Inhibition=0) and without SCF (% Inhibition=100). The data were reported as % Inhibition of the doses at which less than the maximal inhibition was observed.

6.6.3 Results

Anti-KIT-1 Antibody Shows No Agonist Activity in Cell Lines Exogenously or Endogenously Expressing KIT

The effects of the anti-KIT-1 antibody and the isotype control antibody on KIT phosphorylation were assessed in the presence or absence of SCF in CHO-WT KIT cells. Representative data for the effects of anti-KIT-1 antibody on KIT phosphorylation in CHO-WT KIT cells are shown in FIG. 7. A summary of the data from the CHO-WT KIT studies is shown in Table 4.

TABLE 4

Summary of KIT Phosphorylation Data in CHO-WT KIT Cells

| Experiment Number | Antibody | SCF | Effect on KIT Phosphorylation |
|---|---|---|---|
| 1 | Anti-KIT-1 Antibody | − | No Effect |
|   |   | + | Dose-dependent Inhibition (IC$_{50}$ = 436 pM*) |
|   | Isotype Control Antibody | − | No Effect |
|   |   | + | No Effect |
| 2 | Anti-KIT-1 Antibody | − | No Effect |
|   |   | + | Dose-dependent Inhibition (IC$_{50}$ = 137 pM*) |
|   | Isotype Control Antibody | − | No Effect |
|   |   | + | No Effect |
| 3 | Anti-KIT-1 Antibody | − | No Effect |
|   |   | + | Dose-dependent Inhibition (IC$_{50}$ = 253 pM*) |
|   | Isotype Control Antibody | − | No Effect |
|   |   | + | No Effect |
| 4 | Anti-KIT-1 Antibody | − | No Effect |
|   |   | + | Dose-dependent Inhibition (IC$_{50}$ = 184 pM*) |
|   | Isotype Control Antibody | − | No Effect |
|   |   | + | No Effect |

*Average IC$_{50}$ from 2 plates

In CHO-WT KIT cells treated with SCF, anti-KIT-1 antibody inhibited KIT phosphorylation in a dose-dependent manner (FIG. 7) over 4 independent experiments. The isotype control antibody had no effect on SCF induced KIT phosphorylation. In the absence of SCF, the level of KIT phosphorylation was similar in cells treated with either anti-KIT-1 antibody or the isotype control antibody at concentrations up to 1 µM (150 µg/mL).

The effects of anti-KIT-1 antibody on KIT phosphorylation were also measured in the human acute megakaryoblastic leukemia cell line M-07e. Representative data are shown in FIG. 8. FIG. 8A shows the data for KIT phosphorylation. FIG. 8B shows the data for total KIT levels. A summary of the data from the M07e studies is shown in Table 5.

TABLE 5

Summary of KIT Phosphorylation Data in M-07e cells

| Experiment Number | Antibody | SCF | Effect on KIT Phosphorylation |
|---|---|---|---|
| 5 | Anti-KIT-1 Antibody | − | No Effect |
|   |   | + | 60% Inhibition at 10 pM |
| 6 | Anti-KIT-1 Antibody | − | No Effect |
|   |   | + | 73% Inhibition at 100 pM |
| 7 | Anti-KIT-1 Antibody | − | No Effect |
|   |   | + | 89% Inhibition at 100 pM |

In M-07e cells treated with SCF, anti-KIT-1 antibody inhibited KIT phosphorylation (FIG. 8A). In the absence of SCF, the level of KIT phosphorylation in cells treated with anti-KIT-1 antibody was similar to the untreated wells at concentrations of up to 1 µM (150 µg/mL; FIG. 8A). Total KIT levels were not affected with any of the experimental conditions (FIG. 8B).

These experiments demonstrate that the anti-KIT-1 antibody inhibits SCF induced KIT activation and does not have any agonistic activity on cells exogenously or endogenously expressing KIT.

6.7 Example 7: Anti-KIT-1 Antibody Treatment has Anti-Tumor Activity In Vivo in Dogs with Spontaneous Mastocytomas

6.7.1 Introduction

To extend the findings generated in healthy dogs, a clinical trial was conducted involving anti-KIT-1 antibody administration to dogs with spontaneous mast cell tumors (MCT).

6.7.2 Materials and Methods

Animals

This Example describes an open label study with dogs with measurable MCT including four cohorts (n=3/cohort).

Anti-KIT-1 Antibody Administration

Three dose levels and 2 schedules (10 and 30 mg/kg, administered for one cycle of four weeks; 1 and 10 mg/kg administered two cycles of three weeks each) were evaluated. Doses are infused over 4-6 hours.

Tumor Biopsy and Evaluation

For the four week schedule, base line tumor biopsies were obtained prior to first treatment with anti-KIT-1 antibody, 24-hours post-administration, at Day 7 post-administration, and, if possible on Day 28 following therapy. Blood samples were obtained pre-treatment, immediately post-treatment, and then again on Days 1, 7, 14, 21, and 28. For the three week, two cycle schedule, base line tumor biopsies were obtained prior to first treatment with anti-KIT-1 antibody, 24-hours post-administration, at Day 7 post-administration, and, if possible, on Day 42 following therapy. Blood samples were obtained pre-treatment, immediately post-treatment, and then again on Days 1, 7, 14, 21 (prior to and immediately post-treatment), 28, 35, and 42. Tumor measurements were also taken at each study visit.

Tumor samples were obtained under sedation and local anesthesia. The tumor specimens were divided in half, with the first half fixed in formalin and paraffin embedded, and the second half flash frozen in liquid nitrogen and stored at −80° C. or below. Up to 17 mL of blood was collected and used for CBC, biochemistry profiles, serum collection, plasma collection, immuophenotyping, and flow cytometry.

6.7.3 Results

All dogs treated with a single dose of anti-KIT-1 antibody at 10 and 30 mg/kg or two doses of anti-KIT-1 antibody at 10 mg/kg (n=9 total) experienced clinical benefit after the first dose. Under RECIST guidelines (see Eisenhauer et al., 2009, European J. Cancer 45:228-247), partial responses were observed in 4 dogs (n=1 with KIT exon 11 internal tandem duplications (ITD)) and stable disease was observed in 5 dogs (n=1 with KIT exon 11 ITD). In samples collected from dogs after study completion, histopathology failed to identify neoplastic mast cells in 2 primary tumor samples and 2 draining lymph nodes classified as metastatic at study entry. Thus, the data indicate that treatment of the dogs appears to result in a depletion of mast cells in the primary tumor samples and/or draining lymph nodes. Reversible hematologic changes including anemia, neutropenia, and thrombocytopenia were the most common study related adverse events.

The data demonstrate that anti-KIT-1 antibody exhibits an acceptable safety profile in a relevant large animal model and has antitumor activity in canine MCT expressing either wild-type or mutant KIT. Moreover, these data indicate that there is a reduction in activated mast cell numbers in a large animal in vivo mast cell disease model expressing a wild-type or mutant KIT. These findings are consistent with the preclinical work in healthy laboratory dogs, demonstrating significant reductions in mast cells in the skin after one dose of anti-KIT-1 antibody. Collectively, these data support use of anti-KIT-1 antibody in the treatment or maintenance of mast cell related disorders, including diseases involving activated mast cells.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

Other embodiments are within the following claims.

What is claimed:

1. A method of reducing inflammation or inhibiting mast cell activation in a subject, comprising administering to a subject diagnosed with a mast cell related disorder of the nervous system a therapeutically effective amount of an antibody which specifically binds to a human KIT receptor (SEQ ID NO: 1), or an antigen binding fragment thereof, wherein the antibody or antigen binding fragment thereof comprises a light chain variable region ("VL") comprising VL CDRs 1-3 comprising SEQ ID NOs: 2-4, respectively, and a heavy chain variable region ("VH") comprising VH CDRs 1-3 comprising SEQ ID NOs: 5-7, respectively.

2. The method of claim 1, wherein the mast cell related disorder of the nervous system is neuromyelitis optica (NMO) or neuromyelitis optica spectrum disorder (NMOSD).

3. The method of claim 1, wherein the antibody is a humanized antibody.

4. The method of claim 1, wherein the antibody comprises a VL comprising a VL sequence selected from the group consisting of SEQ ID NOs: 13, 14, 15, and 16; and a VH comprising a VH sequence selected from the group consisting of SEQ ID NOs: 8, 9, 10, 11, and 12.

5. The method of claim 1, wherein the subject is a human adult.

6. The method of claim 1, wherein the subject is a child.

7. The method of claim 1, comprising administering a therapeutically effective amount of an antibody which specifically binds to a human KIT receptor (SEQ ID NO: 1).

* * * * *